(12) United States Patent
Ashley et al.

(10) Patent No.: US 10,172,916 B2
(45) Date of Patent: Jan. 8, 2019

(54) METHODS OF TREATING HEART FAILURE WITH AGONISTS OF HYPOCRETIN RECEPTOR 2

(71) Applicant: The Board of Trustees of the Leland Stanford Junior University, Stanford, CA (US)

(72) Inventors: Euan A. Ashley, Menlo Park, CA (US); Marco V. Perez, Burlingame, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 180 days.

(21) Appl. No.: 15/037,030

(22) PCT Filed: Nov. 13, 2014

(86) PCT No.: PCT/US2014/065519
§ 371 (c)(1),
(2) Date: May 16, 2016

(87) PCT Pub. No.: WO2015/073707
PCT Pub. Date: May 21, 2015

(65) Prior Publication Data
US 2016/0271214 A1    Sep. 22, 2016

Related U.S. Application Data

(60) Provisional application No. 61/905,145, filed on Nov. 15, 2013.

(51) Int. Cl.
| | | |
|---|---|---|
| *A61K 38/17* | (2006.01) | |
| *A61K 38/22* | (2006.01) | |
| *A61K 45/06* | (2006.01) | |
| *C12Q 1/6883* | (2018.01) | |
| *C12Q 1/6876* | (2018.01) | |

(52) U.S. Cl.
CPC .......... *A61K 38/1709* (2013.01); *A61K 38/22* (2013.01); *A61K 45/06* (2013.01); *C12Q 1/6876* (2013.01); *C12Q 1/6883* (2013.01); *C12Q 2600/106* (2013.01); *C12Q 2600/156* (2013.01)

(58) Field of Classification Search
CPC .... A61K 38/1079; A61K 38/22; A61K 45/06; C12Q 1/6883; C12Q 2600/156; C12Q 2600/106
See application file for complete search history.

(56) References Cited

U.S. PATENT DOCUMENTS

| | | |
|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,174,384 A | 11/1979 | Ullman et al. |
| 4,275,149 A | 6/1981 | Litman et al. |
| 4,277,437 A | 7/1981 | Maggio |
| 4,318,846 A | 3/1982 | Khanna et al. |
| 4,366,241 A | 12/1982 | Tom et al. |
| 4,415,732 A | 11/1983 | Caruthers et al. |
| 4,458,066 A | 7/1984 | Caruthers et al. |
| 4,605,735 A | 8/1986 | Miyoshi et al. |
| 4,666,828 A | 5/1987 | Gusella |
| 4,757,141 A | 7/1988 | Fung et al. |
| 4,801,531 A | 1/1989 | Frossard |
| 4,914,210 A | 4/1990 | Levenson et al. |
| 5,110,920 A | 5/1992 | Erlich |
| 5,122,458 A | 6/1992 | Post et al. |
| 5,135,855 A | 8/1992 | Moss et al. |
| 5,139,941 A | 8/1992 | Muzuczka et al. |
| 5,168,062 A | 12/1992 | Stinski et al. |
| 5,173,414 A | 12/1992 | Lebkowski et al. |
| 5,219,740 A | 6/1993 | Miller et al. |
| 5,268,267 A | 12/1993 | Smith |
| 5,385,839 A | 1/1995 | Stinski et al. |
| 5,387,506 A | 2/1995 | Blumenfeld et al. |
| 5,491,224 A | 2/1996 | Bittner et al. |
| 5,676,950 A | 10/1997 | Meitin et al. |
| 5,691,153 A | 11/1997 | Recker et al. |
| 5,695,739 A | 12/1997 | Schmitt-Wllich et al. |
| 5,695,934 A | 12/1997 | Brenner |
| 5,698,339 A | 12/1997 | Kawakami et al. |
| 5,733,528 A | 3/1998 | Felder et al. |
| 5,736,330 A | 4/1998 | Fulton |
| 5,783,565 A | 7/1998 | Lee et al. |
| 5,789,245 A | 8/1998 | Dubensky, Jr. et al. |
| 5,798,092 A | 8/1998 | Schmitt-Willich et al. |
| 5,834,200 A | 11/1998 | Rousseau |
| 5,837,533 A | 11/1998 | Boutin |
| 5,843,723 A | 12/1998 | Dubensky, Jr. et al. |

(Continued)

FOREIGN PATENT DOCUMENTS

| | | |
|---|---|---|
| EP | 273085 A1 | 7/1988 |
| EP | 3068783 A1 | 9/2016 |

(Continued)

OTHER PUBLICATIONS

Extended European Search Report for European Application No. 15739921.3, Search completed Sep. 4, 2017, dated Dec. 20, 2017, 13 Pgs.

(Continued)

*Primary Examiner* — Ruixiang Li
(74) *Attorney, Agent, or Firm* — KPPB LLP

(57) ABSTRACT

Methods of treating individuals for heart failure are disclosed. In particular, the invention relates to methods of treating individuals for heart failure with agonists of hypocretin receptor 2. The invention further relates to the use of genetic analysis of the single nucleotide polymorphism rs7767652, which resides immediately upstream of the HCRTR2 gene, to identify individuals in need of treatment for heart failure who are predicted to be more responsive to medical intervention.

8 Claims, 15 Drawing Sheets
Specification includes a Sequence Listing.

(56) References Cited

U.S. PATENT DOCUMENTS

| | | | |
|---|---|---|---|
| 5,844,107 | A | 12/1998 | Hanson et al. |
| 5,877,302 | A | 3/1999 | Hanson et al. |
| 5,888,576 | A | 3/1999 | Nagano et al. |
| 5,922,542 | A | 7/1999 | Ralston et al. |
| 5,972,900 | A | 10/1999 | Ferkol et al. |
| 5,972,901 | A | 10/1999 | Ferkol et al. |
| 5,981,505 | A | 11/1999 | Wang et al. |
| 5,998,137 | A | 12/1999 | Grainger et al. |
| 6,008,336 | A | 12/1999 | Hanson et al. |
| 6,077,835 | A | 6/2000 | Hanson et al. |
| 6,127,170 | A | 10/2000 | Boutin |
| 6,200,801 | B1 | 3/2001 | Ferkol, Jr. et al. |
| 6,217,900 | B1 | 4/2001 | Ciccarelli et al. |
| 6,379,965 | B1 | 4/2002 | Boutin et al. |
| 6,383,512 | B1 | 5/2002 | Ciccarelli et al. |
| 6,747,014 | B2 | 6/2004 | Teng et al. |
| 7,202,227 | B2 | 4/2007 | Boutin et al. |
| 2002/0150626 | A1 | 10/2002 | Kohane et al. |
| 2003/0032615 | A1 | 2/2003 | Felgner et al. |
| 2003/0203865 | A1 | 10/2003 | Harvie et al. |
| 2004/0005615 | A1 | 1/2004 | Li et al. |
| 2004/0048787 | A1 | 3/2004 | Cooper et al. |
| 2006/0003344 | A1 | 1/2006 | Houseknecht et al. |
| 2007/0031847 | A1 | 2/2007 | Cargill et al. |
| 2007/0093440 | A1 | 4/2007 | Champion |
| 2007/0105109 | A1 | 5/2007 | Geesaman et al. |
| 2007/0111227 | A1 | 5/2007 | Green et al. |
| 2010/0113283 | A1 | 5/2010 | Strathmann |
| 2011/0020320 | A1 | 1/2011 | Gudmundsson et al. |
| 2011/0213010 | A1 | 9/2011 | Hayden et al. |
| 2012/0040460 | A1 | 2/2012 | Rigoutsos et al. |
| 2012/0196920 | A1 | 8/2012 | Hazum et al. |
| 2013/0137672 | A1 | 5/2013 | Branstetter et al. |
| 2013/0311107 | A1 | 11/2013 | Stuelpnagel et al. |
| 2013/0316331 | A1 | 11/2013 | Isakov et al. |
| 2014/0045706 | A1 | 2/2014 | Fan et al. |
| 2016/0237430 | A1 | 8/2016 | Seidman et al. |
| 2016/0298114 | A1 | 10/2016 | Wheeler et al. |
| 2016/0348103 | A1 | 12/2016 | Wheeler et al. |

FOREIGN PATENT DOCUMENTS

| | | |
|---|---|---|
| WO | 1989003429 | 4/1989 |
| WO | 1991012882 | 9/1991 |
| WO | 1992001070 | 1/1992 |
| WO | 1992003545 | 3/1992 |
| WO | 1993003769 | 3/1993 |
| WO | 1994026911 | 11/1994 |
| WO | 1995007995 | 3/1995 |
| WO | 1996017072 | 6/1996 |
| WO | 2000001772 | 10/2000 |
| WO | 2000071096 A2 | 11/2000 |
| WO | 2001081609 | 11/2001 |
| WO | 2002080982 | 10/2002 |
| WO | 2002099035 | 12/2002 |
| WO | 2003093449 | 11/2003 |
| WO | 2010004590 A2 | 1/2010 |
| WO | 2013088457 A1 | 6/2013 |
| WO | 2015042581 A1 | 3/2015 |
| WO | 2015073707 A1 | 5/2015 |
| WO | 2015113004 A2 | 7/2015 |
| WO | 2016149684 | 9/2016 |

OTHER PUBLICATIONS

Sakurai, et al., Cell, 1996, vol. 92, No. 1, page following 696.
Zaleta-Rivera, "Oligonucleotide therapeutic approaches for allele silencing of hMYL2-47K and hMYH7-403Q mutations in hypertrophic cardiomyopathy", J. Clin. Exp. Cardiolog. vol. 4, No. 4, Apr. 15-17, 2013, p. 132.
Orum et al., "Locked nucleic acids: A promising molecular family for gene-function analysis and antisense drug development", Current Opinion Molecular Therapeutics, 2001, vol. 3, No. 3, 2001, p. 239-243.
Paddison et al., "RNA Interference in Mammalian Cell Systems", Current Topics in Microbiology and Immunology, 2008, vol. 320, 14 pgs.
Perales et al., "Gene transfer in vivo: Sustained expression and regulation of genes introduced into the liver by receptor-targeted uptake", Proc. Natl. Acad. Sci. USA, Medical Sciences, Apr. 1994, vol. 91, pp. 4086-4090.
Perez et al., "Genetics of Arrhythmia: Disease Pathways Beyond Ion Channels", J. of Cardiovasc. Transl. Res., May 15, 2008, vol. 1, pp. 155-165.
Perri et al., "An Alphavirus Replicon Particle Chimera Derived from Venezuelan Equine Encephalitis and Sindbis Viruses is a Potent Gene-Based Vaccine Delivery Vector", Journal of Virology, Oct. 2003, vol. 77, No. 19, pp. 10394-10403.
Petzold et al., "The transcript catalogue of the short-lived fish Nothobranchius furzeri provides insights into age-dependent changes of mRNA levels", BMC Genomics, 2013, vol. 14, No. 185, pp. 1-16.
Potter et al., "Enhancer-dependent expression of human k immunoglobulin genes introduced into mouse pre-B lymphocytes by electroporation", Proc. Natl. Acad. Sci. USA, Genetics, Nov. 1984, vol. 81, pp. 7161-7165.
Psifidi et al., "Novel Quantitative Real-Time LCR for the Sensitive Detection of SNP Frequencies in Pooled DNA: Method Development, Evaluation and Application", PLoS One, Jan. 19, 2011, vol. 6, No. 1, pp. e14560-1-e14560-11.
Purcell et al., "PLINK: A Tool Set for Whole-Genome Association and Population-Based Linkage Analyses", The American Journal of Human Genetics, Sep. 2007, vol. 81, pp. 559-575.
Rape et al., "The Regulation of Traction Force in Relation to Cell Shape and Focal Adhesions", Biomaterials, Mar. 1, 2011, vol. 32, No. 8, pp. 2043-2051; doi:10.1016/j.biomaterials.2010.00.044.
Rich et al., "Development and Analysis of Recombinant Adenoviruses for Gene Therapy of Cystic Fibrosis", Human Gene Therapy, Apr. 20, 1993, vol. 4. pp. 461-476.
Rippe et al., "DNA-Mediated Gene Transfer into Adult Rat Hepatocytes in Primary Culture", Molecular and Cellular Biology, Feb. 1990, vol. 10, No. 2, pp. 689-695.
Roeder et al., "Improving Power in Genome-Wide Association Studies: Weights Tip the Scale", Genetic Epidemiology, Apr. 4, 2007, vol. 31, p. 741-747.
Samson et al., "Cardiovascular regulatory actions of hypocretins in brain", Brain Research, Mar. 30, 1999, vol. 831, pp. 248-253.
Sato et al., "Label-Free Molecular Beason System Based on DNAs Containing Abasic Sites and Fluorescent Ligands That Bind Abasic Sites", Chemistry Eur. J., Aug. 26, 2011, vol. 17, pp. 11650-11656.
Scarpa et al., "Characterization of Recombinant Helper Retroviruses from Moloney-Based Vectors in Ecotropic and Amphotropic Packaging Cell Lines", Virology, 1991, vol. 180, pp. 849-852.
Seth et al., "Mechanism of Enhancement of DNA Expression Consequent to Cointernalization of a Replication-Deficient Adenovirus and Unmodified Plasmid DNA", Journal of Virology, Feb. 1994, vol. 68, No. 2, pp. 933-940.
Shelling, et al., "Targeted integration of transfected and infected adeno-associated virus vectors containing the neomycin resistance gene", Gene Therapy, 1994, vol. 1, pp. 165-169.
Shirasaka et al., "Sympathetic and cardiovascular actions or orexins in conscious rats", Am. J. Physiol., vol. 277, 1999, p. R1780-R1785.
Smith et al., "The Association of Genome-Wde Variation with the Risk of Incident Heart Failure in Adults of Europe and and African Ancestry: A Prospective Meta-Analysis from the CHARGE Consortium", Circ. Cardiovasc. Genet. Jun. 1, 2010, vol. 3, No. 3, pp. 256-266.
Smith et al., "The Synthesis and Use of Fluorescent Oligonucleotides in DNA Sequence Analysis", Methods in Enzymology, 1987, vol. 155, pp. 260-301.
Smyth et al., "Normalization of cDNA Microarray Data", Methods, Apr. 4, 2003, vol. 31, p. 265-273.
Sommer et al., "A Novell Method for Detecting Point Mutations of Polymorphisms and Its Application to Population Screening for Carriers of Phenylketonuria", Mayo Clin. Proc., Nov. 1989, vol. 64, pp. 1361-1372.

(56) References Cited

OTHER PUBLICATIONS

Sproat, et al., "The synthesis of protected 5'-mercapto-2', 5'-dideoxyribonucleoside-3'-O-phosphoramidites; uses of 5'-mercapto-oligodeoxyribonucleotides", Nucl. Acids Res., May 22, 1987, vol. 15, No. 12, p. 4837-4848.
Stark et al., "Genetic Association Study Identifies HSPB7 as a Risk Gene for Idopathic Dilated Cardiomyopathy", PLoS Genetics, Oct. 21, 2010, vol. 6, No. 10, pp. e1001167-1-e1001167-9.
Storey et al., "Statistical Methods for Identifying Differentially Expressed Genes in DNA Microarrays", Methods in Molecular Biology, 2003, vol. 224, pp. 149-157, plus cover.
Studier et al., "Use of Bacteriophage T7 RNA Polymerase to Direct Selective High-level Expression of Cloned Genes", J. Mol. Biol., 1986, vol. 189, pp. 113-130.
Tur-Kaspa et al., "Use of Electroporation to Introduce Biologically Active Foreign Genes into Primary Rate Hepatocytes", Molecular and Cellular Biology, Feb. 1986, vol. 6, No. 2, pp. 716-718.
Villard et al., "A genome-wide association study identifies two loci associated with heart failure due to dilated cardiomyopathy", Eur. Heart J., Apr. 1, 2011, vol. 32, p. 1065-1076.
Wagner et al., "Coupling of adenovirus to transferrin-polylysine/DNA complexes greatly enhances receptor-mediated gene delivery and expression of transfected genes", Proc. Natl. Acad. Sci. USA, Biochemistry, Jul. 1992, vol. 89, pp. 6099-6103.
Wagner et al., "Transferrin-polycation conjugates as carriers for DNA uptake into cells", Proc. Natl. Acad. Sci. USA, May 1990, vol. 87, pp. 3410-3414.
Walther et al., "Viral Vectors for Gene Transfer", Drugs, Aug. 2000, vol. 60, No. 2, pp. 249-271.
Wang et al., "Molecular Engineering of DNA: Molecular Beacons", Angew. Chem. Int. Ed. Engl., Nov. 3, 2009, vol. 48, No. 5, p. 856-870.
Wang et al., "Preparation of a flexible, porous polyacrylamide substrate for mechanical studies of cultured cells", Methods in Enzymology, 1998, vol. 298, pp. 489-496.
Warnock et al., "Introduction to Viral Vectors", Methods in Molecular Biology, 2011, vol. 737, pp. 1-25, plus cover.
Wei et al., "Comparison of PCR ribotyping and multilocus variable-number tandem-repeat analysis (MLVA) for improved detection of Clostridium difficile", BMC Microbiology, Sep. 30, 2011, vol. 11, pp. 1-13.
Wheeler et al., "Cost effectiveness of pre-participation screening for prevention of sudden cardia death in young athletes", Am. Intern. Med., Mar. 2, 2010, vol. 152, No. 5, pp. 276-286; doi: 10.1059/0003-4819-152-5-201003020-00005.
Whitlock, "Combining probability from independent tests: the weighted Z-method is superior to Fisher's approach", J. Evol. Biol., Feb. 2005, vol. 18, p. 1368-1373.
Wu et al., "Evidence for Targeted Gene Delivery to Hep G2 Hepatoma Cells in Vitro", Biochemistry 1988, vol. 27, pp. 887-892.
Wu et al., "Receptor-mediated in Vitro Gene Transformation by a Soluble DNA Carrier System", The Journal of Biological Chemistry, Apr. 5, 1987, vol. 262, No. 10, pp. 4429-4432.
Yang et al., "In vivo and in vitro gene transfer to mammalian somatic cells by particle bombardment", Proc. Natl. Acad. Sci. USA, Genetics, Dec. 1990, vol. 87, pp. 9568-9572.
Yu et al., "DNA Mutation Detection Using Denaturing High-Performance Liquid Chromatography (DHPLC)", Curr. Protoc. Hum. Genet., 2006, Chapter 7: Unit 7.10-7.10.14.
Zaleta-Rivera, Oligonucleotide therapeutic approaches for allele silencing of hMYL2-47K and 1-20 hMYH7-403Q mutations in hypertrophic cardiomyopathy, J Clin Exp Cardiolog. Apr. 15-17, 2013, vol. 4, No. 4, p. 132.
Zhou et al., "Adeno-associated Virus 2-mediated High Efficiency Gene Transfer into Immature and Mature Subsets of Hematopoietic Progenitor Cells in Human Umbilical Cord Blood", J. Exp. Med, Jun. 1994, vol. 179, pp. 1867-1875.
Extended European Search Report for European Application No. 14862291.3, Search completed Jun. 6, 2017, dated Jul. 7, 2017 12 pages.

International Preliminary Report on Patentability for International Application PCT/US2016/023305, dated Sep. 19, 2017, dated Sep. 28, 2017, 12 pages.
Supplementary Partial European Search Report for European Application No. 15739921.3, completed Sep. 4, 2017, dated Sep. 14, 2017, 16 pages.
Chen et al., "The Effect of Orexin-A on Cardiac Dysfunction Mediated by NADPH Oxidase-Derived Superoxide Anion in Ventrolateral Medulla", PLOS ONE, vol. 8, Issue No. 7, Jul. 26, 2013, pp. 1-13.
Dames et al., "Comparison of the Illumina Genome Analyzer and Roche 454 GS FLX for Resequencing of Hypertrophic Cardiomyopathy-Associated Genes", Journal of Biomolecular Techniques, vol. 21, 2010, pp. 73-80.
Fechheimer et al., "Transfection of mammalian cells with plasmid DNA by scrape loading and sonication loading", Proc. Natl. Acad. Sci. USA, Dec. 1987, vol. 84, pp. 8463-8467.
Jiang et al., "Allele-Specific Silencing of Mutant Myh6 Transcripts in Mice Suppresses Hypertrophic Cardiomyopathy", vol. 342, No. 6154, Oct. 4, 2013, pp. 111-114.
Kannan et al., "Central action of orexin-A on the neural activity of hypothalamic paraventricular nucleus neuron", Autonomic Neuroscience: Basic and Clinical, vol. 135, No. 1, Sep. 30, 2007, pp. 122-123.
Perez et al., "Genetic Determinants of Dramatic Improvement in Left Ventricular Function in Patients With Heart Failure ACC Poster Contributions", ACC.11 Best Poster Award Competition, E2041, JACC, Apr. 5, 2011, vol. 57, Issue 14, 1 page.
Perez et al., "Genetic Variation Near HCRTR2 Associates With Dramatic Improvement of Heart Function in Patients With Heart Failure", Circulation 2013 by American Heart Association, Inc., vol. 128, Issue No. 22, Nov. 26, 2013, 6 pages.
Tajsharghi et al., "Myosinopathies: pathology and mechanism", ACTA Neuropathologica, Springer, Berlin, DE, vol. 125, No. 1, Jan. 2013, published online Aug. 5, 2012, pp. 3-18.
Chuang et al., "Restriction Enzyme Mining for SNPs in Genomes", Anticancer Res., vol. 28(4A), May 9, 2008, p. 2001-2007.
Cload et al., "Polyether Tethered Oligonucleotide Probes", J. Am. Chem. Soc., vol. 113, Mar. 8, 1991, p. 6324-6326.
Connolly, "The synthesis of oligonucleotides containing a primary amino group at the 5'-terminus", Nucleic Acids Research, Mar. 2, 1987, vol. 15, No. 7, pp. 3131-3139.
Connolly et al., "Chemical synthesis of oligonucleotides containing a free sulphydryl group and subsequent attachment of thiol specific probes", Nucl. Acids Res., vol. 13, No. 12, May 22, 1985, p. 4485-4502.
Cresci et al., "Clinical and Genetic Modifiers of Long-term Survival in Heart Failure", J. Am. Coll. Cardiol., vol. 54, No. 5, Jul. 28, 2009, p. 432-444.
Deng et al., "Self-amplifying expression from the T7 promoter in 3T3 mouse fibroblasts", Gene, Feb. 21, 1994, vol. 143, pp. 245-249.
Dewey et al., "Gene Coexpression Network Topology of Cardiac Development, Hypertrophy, and Failure", Circ. Cardiovasc. Genet., vol. 4, 2011, p. 26-35 (with supplement).
Dewey et al., "Phased Whole-Genome Genetic Risk in a Family Quartet Using a Major Allele Reference Sequence", PLoS Genetics, Sep. 15, 2011, vol. 7, Issue 9, 15 pgs.
Dijkema et al., "Cloning and expression of the chromosomal immune interferon gene of the rat", The EMBO Journal, Jan. 17, 1985, vol. 4, No. 3, pp. 761-767.
Dubensky et al., "Direct transfection of viral and plasmid DNA into the liver or spleen of mice", Proc. Natl. Acad. Sci. USA, Dec. 1984, vol. 81, pp. 7529-7533.
Dubensky, Jr. et al., "Sindbis Virus DNA-Based Expression Vectors: Utility for In Vitro and In Vivo Gene Transfer", Journal of Virology, Jan. 1996, vol. 70, No. 1, pp. 508-519.
Durand et al., "Circular dichroism studies of an oligodeoxribonucleotide containing a hairpin loop made of a hexaethylene glycol chain: conformation and stability", Nucleic Acids Res., vol. 18, No. 21, Sep. 20, 1990, p. 6353-6359.
Durand et al., "The Inside Out of Lentiviral Vectors", Viruses, Feb. 14, 2011, vol. 3, pp. 132-159; doi:10.3390/v3020132.

(56) References Cited

OTHER PUBLICATIONS

Eberle, M. A., "Allele Frequency Matching Between SNPs Reveals an Excess of Linkage Disequilibrium in Genic Regions of the Human Genome", PLoS Genetics, Sep. 8, 2006, vol. 2, No. 9, pp. 1319-1327.
Elayadi et al., "Application of PNA and LNA oligomers to chemotherapy", Curr. Opinion Invest. Drugs, 2001, vol. 2, pp. 558-561.
Elroy-Stein et al., "Cytoplasmic expression system based on constitutive synthesis of bacteriophage T7 RNA polymerase in mammalian cells", Proc. Natl. Adad. Sci. BUS, Biochemistry, Sep. 1990, vol. 87, pp. 6743-6747.
Ferkol et al., "Regulation of the phosphoenolpyruvate carboxykinase/human factor IX gene introduced into the livers of adult rats by receptor-mediated gene transfer", The FASEB Journal, Dec. 2016, vol. 7, No. 11, pp. 1081-1091.
Ferry et al., "Retroviral Vector-mediated Gene Therapy for Metabolic Diseases: An Update", Current Pharmaceutical Design, Jun. 28, 2011, vol. 17, No. 24, pp. 2516-2527.
Fraley et al., "Entrapment of a bacteria plasmid in phospholipid vesicles: Potential for gene transfer", Cell Biology, Proc. Natl. Acad. Sci. USA, Jul. 1979, vol. 76, No. 7, pp. 3348-3352.
Franck et al., "Three-Dimensional Traction Force Microscopy: A New Tool for Quantifying Cell-Matrix Interactions", PLoS one, Mar. 29, 2011, vol. 6, No. 3, pp. e17833-1-e17833-15.
Fuerst et al., "Eukaryotic transient-expression system based on recombinant vaccinia virus that synthesized bacteriophage T7 RNA polymerase", Proc. Natl. Acad. Sci. USA, Biochemistry, Nov. 1986, vol. 83, pp. 8122-8126.
Galeano et al., "Single strand conformation polymorphism based SNP and Indel markers for genetic mapping and synteny analysis of common bean (*Phaseolus vulgaris* L.)", BMC Genomics, Dec. 23, 2009, vol. 10, No. 629, 14 pgs.
Gall et al., "Formation and Detection of RNA-DNA Hybrid Molecules in Cytological Preparations", Proc. Natl. Acad. Sci. U.S.A., Mar. 27, 1969, vol. 63, pp. 378-383.
Gao et al., "Cytoplasmic expression of a reporter gene by co-delivery of T7 RNA polymerase and T7 promoter sequence with cationic liposomes", Nucleic Acids Research, Apr. 25, 1993, vol. 21, No. 12, pp. 2867-2872.
Genovese et al., "False discovery control with p-value weighting", Biometrika, Jan. 2006, vol. 93, No. 3, pp. 509-524.
Gibson et al., Synthesis and application of derivatizable oligonucleotides Nucleic Acids Research, Jul. 16, 1987, vol. 15, No. 16, pp. 6455-6467.
Gopal, "Gene Transfer Method for Transient Gene Expression, Stable Transformation, and Cotransformation of Suspension Cell Cultures", Molecular and Cellular Biology, May 1985, vol. 5, No. 5, pp. 1188-1190.
Gorman et al., "The Rous sarcoma virus long terminal repeat is a strong promoter when introduced into a variety of eukaryotic cells by DNA-mediated transfection", Proc. Natl. Acad. Sci. USA, Nov. 1982, vol. 79, p. 6777-6781.
Graham, "Growth of 293 Cells in Suspension Culture", J. gen. Virol., 1987, vol. 68, pp. 937-940.
Graham et al., "A new technique for the assay of infectivity of human adenovirus 5 DNA", Virology, Jan. 17, 1973, vol. 52, pp. 456-467.
Green et al., "Molecular Cloning: A Laboratory Manual", Cold Spring Harbor Laboratory Press, 4th edition, 2012, 34 pgs.
Greenough et al., "Evidence for active synapse formation of altered postsynaptic metabolism in visual cortex of rats reared in complex environments", Proc. Natl. Acad. Sci. USA, Neurobiology, Jul. 1985, vol. 82, pp. 4549-4522.
Guo et al., "Fluorescent hybridization probes for nucleic acid detection", Anal. Bioanal. Chem., vol. 402(10), 2012, p. 3115-3125.
Haj-Ahmad et al., "Development of a Helper-Independent Human Adenovirus Vector and Its Use in the Transfer of the Herpes Simplex Virus Thymidine Kinase Gene", Journal of Virology, Jan. 1986, vol. 57, No. 1, pp. 267-274.
Hajeri et al., "SiRNAs: their potential as therapeutic agents—Part I. Designing of siRNAs", Drug Discovery Today, Sep. 2009, vol. 14, Nos. 17/18, pp. 851-858.
Hall et al., "Sensitive detection of DNA polymorphisms by the serial invasive signal amplification reaction", Proc. Natl. Acad. Sci. U.S. A., May 17, 2000, vol. 97, No. 15, p. 8272-8277.
Harland et al., "Translation of mRNA Injected into Xenopus Oocytes is Specifically Inhibited by Antisense RNA", The Journal of Cell Biology, Sep. 1, 1985, vol. 101, pp. 1094-1099.
Heidenreich et al., "Forecasting the Future of Cardiovascular Disease in the United States", Circulation, Mar. 1, 2011, vol. 123, pp. 933-944.
Ho et al., "The Epidemiology of Heart Failure: The Framingham Study", J. Am. Coll. Cardiol., Oct. 1993, vol. 22, No. 4, p. 6A-13A.
Horn et al., "A Chemical 5'-Phosphorylation of Oligodeoxyribonucleotides that can be Monitored by Trityl Cation Release", Tetrahedron Letters, May 28, 1986, vol. 27, No. 39, pp. 4705-4708.
Howell et al., "Dynamic allele-specific hybridization", Nature Biotechnology, Jan. 1999, vol. 17, pp. 87-88.
Hsu et al., "Genotyping Single-Nucleotide Polymorphisms by the Invader Assay with Dual-Color Fluorescence Polarization Detection", Clin. Chem., May 23, 2001, vol. 47 No. 8, p. 1373-1377.
Jang et al., "Initiation of Protein Synthesis by Internal Entry of Ribosomes into the 5' Nontranslated Region of Encephalomyocarditis Virus RNA In Vivo", Journal of Virology, Apr. 1989, vol. 63, No. 4, pp. 1651-1660.
Jeong et al., "The large-scale organization of metabolic networks", Nature, Oct. 5, 2000, vol. 407, p. 651-654.
John et al., "RNA-DNA Hybrids at the Cytological Level", Nature, Aug. 9, 1969, vol. 223, p. 582-587.
Jones et al., "Markers and Mapping revisited: finding your Gene", New Phytol., 2009, vol. 183, pp. 935-966.
International Preliminary Report on Patentability for International Application PCT/US2015/012966, dated Aug. 2, 2016, dated Aug. 11, 2016, 9 Pgs.
International Search Report and Written Opinion for International Application No. PCT/US2014/065519, completed Jan. 27, 2015, dated Mar. 3, 2016, 12 pgs.
International Search Report and Written Opinion for International Application No. PCT/US2015/012966, completed Jul. 13, 2015, dated Jul. 30, 2015, 12 Pgs.
International Search Report and Written Opinion for International Application No. PCT/US2016/023305, completed Sep. 6, 2016, dated Sep. 16, 2016, 17 Pgs.
Agalioti et al., "Deciphering the Transcriptional Histone Acetylation Code for a Human Gene", Cell, Nov. 1, 2002, vol. 111, pp. 381-392.
Asari et al., "Enhanced discrimination of single nucleotide polymorphisms using 3' nucleotide differences in ligase detection reaction probes", Molecular and Cellular Probes, Aug. 24, 2010, vol. 24, pp. 381-386.
Ashley et al., "Network Analysis of Human In-Stent Restenosis", Circulation, Sep. 22, 2006, vol. 114, pp. 2644-2654.
Basu et al., "Biosynthesis in vitro of SA-Le$^x$ and SAx-diLe$^x$ by α1-3 fucosyltransferases from colon carcinoma cells and embryonic brain tissues", Glycobiology, Sep. 23, 1991, vol. 1, No. 5, pp. 527-535.
Benvenisty et al., "Direct introduction of genes into rats and expression of the genes", Proc. Natl. Acad. Sci. USA, Genetics, Dec. 1986, vol. 83, pp. 9551-9555.
Berkner, "Development of Adenovirus Vectors for the Expression of Heterologous Genes", BioTechniques, 1988, vol. 6, Issue 7, pp. 616-629.
Bett et al., "Packaging Capacity and Stability of Human Adenovirus Type 5 Vectors", Journal of Virology, Oct. 1993, vol. 67, No. 10, pp. 5911-5921.
Bick et al., "Burden of Rare Sarcomere Gene Variants in the Framingham and Jackson Heart Study Cohorts", The American Journal of Human Genetics. Sep. 7, 2012. vol. 91, No. 3; pp. 513-519; abstract, p. 516, col. 1, paragraph 5; DOI: 10.1 016/j.ajhg. 2012.07 .017.
Boris-Lawrie et al., "Recent advances in retrovirus vector technology", Current Opinion in Genetics and Development, 1993, vol. 3, pp. 102-109.

(56) References Cited

OTHER PUBLICATIONS

Bray et al., "Sarcomere Alignment is Regulated by Myocyte Shape", Cell Monti Cytoskeleton, Aug. 2008, vol. 65, No. 8, pp. 641-651; doi:10.1002/cm.20290.

Broker et al., "Electron microscopic visualization or tRNA genes with ferritin-avidin: biotin labels", Nucleic Acids Research, Feb. 1978, vol. 5, No. 2, pp. 363-384.

Brown et al., "Chemical Synthesis and Cloning of a Tyrosine tRNA Gene", Methods in Enzymology, 1979, vol. 68, pp. 109-151.

Burns et al., "Vesicular stomatitis virus G Glycoprotein pseudotyped retroviral vectors: Concentration to very high titer and efficient gene transfer into mammalian and nonmammalian cells", Proc. Natl. Acad. Sci., USA, Sep. 1993, vol. 90, pp. 8033-8037.

Cappola et al., "Common variants in HSPB7 and FRMD4B associated with advanced heart failure", Circ. Cardiovasc. Genet., Apr. 2010, vol. 3, No. 2, pp. 147-154.

Carter, "Adeno-associated virus vectors", Current Opinion in Biotechnology, 1992, vol. 3, pp. 533-539.

Chang et al., "SNP-RFLPing: restriction enzyme mining for SNPs in genomes", BMC Genomics, Feb. 17, 2006, vol. 7, 7 pgs.

Chemelli et al., "Narcolepsy in orexin Knockout Mice: Molecular Genetics of Sleep Regulation", Cell, vol. 98, Aug. 20, 1999, p. 437-451.

Chen et al., "A self-initiating eukaryotic transient gene expression system based on cotransfection of bacteriophage T7 RNA polymerase and DNA vectors containing a T7 autogene", Nuclei Acids Research, Apr. 29, 1994, vol. 22, No. 11, pp. 2114-2120.

Chen et al., "Genomic organization and regulation of the human orexin (hypocretin) receptor 2 gene: identification of alternative promoters", Biochemical J., Feb. 15, 2010, vol. 427, pp. 377-390.

Chen et al., "High-Efficiency Transformation of Mammalian Cells by Plasmid DNA", Molecular and Cellular biology, Aug. 1987, vol. 7, No. 8, pp. 2745-2752.

Chiapparino et al., "Genotyping single nucleotide polymorphisms in barley by tetra-primer ARMS-PCR", Genome, vol. 47(2), 2004, p. 414-420.

Chollet et al., "Biotin-labeled synthetic oligodeoxyribonucleotides: chemical synthesis and uses as hybridization probes", Nucl. Acids Res., vol. 13, No. 5, Feb. 15, 1985, p. 1529-1541.

Chu et al., "SV40 DNA transfection of cells in suspension: analysis of the efficiency of transcription and translation of T-antigen", Gene, 1981, vol. 13, pp. 197-202.

Kaneda et al., "Increased Expression of DNA Cointroduced with Nuclear Protein in Adult Rat Liver", Science Reports, Jan. 20, 1989, vol. 243, pp. 375-378.

Kappel et al., "Quantification of coagulation vactor XIII activity by a thio-NADH based assay using factor XIII immuno-depleted plasma as a diluent for calibration", Clin. Chem. Lab. Med., Sep. 10, 2010, vol. 48, No. 12, pp. 1739-1743.

Karger et al., "Multiwavelength fluorescence detection for DNA sequencing using capillary electrophoresis", Nucl. Acids Res., Jul. 29, 1991, vol. 19, No. 18, pp. 4955-4962.

Kato et al., "Expression of Hepatitis B Virus Surface Antigen in Adult Rate Liver", The Journal of Biological Chemistry, Feb. 25, 1991, vol. 266, No. 6, pp. 3361-3364.

King et al., "Pathway analysis of coronary atherosclerosis", Physiological Genomics, Jun. 7, 2005, vol. 23, p. 103-118.

Kirchgessner et al., "Orexin Synthesis and Response in the Gut", Neuron, vol. 24, 1999, p. 941-951.

Klein et al., "High-velocity microprojectiles for delivering nucleic acids into living cells", Nature, May 7, 1987, vol. 327, pp. 70-73.

Konno et al., T. , "Genetics of Hypertrophic Cardiomyopathy", Curr Opin Cardial, May 2010, vol. 35, No. 3, pp. 1-8; abstract; p. 4, paragraph 2.

Kotin, "Prospects for the Use of Adeno-Associated Virus as a Vector for Human Gene Therapy", Human Gene Therapy, Mar. 18, 1994, vol. 5, pp. 793-801.

Kurreck et al., "Design of antisense oligonucleotides stabilized by locked nucleic acids", Nucleic Acids Research, Mar. 5, 2002, vol. 30, No. 9, pp. 1911-1918.

Kwok et al., "Detection of Single Nucleotide Polymorphisms", Curr Issues Mol. Biol., 2003, vol. 5, p. 43-60.

Laframboise, "Single nucleotide polymorphism arrays: a decade of biological, computational and technological advances", Nuc. Acids Res., Jul. 1, 2009, vol. 37, No. 13, p. 4181-4193.

Lan et al., "Abnormal Calcium Handling Properties Underlie Familial Hypertrophic Cardiomyopathy Pathology in Patient-specific Induced Pluripotent Stem Cells", Cell Stem Cell. Jan. 3, 2013, vol. 12, No. 1, pp. 101-113; doi:10.1016/j.stem.2012.10.010.

Langfelder et al., "Defining clusters from a hierarchical cluster tree: the Dynamic Tree Cut package for R", Bioinformatics. 2008, vol. 24, No. 5, pp. 719-720.

Larsen et al., "Microarray-Based RNA Profiling of Breast Cancer: Batch Effect Removal Improves Cross-Platform Consistency", BioMed Research International, Jul. 3, 2014, vol. 2014, Article ID 651751, 11 pgs.

Larson et al., "Framingham Heart Study 100K project: genome-wide associations for cardiovascular disease outcomes", BMC Medical Genetics 8, Sep. 19, 2007, Suppl. 1:S5, 9 pgs.

Lebkowski et al., "Adeno-Associated Virus: A Vector system for Efficient Introduction and Integration of DNA into a Variety of Mammalian Cell Types", Molecular and Cellular Biology, Oct. 1988, vol. 8, No. 10, pp. 3988-3996.

Lee et al., "Association of Parental Heart Failure with Risk of Heart Failure in Offspring", N. Engl. J. Med., Jul. 13, 2006, vol. 355, pp. 138-147.

Lee et al., "Vita Blue: A New 633-nm Excitable Fluorescent Dye for Cell Analysis", Cytometry, 1989, vol. 10, pp. 151-164.

Li et al., et al., "Molecular beacons an optimal multifunctional biological probe", Biochemical and Biophysical Research Communications, May 19, 2008, vol. 373, pp. 457-461.

Liggett et al., "A GRK5 Polymorphism that Inhibits ß-Adrenergic Receptor Signaling is Protective in Heart Failure", Nature Medicine, May 2008, vol. 14, p. 510-517.

Lilleberg, "In-depth mutation and SNP discovery using DHPLC gene scanning", Current Opinion in Drug Discovery and Development., 2003, vol. 6, No. 2, pp. 237-252.

Lin et al., "The Sleep Disorder Canine Narcolepsy is Caused by a Mutation in the Hypocretin (Orexin) Receptor 2 Gene", Cell, Aug. 6, 1999, vol. 98, p. 365-376.

Lloyd-Jones et al., "Heart Disease and Stroke Statistics—2010 Update", Circulation, vol. 121, 2010, p. e46-e215 (presented in two parts).

Lois et al., "Germline Transmission and Tissue-Specific Expression of Transgenes Delivered by Lentiviral Vectors", Science, Feb. 1, 2002, vol. 295, pp. 868-872.

Lopez et al., "Orexin Receptors and Expressed in the Adrenal Medulla of the Rat", Endocrinology, 1999, vol. 140, No. 12, p. 5991-5994.

Lowe et al., "Multiplex Single Nucleotide Polymorphism Genotyping Utilizing Ligase Detection Reaction Coupled Surface Enhanced Raman Spectroscopy", Anal Chem., Jul. 1, 2010, vol. 82, No. 13, p. 5810-5814.

Lubkin et al., "Independent Feeding and Metabolic Actions of Orexins in Mice", Biochemical and Biophysical Research Communications, Oct. 26, 1998, vol. 253, pp. 241-245.

Lundstrom, "Latest development in viral vectors for gene therapy", Trends in Biotechnology, Mar. 2003, vol. 21, No. 3, pp. 117-122.

Matsumura et al., "Central Orexin-A Augments Sympathoadrenal Outflow in Conscious Rabbits", Hypertension, vol. 37, 2001, p. 1382-1387.

Matthews et al., "Review: Analytical Strategies for the Use of DNA Probes", Analytical Biochemistry, 1988, vol. 169, pp. 1-25.

Meder et al., "A Genome-wide association study identifies 6p21 as novel risk locus for dilated cardiomyopathy", Eur. Heart J., vol. 35, 2014, p. 1069-1077.

Michael et al., "Binding-incompetent Adenovirus Facilitates Molecular Conjugate-mediated Gene Transfer by the Receptor-mediated Endocytosis Pathway", The Journal of Biological Chemistry, Apr. 5, 1993, vol. 268, No. 10, pp. 6866-6869.

(56) References Cited

OTHER PUBLICATIONS

Miller, "Progress Toward Human Gene Therapy", The American Society of Hematology, Jul. 15, 1990, vol. 76, No. 2, pp. 271-278.

Miller et al., "Improved Retroviral Vectors for Gene Transfer and Expression", BioTechniques, Oct. 1989, vol. 7, No. 9, pp. 980-990.

Mittereder et al., "Evaluation of the Efficacy and Safety of In Vitro, Adenovirus-Mediated Transfer of Human Cystic Fibrosis Transmembrane Conductance Regulator cDNA", Human Gene Therapy, Mar. 2, 1994, vol. 5, pp. 717-729.

Mochizuki et al., "Orexin receptor 2 expression in the posterior hypothalamus rescues sleepiness in narcoleptic mice", Proc. Natl. Acad. Sci. U.S.A., vol. 108, Feb. 4, 2011, p. 4471-4476.

Morlan et al., "Mutation Detection by Real-Time PCR: A Simple, Robust and Highly Selective Method", PLoS one, Feb. 25, 2009, vol. 4, Issue 2, pp. e4584-1-e4584-11.

Morrison et al., "Labeling Fluorescence In Situ Hybridization Probes for Genomic Targets", Molecular Cytogenetics: Protocols and Applications, 2002, pp. 21-40.

Muñoz et al., "Tetra Primer ARMS-PCR for identification of SNB in ß-tubulin of Botrytis cinerea, responsible of resistance to benzimidazole", Journal of Microbiological Methods., Jun. 17, 2009, vol. 78, p. 245-246.

Muzyczka, "Use of Adeno-Associated Viruses as a General Transduction Vector of Mammalian Cells", Current Topics in Microbiology and Immunology, 1992, vol. 158, pp. 97-129; printed Dec. 5, 2016 from http://link.springer.com/chapter/10.1007/978-3-642-75608.5.

Narang et al., "Improved Phosphotriester Method for the Synthesis of Gene Fragments", Methods in Enzymology, 1979, vol. 68, pp. 90-98.

Nicolau et al., "Liposomes as Carriers for in Vivo Gene Transfer and Expression", Methods in Enzymology, 1987, vol. 149, pp. 157-176.

Obika et al., "Stability and structural features of the duplexes containing nucleoside analogues with a fixed N-type conformation, 1'-O,4'C-methyleneribonucleosides", Tetrahedron Letters, May 22, 1998, vol. 39, pp. 5401-5404.

Olivier, "The Invader assay for SNP genotyping", Mutation Research, Jun. 3, 2005, vol. 573, No. 1-2, pp. 103-110.

International Preliminary Report on Patentability for International Application PCT/US2014/065519, dated May 17, 2016, 10 pgs.

METHODS OF TREATING HEART FAILURE WITH AGONISTS OF HYPOCRETIN RECEPTOR 2

TECHNICAL FIELD

The present invention pertains to methods of treating heart failure. In particular, the invention relates to methods of treating individuals for heart failure with agonists of hypocretin receptor 2. The invention further relates to the use of genetic analysis of the single nucleotide polymorphism rs7767652, which resides immediately upstream of the HCRTR2 gene, to identify individuals in need of treatment for heart failure who are predicted to be more responsive to medical intervention.

BACKGROUND

Heart failure, a syndrome characterized by impaired cardiac function, affects over five million people in the United States alone. As the most common admitting diagnosis for patients over 65, heart failure portends a worse prognosis than most cancers (Lloyd-Jones et al. (2010) Circulation 121:e46-e215). With the aging population, it is expected to affect 3.5% of the US population over the next 20 years (Heidenreich et al. (2012) Circulation 123:933-944).

Heart failure is the result of a wide variety of underlying conditions, most commonly coronary artery disease and hypertension (Ho et al. (1993) J. Am. Coll. Cardiol. 22:6A-13A), and can be associated with preserved or reduced left ventricular ejection fraction. Some patients in the low ejection fraction group exhibit a dramatic improvement with optimal medical therapy, which includes treatment with β-adrenergic receptor antagonists and inhibitors of the renin-angiotensin-aldosterone system. Why some patients have a dramatic response to pharmaceutical therapy whereas others decompensate and require transplantation is not well understood.

Candidate gene studies with targeted genotyping of common variants in ADRB1 and GRK5 members of the β-adrenergic receptor signaling pathway have shown associations with long-term heart-failure survival (Cresci et al. (2009) J. Am. Coll. Cardiol. 54:432-444; Liggett et al. (2008) Nature Medicine 14:510-517). Studies with more comprehensive genotyping of cardiovascular gene candidates identified associations between common variants in HSPB7 and FRMD4B and dilated cardiomyopathy (Stark et al. (2010) PLoS Genetics 6:e1001167) or advanced heart failure (Cappola et al. (2010) Circ. Cardiovasc. Genet. 3:147-154). In the limited number of genome-wide studies of heart failure performed (Larson et al. (2007) BMC Medical Genetics 8 Suppl. 1:S5; Smith et al. (2010) Circ. Cardiovasc. Genet. 3:256-266; Villard et al. (2011) Eur. Heart J. 32:1065-1076), the common genomic variants that have reached genome-wide significance have not been replicated in large cohorts. Genome-wide studies of improvement in left ventricular function in response to medical intervention have yet to be performed.

There remains a need for an improved therapy for patients suffering from heart failure and diagnostic biomarkers that can be used to identify patients likely to have a favorable response to medical intervention.

SUMMARY OF THE INVENTION

The present invention relates to methods of treating individuals for heart failure with agonists of hypocretin receptor 2. The invention further relates to the use of genetic analysis of the single nucleotide polymorphism rs7767652, which resides immediately upstream of the HCRTR2 gene, to identify individuals in need of treatment for heart failure who are predicted to be more responsive to medical intervention.

In one aspect, the invention includes a method for treating an individual for heart failure, the method comprising administering a therapeutically effective amount of a composition comprising at least one agonist of hypocretin receptor 2 to the individual. In one embodiment, the individual is human. The individual may also be diabetic or hypertensive.

Agonists of hypocretin receptor 2 that can be used in the practice of the invention include, but are not limited to orexin-A, orexin-B, [Ala11,D-Leu15]-orexin B, and SB-668875. In one embodiment the agonist of hypocretin receptor 2 is an orexin mimic. The agonist of hypocretin receptor 2 can be recombinantly or synthetically produced. Compositions comprising one or more agonists of hypocretin receptor 2 may be administered by any suitable method, including, but not limited to, intravenously, intra-arterially, subcutaneously, intracerebroventricularly, intrathecally, or intranasally. In one embodiment, compositions are administered into the brain or spinal cord of the individual. In one embodiment, compositions are administered locally into the cisterna magna or the rostral ventrolateral medulla.

A therapeutically effective amount of an agonist of hypocretin receptor 2 can be administered to an individual in one or more administrations, applications or dosages. By "therapeutically effective dose or amount" of an agonist of hypocretin receptor 2 is intended an amount that, when administered, as described herein, brings about a positive therapeutic response, such as improved left ventricular function or survival of an individual treated for heart failure.

In certain embodiments, the agonist of hypocretin receptor 2 is administered according to a daily dosing regimen, such as a twice-a-week or three-times-a-week dosing regimen. Multiple cycles of the method of treatment may be administered to an individual for a time period sufficient to effect at least a partial recovery of heart function, such as a 10% or greater increase or improvement in left ventricular function (e.g., as measured by ejection fraction). Arterial blood pressure or heart rate may also be increased in the individual after administering the agonist of hypocretin receptor 2.

In certain embodiments, the method further comprises treatment with one or more other agents for treating heart failure such as, but not limited to an angiotensin converting enzyme (ACE) inhibitor, an angiotensin II receptor blocker (ARB), a beta-blocker, digoxin, a diuretic, a blood vessel dilator, potassium, magnesium, an aldactone inhibitor, a calcium channel blocker, and an inotrope.

In another aspect, the invention includes a method for enhancing cardiovascular function of an individual with heart failure, the method comprising administering an effective amount of an agonist of hypocretin receptor 2 to the individual. Enhancing cardiovascular function may include, for example, a 10% or greater increase or improvement in left ventricular function (e.g., as measured by ejection fraction), and/or increased arterial blood pressure, and/or increased heart rate.

In another aspect, the invention includes a composition comprising an agonist of hypocretin receptor 2 for use in the treatment of heart failure. In certain embodiments, the agonist of hypocretin receptor 2 is selected from the group consisting of orexin-A, orexin-B, [Ala11,D-Leu15]-orexin B, and SB-668875.

In another aspect, the invention includes a composition comprising an agonist of hypocretin receptor 2 for use in enhancing cardiovascular function. In certain embodiments, the agonist of hypocretin receptor 2 is selected from the group consisting of orexin-A, orexin-B, [Ala11,D-Leu15]-orexin B, and SB-668875.

In another aspect, the invention includes the use of an agonist of hypocretin receptor 2 in the manufacture of a medicament for treating an individual for heart failure. In certain embodiments, the agonist of hypocretin receptor 2 is selected from the group consisting of orexin-A, orexin-B, [Ala11,D-Leu15]-orexin B, and SB-668875.

In another aspect the invention includes a diagnostic method for predicting therapeutic responsiveness to treatment with a beta blocker or an ACE inhibitor for an individual with heart failure, the method comprising determining which allele is present at single nucleotide polymorphism rs7767652 in the individual, wherein the presence of the major allele at the single nucleotide polymorphism rs7767652 indicates that the individual will be more responsive to treatment for heart failure with a beta blocker or an ACE inhibitor than an individual with the minor allele at the single nucleotide polymorphism rs7767652.

These and other embodiments of the subject invention will readily occur to those of skill in the art in view of the disclosure herein.

BRIEF DESCRIPTION OF THE DRAWINGS

FIG. 2A shows SNPs plotted on the x axis according to their position on each chromosome against association with greater than 10% improvement in ejection fraction on the y axis (shown as $-\log_{10}P$). The gray horizontal line represents the threshold for Bonferroni-adjusted significance ($p<3.6\times10^{-5}$). The locus near HCRTR2 reached an association significance of $P=3.29\times10^{-5}$ in the Phase II analysis. FIG. 2B shows an LD map ($r^2$) of the region surrounding rs7767652 (boxed) drawn according to Phase II HapMap (release 26) CEU individuals. All SNPs are shaded according to the pairwise $r^2$ value.

FIG. 3A shows a diagram of the luciferase reporter with the rs7767652 locus, which contains a TCF-4 binding site. This SNP with its flanking sequence was inserted into the multiple cloning site (MCS) of a pLuc-MCS vector, which is driven by a minimal promoter upstream from the luciferase gene. FIG. 3B shows allele-specific luciferase reporter assays at rs7767652 in C2C12 cells. The reporter construct carrying the minor allele (rs776 T-Luc) had slightly lower activity at baseline compared to the construct with the major allele (rs776 C-Luc). The major allele was highly responsive to β-catenin/TCF4 overexpression, whereas the minor allele disrupted β-catenin/TCF4 mediated transactivation. The TCF4 transactivation mutant (TCF4Δ30) blocked β-catenin effects. FIG. 3C shows human HCRTR2 gene expression measurements from microarray experiments in myocardial tissue of patients with dilated cardiomyopathy (DCM, n=162), ischemic cardiomyopathy (ICM, n=143) and controls (n=45) obtained from the Gene Expression Omnibus (GEO) repository. Gene expression values were graphed as mean fluorescence intensity ratios with 95% confidence intervals normalized across experiments. HCRTR2 expression is higher in DCM tissue compared to controls (* p=0.00017) and is higher in ICM tissue compared to controls (** p=0.000044). FIG. 3D shows diastolic function in C57BL/6 wild-type (n=11) and HCRTR2 transcription deficient (TD) mice (n=10). The HCRTR2 TD mice had worse diastolic function as measured by a higher E/E' ratio compared to the wild-type mice (p=0.05). FIG. 3E shows systolic function in C57BL/6 wild-type (n=11) and HCRTR2 transcription deficient (TD) mice (n=10). There were no significant differences in ejection fraction between the two sets of mice (p=0.94). FIG. 3F shows changes in exercise capacity before and after treatment with angiotensin II+isoproterenol chemical stress in C57BL/6 wild-type (n=8) compared to HCRTR2 TD (n=8) mice. The HCRTR2 TD mice had a smaller improvement in peak VO$_2$ (13.0 ml/kg/min+/−3.0 vs. 4.2 ml/kg/min+/−2.2, p=0.032) after 2 weeks of chemical stress. FIG. 3G shows representative examples of trichrome-stained myocardial sections from five C57BL/6 wild type (left) and five HCRTR2 TD (right) mice after 2 weeks of angiotensin II+isoproterenol chemical stress. The HCRTR2 TD mouse hearts had greater degree of trichrome stain (blue/red ratio 0.82+/−0.1 vs. 0.85+/−0.01, p=0.022). FIG. 3H shows systolic function in WT mice infused with either saline (n=6) or orexin A (n=7) for 4 weeks and stressed with angiotensin II+isoproterenol infusion during the latter 2 weeks. Mice that underwent infusion with orexin A had better systolic function after chemical stress at week 4 compared to those infused with saline (Ejection Fraction 56.6%+/−4.5% vs. 43.6%+/−3.3%, * p=0.045).

DETAILED DESCRIPTION OF THE INVENTION

Figure 1:
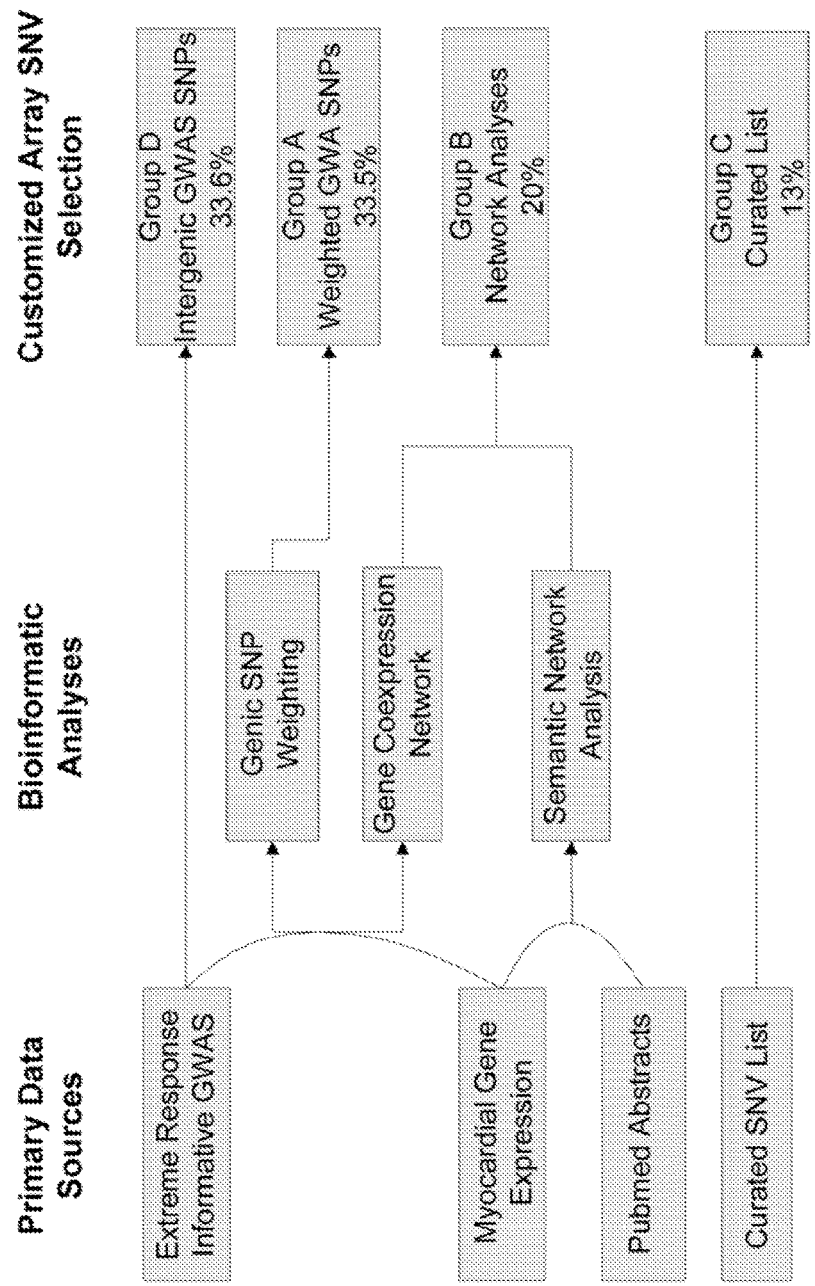
FIG. 1 shows the primary data sources and bioinformatic analyses used for SNV selection for the custom array. Approximately one third of the 1536 SNVs were derived from the gene expression-weighted analysis of an extreme response genome-wide association study (GWAS), one third from the most statistically significant intergenic SNPs from the extreme response GWAS, and one third from the GWAS-informed analyses of gene-coexpression networks, semantic literature networks or a curated set of SNPs manually selected from the literature.

The practice of the present invention will employ, unless otherwise indicated, conventional methods of genetics, chemistry, biochemistry, molecular biology and recombinant DNA techniques, within the skill of the art. Such techniques are explained fully in the literature. See, e.g., *Single Nucleotide Polymorphisms: Methods and Protocols* (Methods in Molecular Biology, A. A. Komar ed., Humana Press; $2^{nd}$ edition, 2009); *Genetic Variation: Methods and Protocols* (Methods in Molecular Biology, M. R. Barnes and G. Breen eds., Humana Press, 2010); *Handbook of Experimental Immunology*, Vols. I-IV (D. M. Weir and C. C. Blackwell eds., Blackwell Scientific Publications); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.).

All publications, patents and patent applications cited herein, whether supra or infra, are hereby incorporated by reference in their entireties.

I. DEFINITIONS

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "an agonist" includes a mixture of two or more such agonists, and the like.

By "therapeutically effective dose or amount" of an agonist of hypocretin receptor 2 is intended an amount that, when administered as described herein, brings about a positive therapeutic response, such as improved left ventricular function or survival of a subject treated for heart failure.

The term "partial response" (PR) as used herein means a 10% or greater increase or improvement in left ventricular function (e.g., as measured by ejection fraction).

The term "survival" as used herein means the time from the first dose of an agonist of hypocretin receptor 2 to the time of death.

The terms "hybridize" and "hybridization" refer to the formation of complexes between nucleotide sequences which are sufficiently complementary to form complexes via Watson Crick base pairing. The terms are intended to refer to the formation of a specific hybrid between a probe and a target region.

The term "derived from" is used herein to identify the original source of a molecule but is not meant to limit the method by which the molecule is made which can be, for example, by chemical synthesis or recombinant means.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

"Substantially purified" generally refers to isolation of a substance (compound, polynucleotide, oligonucleotide, protein, or polypeptide) such that the substance comprises the majority percent of the sample in which it resides. Typically in a sample, a substantially purified component comprises 50%, preferably 80%-85%, more preferably 90-95% of the sample. Techniques for purifying polynucleotides oligonucleotides and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism with which the molecule is found in nature or is present in the substantial absence of other biological macro molecules of the same type. The term "isolated" with respect to a polynucleotide or oligonucleotide is a nucleic acid molecule devoid, in whole or part, of sequences normally associated with it in nature; or a sequence, as it exists in nature, but having heterologous sequences in association therewith; or a molecule disassociated from the chromosome.

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms will be used interchangeably. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. The term also includes locked nucleic acids (e.g., comprising a ribonucleotide that has a methylene bridge between the 2'-oxygen atom and the 4'-carbon atom). See, for example, Kurreck et al. (2002) Nucleic Acids Res. 30: 1911-1918; Elayadi et al. (2001) Curr. Opinion Invest. Drugs 2: 558-561; Orum et al. (2001) Curr. Opinion Mol. Ther. 3: 239-243; Koshkin et al. (1998) Tetrahedron 54: 3607-3630; Obika et al. (1998) Tetrahedron Lett. 39: 5401-5404.

The terms "polymorphism," "polymorphic nucleotide," "polymorphic site" or "polymorphic nucleotide position" refer to a position in a nucleic acid that possesses the quality or character of occurring in several different forms. A nucleic acid may be naturally or non-naturally polymorphic, e.g., having one or more sequence differences (e.g., additions, deletions and/or substitutions) as compared to a reference sequence. A reference sequence may be based on publicly available information (e.g., the U.C. Santa Cruz Human Genome Browser Gateway (genome.ucsc.edu/cgi-bin/hgGateway) or the NCBI website (ncbi.nlm.nih.gov)) or may be determined by a practitioner of the present invention using methods well known in the art (e.g., by sequencing a reference nucleic acid). A nucleic acid polymorphism is characterized by two or more "alleles," or versions of the nucleic acid sequence. Typically, an allele of a polymorphism that is identical to a reference sequence is referred to as a "reference allele" and an allele of a polymorphism that is different from a reference sequence is referred to as an "alternate allele," or sometimes a "variant allele". As used herein, the term "major allele" refers to the more frequently occurring allele at a given polymorphic site, and "minor allele" refers to the less frequently occurring allele, as present in the general or study population.

The term "single nucleotide polymorphism" or "SNP" refers to a polymorphic site occupied by a single nucleotide, which is the site of variation between allelic sequences. The site is usually preceded by and followed by highly conserved sequences of the allele (e.g., sequences that vary in less than $\frac{1}{100}$ or $\frac{1}{1000}$ members of the populations). A single nucleotide polymorphism usually arises due to substitution of one nucleotide for another at the polymorphic site. Single nucleotide polymorphisms can also arise from a deletion of a nucleotide or an insertion of a nucleotide relative to a reference allele.

The HUGO Gene Nomenclature Committee (HGNC) has assigned unique gene symbols and names to more than 31,000 human loci, of which over 19,000 are protein coding. Genenames.org is a curated online repository of HGNC-approved gene nomenclature, and those gene names are used herein.

SNPs generally are described as having a minor allele frequency, which can vary between populations, but generally refers to the sequence variation (A,T,G, or C) that is less common than the major allele. The frequency can be obtained from dbSNP or other sources, or may be determined for a certain population using Hardy-Weinberg equilibrium (See for details see Eberle M A, Rieder M J, Kruglyak L, Nickerson D A (2006) Allele Frequency Matching Between SNPs Reveals an Excess of Linkage Disequilibrium in Genic Regions of the Human Genome. PLoS Genet 2(9): e142. doi:10.1371/journal.pgen.0020142; herein incorporated by reference).

SNPs described here are further detailed at the NCBI dbSNP, found online at ncbi.nlm.nih.gov/projects/SNP, from which the following brief descriptions are taken. Population data on these SNPs may be found at this site. The SNP representations are according to NCBI dbSNP convention, with the two alleles between brackets.

The term "rs7767652," as used herein, refers to the SNP at position 27 (indicated by the [C/T]) of the following sequence upstream of the HCRTR2 gene: GTTGATAAAAT-ATTCCACATTATAAT [C/T]AAAGAAAGTA-CAAAAAAGTTA AATG (SEQ ID NO:1). This SNP has global minor allele frequency (MAF)/MinorAlleleCount of T=0.1837/400, as reported in the NCBI dbSNP.

As used herein, the term "probe" or "oligonucleotide probe" refers to a polynucleotide, as defined above, that contains a nucleic acid sequence complementary to a nucleic acid sequence present in the target nucleic acid analyte (e.g., at SNP location). The polynucleotide regions of probes may be composed of DNA, and/or RNA, and/or synthetic nucleotide analogs. Probes may be labeled in order to detect the target sequence. Such a label may be present at the 5' end, at the 3' end, at both the 5' and 3' ends, and/or internally.

An "allele-specific probe" hybridizes to only one of the possible alleles of a SNP under suitably stringent hybridization conditions.

The term "primer" or "oligonucleotide primer" as used herein, refers to an oligonucleotide that hybridizes to the template strand of a nucleic acid and initiates synthesis of a nucleic acid strand complementary to the template strand when placed under conditions in which synthesis of a primer extension product is induced, i.e., in the presence of nucleotides and a polymerization-inducing agent such as a DNA or RNA polymerase and at suitable temperature, pH, metal concentration, and salt concentration. The primer is preferably single-stranded for maximum efficiency in amplification, but may alternatively be double-stranded. If double-stranded, the primer can first be treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA or RNA synthesis. Typically, nucleic acids are amplified using at least one set of oligonucleotide primers comprising at least one forward primer and at least one reverse primer capable of hybridizing to regions of a nucleic acid flanking the portion of the nucleic acid to be amplified.

An "allele-specific primer" matches the sequence exactly of only one of the possible alleles of a SNP, hybridizes at the SNP location, and amplifies only one specific allele if it is present in a nucleic acid amplification reaction.

The term "amplicon" refers to the amplified nucleic acid product of a PCR reaction or other nucleic acid amplification process (e.g., ligase chain reaction (LGR), nucleic acid sequence based amplification (NASBA), transcription-mediated amplification (TMA), Q-beta amplification, strand displacement amplification, or target mediated amplification). Amplicons may comprise RNA or DNA depending on the technique used for amplification. For example, DNA amplicons may be generated by RT-PCR, whereas RNA amplicons may be generated by TMA/NASBA.

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, semiconductor nanoparticles, dyes, metal ions, metal sols, ligands (e.g., biotin, streptavidin or haptens) and the like. The term "fluorescer" refers to a substance or a portion thereof which is capable of exhibiting fluorescence in the detectable range. Particular examples of labels which may be used in the practice of the invention include, but are not limited to, horseradish peroxidase (HRP), SYBR® green, SYBR® gold, fluorescein, carboxyfluorescein (FAM), Alexa Fluor dyes, Cy3, Cy5, Cy7, 7-amino-4-methylcoumarin-3-acetic acid (AMCA), 5-(and-6)-carboxy-X-rhodamine, lissamine rhodamine, fluorescein-5-isothiocyanate (FITC), 7-diethylaminocoumarin-3-carboxylic acid, tetramethylrhodamine-5-(and-6)-isothiocyanate, 5-(and-6)-carboxytetramethylrhodamine, 7-hydroxycoumarin-3-carboxylic acid, 6-[fluorescein 5-(and-6)-carboxamido]hexanoic acid, N-(4,4-difluoro-5,7-dimethyl-4-bora-3a,4a diaza-3-indacenepropionic acid, eosin-5-isothiocyanate; erythrosine-5-isothiocyanate, 5-(and-6)-carboxyrhodamine 6G, CASCADE blue aectylazide, CAL Fluor Orange 560, CAL Fluor Red 610, Quasar Blue 670, tetramethyl rhodamine (TAMRA), 2',4',5',7'-tetrachloro-4-7-dichlorofluorescein (TET), rhodamine, dansyl, umbelliferone, dimethyl acridinium ester (DMAE), Texas red, Pacific Blue, Pacific Orange, quantum dots, luminol, NADPH, and α-β-galactosidase.

The term "biological sample," as used herein, includes any cell, tissue, or bodily fluid comprising nucleic acids (e.g., genomic DNA or RNA) such as, but not limited to, blood, saliva, cells from buccal swabbing, skin, hair, biopsies of organs, amniotic fluid, various other tissues, and the like.

The terms "subject," "individual," and "patient," are used interchangeably herein and refer to any mammalian subject, particularly humans. Other subjects may include cattle, dogs, cats, guinea pigs, rabbits, rats, mice, horses, and so on. In some cases, the methods of the invention find use in experimental animals, in veterinary application, and in the development of animal models, including, but not limited to, rodents including mice, rats, and hamsters; and primates.

II. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based on the discovery of a novel therapeutic methodology for effectively treating heart failure using an agonist of hypocretin receptor 2 (see Example 1). Additionally, the inventors have shown that patients having the major allele at the single nucleotide polymorphism rs7767652, which is located immediately upstream of the hypocretin receptor 2 (HCRTR2) gene, show significantly greater improvement in left ventricular function (e.g., at least a 10% improvement in ejection fraction) with treatment with beta blockers or ACE inhibitors than patients having the minor allele at rs7767652 (e.g., less than a 10% improvement in ejection fraction).

In order to further an understanding of the invention, a more detailed discussion is provided below regarding methods of treating subjects for heart failure.

A. Administration of an Agonist of Hypocretin Receptor 2

One or more agonists of hypocretin receptor 2 may be administered to an individual in need of treatment for heart failure. Exemplary agonists that can be used in the practice of the invention include orexin-A, orexin-B, [Ala11,D-Leu15]-orexin B, and SB-668875. In one embodiment, the agonist is an orexin mimic. The agonist may be recombinantly or synthetically produced.

At least one therapeutically effective cycle of treatment with an agonist of hypocretin receptor 2 will be administered to a subject for treatment of heart failure. By "therapeutically effective cycle of treatment" is intended a cycle of treatment that when administered, brings about a positive therapeutic response with respect to treatment of an individual for heart failure. Of particular interest is a cycle of treatment with an agonist of hypocretin receptor 2 that improves heart function or survival of a subject treated for heart failure. By "positive therapeutic response" is intended that the individual undergoing treatment according to the invention exhibits an improvement in one or more symptoms of heart failure, such as improved left ventricular function, increased blood pressure, or increased exercise capacity.

In certain embodiments, multiple therapeutically effective doses of compositions comprising one or more agonists of hypocretin receptor 2 and/or one or more other therapeutic agents, such as other drugs for treating heart failure will be administered. The compositions are typically, although not necessarily, administered orally, via injection (subcutaneously, intravenously, or intramuscularly), by infusion, or locally. Additional modes of administration are also contemplated, such as intracerebroventricular, intrathecal, intracerebral, intraspinal, intranasal, intraparenchymatous, pulmonary, rectal, transdermal, transmucosal, pericardial, intra-arterial, intraocular, intraperitoneal, and so forth.

The preparations according to the invention are also suitable for local treatment. For example, compositions may be administered directly by stereotactic injection into the brain. The particular preparation and appropriate method of administration are chosen to target an agonist to the hypocretin receptor 2 receptors in the brain. In particular embodiments, compositions are administered into the brain or spinal cord of a subject. In one embodiment, a composition is administered into the cisterna magna or the rostral ventrolateral medulla of a subject.

The pharmaceutical preparation can be in the form of a liquid solution or suspension immediately prior to administration, but may also take another form such as a syrup, cream, ointment, tablet, capsule, powder, gel, matrix, suppository, or the like. The pharmaceutical compositions comprising one or more agonists of hypocretin receptor 2 and other agents may be administered using the same or different routes of administration in accordance with any medically acceptable method known in the art.

In another embodiment of the invention, the pharmaceutical compositions comprising one or more agonists of hypocretin receptor 2 and/or other agents are in a sustained-release formulation, or a formulation that is administered using a sustained-release device. Such devices are well known in the art, and include, for example, transdermal patches, and miniature implantable pumps that can provide for drug delivery over time in a continuous, steady-state fashion at a variety of doses to achieve a sustained-release effect with a non-sustained-release pharmaceutical composition.

The invention also provides a method for administering a conjugate comprising an agonist of hypocretin receptor 2 to a patient suffering from a condition that is responsive to treatment with an agonist of hypocretin receptor 2 contained in the conjugate or composition. The method comprises administering, via any of the herein described modes, a therapeutically effective amount of the conjugate or drug delivery system, preferably provided as part of a pharmaceutical composition. The method of administering may be used to treat any condition that is responsive to treatment with an agonist of hypocretin receptor 2. More specifically, the compositions herein are effective in treating heart failure.

Those of ordinary skill in the art will appreciate which conditions a specific agonist of hypocretin receptor 2 can effectively treat. The actual dose to be administered will vary depending upon the age, weight, and general condition of the subject as well as the severity of the condition being treated, the judgment of the health care professional, and conjugate being administered. Therapeutically effective amounts can be determined by those skilled in the art, and will be adjusted to the particular requirements of each particular case.

Generally, a therapeutically effective amount will range from about 0.50 mg to 5 grams of an agonist of hypocretin receptor 2 inhibitor daily, more preferably from about 5 mg to 2 grams daily, even more preferably from about 7 mg to 1.5 grams daily. Preferably, such doses are in the range of 10-600 mg four times a day (QID), 200-500 mg QID, 25-600 mg three times a day (TID), 25-50 mg TID, 50-100 mg TID, 50-200 mg TID, 300-600 mg TID, 200-400 mg TID, 200-600 mg TID, 100 to 700 mg twice daily (BID), 100-600 mg BID, 200-500 mg BID, or 200-300 mg BID. The amount of compound administered will depend on the potency of the specific agonist of hypocretin receptor 2 and the magnitude or effect on heart function desired and the route of administration.

A purified agonist of hypocretin receptor 2 (again, preferably provided as part of a pharmaceutical preparation) can be administered alone or in combination with one or more other therapeutic agents, such as an angiotensin converting enzyme (ACE) inhibitor, an angiotensin II receptor blocker (ARB), a beta-blocker, digoxin, a diuretic, a blood vessel dilator, potassium, magnesium, an aldactone inhibitor, a calcium channel blocker, or an inotrope, or other medications used to treat a particular condition or disease according to a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Preferred compositions are those requiring dosing no more than once a day.

An agonist of hypocretin receptor 2 can be administered prior to, concurrent with, or subsequent to other agents. If provided at the same time as other agents, one or more agonists of hypocretin receptor 2 can be provided in the same or in a different composition. Thus, one or more agonists of hypocretin receptor 2 and other agents can be presented to the individual by way of concurrent therapy. By "concurrent therapy" is intended administration to a subject such that the therapeutic effect of the combination of the substances is caused in the subject undergoing therapy. For example, concurrent therapy may be achieved by administering a dose of a pharmaceutical composition comprising an agonist of hypocretin receptor 2 and a dose of a pharmaceutical composition comprising at least one other agent, such as another agonist of hypocretin receptor 2 or drug for treating heart failure, which in combination comprise a therapeutically effective dose, according to a particular dosing regimen. Similarly, one or more agonists of hypocretin receptor 2 and one or more other therapeutic agents can be administered in at least one therapeutic dose. Administration of the separate pharmaceutical compositions can be performed simultaneously or at different times (i.e., sequentially, in either order, on the same day, or on different days), as long as the therapeutic effect of the combination of these substances is caused in the subject undergoing therapy.

B. Detecting and Genotyping Gene Polymorphisms

The SNP rs7767652, which is located upstream of the HCRTR2 gene, can be used as a genetic marker for determining whether an individual with heart failure is likely to respond more favorably to medical intervention, such as treatment with a beta blocker or an ACE inhibitor. The major allele of rs7767652 has a C and the minor allele of rs7767652 has a T at position 27 (indicated by the [C/T]) of the following sequence:

```
                                         (SEQ ID NO: 1)
GTTGATAAAATATTCCACATTATAAT[C/T]AAAGAAAGTACAAAA
AAGTTAAATG.
```

For genetic testing, a biological sample containing nucleic acids is collected from an individual in need of treatment for heart failure. The biological sample is typically blood, saliva, or cells from buccal swabbing, but can be any sample from bodily fluids, tissue or cells that contains genomic DNA or RNA of the individual. In certain embodiments, nucleic acids from the biological sample are isolated, purified, and/or amplified prior to analysis using methods well-known in the art. See, e.g., Green and Sambrook *Molecular Cloning: A Laboratory Manual* (Cold Spring Harbor Laboratory Press; 4$^{th}$ edition, 2012); and *Current Protocols in Molecular Biology* (Ausubel ed., John Wiley & Sons, 1995); herein incorporated by reference in their entireties.

It is understood that SNPs can be detected in a sample by any suitable method known in the art. Detection of a SNP can be direct or indirect. For example, the SNP itself can be detected directly. Alternatively, the SNP can be detected indirectly from cDNAs, amplified RNAs or DNAs, or proteins expressed by the SNP. Any method that detects a single base change in a nucleic acid sample can be used. For example, allele-specific probes that specifically hybridize to a nucleic acid containing the polymorphic sequence can be used to detect SNPs. A variety of nucleic acid hybridization formats are known to those skilled in the art. For example, common formats include sandwich assays and competition or displacement assays. Hybridization techniques are generally described in Hames, and Higgins "Nucleic Acid Hybridization, A Practical Approach," IRL Press (1985); Gall and Pardue, Proc. Natl. Acad. Sci. U.S.A., 63:378-383 (1969); and John et al Nature, 223:582-587 (1969).

Sandwich assays are commercially useful hybridization assays for detecting or isolating nucleic acids. Such assays utilize a "capture" nucleic acid covalently immobilized to a solid support and a labeled "signal" nucleic acid in solution. The clinical sample will provide the target nucleic acid. The "capture" nucleic acid and "signal" nucleic acid probe hybridize with the target nucleic acid to form a "sandwich" hybridization complex.

In one embodiment, the allele-specific probe is a molecular beacon. Molecular beacons are hairpin shaped oligonucleotides with an internally quenched fluorophore. Molecular beacons typically comprise four parts: a loop of about 18-30 nucleotides, which is complementary to the target nucleic acid sequence; a stem formed by two oligonucleotide regions that are complementary to each other, each about 5 to 7 nucleotide residues in length, on either side of the loop; a fluorophore covalently attached to the 5' end of the molecular beacon, and a quencher covalently attached to the 3' end of the molecular beacon. When the beacon is in its closed hairpin conformation, the quencher resides in proximity to the fluorophore, which results in quenching of the fluorescent emission from the fluorophore. In the presence of a target nucleic acid having a region that is complementary to the strand in the molecular beacon loop, hybridization occurs resulting in the formation of a duplex between the target nucleic acid and the molecular beacon. Hybridization disrupts intramolecular interactions in the stem of the molecular beacon and causes the fluorophore and the quencher of the molecular beacon to separate resulting in a fluorescent signal from the fluorophore that indicates the presence of the target nucleic acid sequence.

For SNP detection, the molecular beacon is designed to only emit fluorescence when bound to a specific allele of a SNP. When the molecular beacon probe encounters a target sequence with as little as one non-complementary nucleotide, the molecular beacon preferentially stay in its natural hairpin state and no fluorescence is observed because the fluorophore remains quenched. See, e.g., Nguyen et al. (2011) Chemistry 17(46):13052-13058; Sato et al. (2011) Chemistry 17(41):11650-11656; Li et al. (2011) Biosens Bioelectron. 26(5):2317-2322; Guo et al. (2012) Anal. Bioanal. Chem. 402(10):3115-3125; Wang et al. (2009) Angew. Chem. Int. Ed. Engl. 48(5):856-870; and Li et al. (2008) Biochem. Biophys. Res. Commun. 373(4):457-461; herein incorporated by reference in their entireties.

Probes can be readily synthesized by standard techniques, e.g., solid phase synthesis via phosphoramidite chemistry, as disclosed in U.S. Pat. Nos. 4,458,066 and 4,415,732, incorporated herein by reference; Beaucage et al., Tetrahedron (1992) 48:2223-2311; and Applied Biosystems User Bulletin No. 13 (1 Apr. 1987). Other chemical synthesis methods include, for example, the phosphotriester method described by Narang et al., Meth. Enzymol. (1979) 68:90 and the phosphodiester method disclosed by Brown et al., Meth. Enzymol. (1979) 68:109. Poly(A) or poly(C), or other non-complementary nucleotide extensions may be incorporated into polynucleotides using these same methods. Hexaethylene oxide extensions may be coupled to the polynucleotides by methods known in the art. Cload et al., J. Am. Chem. Soc. (1991) 113:6324-6326; U.S. Pat. No. 4,914,210 to Levenson et al.; Durand et al., Nucleic Acids Res. (1990) 18:6353-6359; and Horn et al., Tet. Lett. (1986) 27:4705-4708.

Alternatively, probes can be produced by amplification of a target nucleic acid using, e.g., polymerase chain reaction (PCR), nucleic acid sequence based amplification (NASBA), ligase chain reaction (LCR), self-sustained sequence replication (3SR), Q-beta amplification; strand displacement amplification, or any other nucleic acid amplification method to produce a probe capable of hybridizing to the desired target sequence.

The probes may be coupled to labels for detection. There are several means known for derivatizing polynucleotides with reactive functionalities which permit the addition of a label. For example, several approaches are available for biotinylating probes so that radioactive, fluorescent, chemiluminescent, enzymatic, or electron dense labels can be attached via avidin. See, e.g., Broken et al., Nucl. Acids Res. (1978) 5:363-384 which discloses the use of ferritin-avidin-biotin labels; and Chollet et al., Nucl. Acids Res. (1985) 13:1529-1541 which discloses biotinylation of the 5' termini of polynucleotides via an aminoalkylphosphoramide linker arm. Several methods are also available for synthesizing amino-derivatized oligonucleotides which are readily labeled by fluorescent or other types of compounds derivatized by amino-reactive groups, such as isothiocyanate, N-hydroxysuccinimide, or the like, see, e.g., Connolly, Nucl. Acids Res. (1987) 15:3131-3139, Gibson et al. Nucl. Acids Res. (1987) 15:6455-6467 and U.S. Pat. No. 4,605,735 to Miyoshi et al. Methods are also available for synthesizing sulfhydryl-derivatized polynucleotides, which can be reacted with thiol-specific labels, see, e.g., U.S. Pat. No. 4,757,141 to Fung et al., Connolly et al., Nucl. Acids Res. (1985) 13:4485-4502 and Spoat et al. Nucl. Acids Res. (1987) 15:4837-4848. A comprehensive review of methodologies for labeling DNA fragments is provided in Matthews et al., Anal. Biochem. (1988) 169:1-25.

For example, probes may be fluorescently labeled. Guidance for selecting appropriate fluorescent labels can be found in Smith et al., Meth. Enzymol. (1987) 155:260-301; Karger et al., Nucl. Acids Res. (1991) 19:4955-4962; Guo et al. (2012) Anal. Bioanal. Chem. 402(10):3115-3125; and Molecular Probes Handbook, A Guide to Fluorescent Probes and Labeling Technologies, 11th edition, Johnson and Spence eds., 2010 (Molecular Probes/Life Technologies); herein incorporated by reference. Fluorescent labels include fluorescein and derivatives thereof, such as disclosed in U.S. Pat. No. 4,318,846 and Lee et al., Cytometry (1989) 10:151-164. Dyes for use in the present invention include 3-phenyl-7-isocyanatocoumarin, methyl coumarin-3-acetic acid (AMCA), acridines, such as 9-isothiocyanatoacridine and acridine orange, pyrenes, benzoxadiazoles, and stilbenes, such as disclosed in U.S. Pat. No. 4,174,384. Additional dyes include SYBR green, SYBR gold, Yakima Yellow, Texas Red, 3-(ε-carboxypentyl)-3'-ethyl-5,5'-dimethyloxacarbocyanine (CYA); 6-carboxy fluorescein (FAM); CAL Fluor Orange 560, CAL Fluor Red 610, Quasar Blue 670; 5,6-carboxyrhodamine-110 (R110); 6-carboxyrhodamine-6G (R6G); N',N',N',N'-tetramethyl-6-carboxyrhodamine (TAMRA); 6-carboxy-X-rhodamine (ROX); 2',4',5',7',-tetrachloro-4-7-dichlorofluorescein (TET); 2',7'-dimethoxy-4',5'-6 carboxyrhodamine (JOE); 6-carboxy-2',4,4',5',7,7'-hexachlorofluorescein (HEX); Dragonfly orange; ATTO-Tec; Bodipy; ALEXA; VIC, Cy3, Cy5, and Cy7. These dyes are commercially available from various suppliers such as Life Technologies (Carlsbad, Calif.), Biosearch Technologies (Novato, Calif.), and Integrated DNA Technologies (Coralville, Iowa). Fluorescent labels include fluorescein and derivatives thereof, such as disclosed in U.S. Pat. No. 4,318,846 and Lee et al., Cytometry (1989) 10:151-164, and 6-FAM, JOE, TAMRA, ROX, HEX-1, HEX-2, ZOE, TET-1 or NAN-2, and the like.

Fluorophores may be covalently attached to a particular nucleotide, for example, and the labeled nucleotide incorporated into the probe using standard techniques such as nick translation, random priming, and PCR labeling. Alternatively, a fluorophore may be covalently attached via a linker to a deoxycytidine nucleotide that has been transaminated. Methods for labeling probes are described in U.S. Pat. No. 5,491,224 and Molecular Cytogenetics: Protocols and Applications (2002), Y.-S. Fan, Ed., Chapter 2, "Labeling Fluorescence In Situ Hybridization Probes for Genomic Targets," L. Morrison et al., p. 21-40, Humana Press; which are herein incorporated by reference.

One of skill in the art will recognize that other luminescent agents or dyes may be used in lieu of fluorophores as label containing moieties. Other luminescent agents, which may be used, include, for example, radioluminescent, chemiluminescent, bioluminescent, and phosphorescent label containing moieties, as well as quantum dots. Alternatively, in situ hybridization of chromosomal probes may be employed with the use of detection moieties visualized by indirect means. Probes may be labeled with biotin or digoxygenin using routine methods known in the art, and then further processed for detection. Visualization of a biotin-containing probe may be achieved via subsequent binding of avidin conjugated to a detectable marker. Chromosomal probes hybridized to target regions may alternatively be visualized by enzymatic reactions of label moieties with suitable substrates for the production of insoluble color products. Each probe may be discriminated from other probes within the set by choice of a distinct label. A biotin-containing probe within a set may be detected via subsequent incubation with avidin conjugated to alkaline phosphatase (AP) or horseradish peroxidase (HRP) and a suitable substrate, e.g., 5-bromo-4-chloro-3-indolylphosphate and nitro blue tetrazolium (NBT) serve as substrates for alkaline phosphatase, whereas diaminobenzidine serves as a substrate for HRP.

In another embodiment, detection of the SNP sequence is performed using allele-specific amplification. In the case of PCR, amplification primers can be designed to bind to a portion of one of the disclosed genes, and the terminal base at the 3' end is used to discriminate between the major and minor alleles or mutant and wild-type forms of the genes. If the terminal base matches the major or minor allele, polymerase-dependent three prime extension can proceed. Amplification products can be detected with specific probes. This method for detecting point mutations or polymorphisms is described in detail by Sommer et al. in Mayo Clin. Proc. 64:1361-1372 (1989).

Tetra-primer ARMS-PCR uses two pairs of primers that can amplify two alleles of a SNP in one PCR reaction. Allele-specific primers are used that hybridize at the SNP location, but each matches perfectly to only one of the possible alleles. If a given allele is present in the PCR reaction, the primer pair specific to that allele will amplify that allele, but not the other allele of the SNP. The two primer pairs for the different alleles may be designed such that their PCR products are of significantly different length, which allows them to be distinguished readily by gel electrophoresis. See, e.g., Muñoz et al. (2009) J. Microbiol. Methods. 78(2):245-246 and Chiapparino et al. (2004) Genome. 47(2):414-420; herein incorporated by reference.

SNPs may also be detected by ligase chain reaction (LCR) or ligase detection reaction (LDR). The specificity of the ligation reaction is used to discriminate between the major and minor alleles of the SNP. Two probes are hybridized at the SNP polymorphic site of a nucleic acid of interest, whereby ligation can only occur if the probes are identical to the target sequence. See e.g., Psifidi et al. (2011) PLoS One 6(1):e14560; Asari et al. (2010) Mol. Cell. Probes. 24(6):381-386; Lowe et al. (2010) Anal Chem. 82(13):5810-5814; herein incorporated by reference.

SNPs can also be detected in a biological sample by sequencing and SNP typing. In the former method, one simply carries out whole genome sequencing of a patient sample, and uses the results to detect the present sequences. Whole genome analysis is used in the field of "personal genomics," and genetic testing services exist, which provide full genome sequencing using massively parallel sequencing. Massively parallel sequencing is described e.g. in U.S. Pat. No. 5,695,934, entitled "Massively parallel sequencing of sorted polynucleotides," and US 2010/0113283 A1, entitled "Massively multiplexed sequencing." Massively parallel sequencing typically involves obtaining DNA representing an entire genome, fragmenting it, and obtaining millions of random short sequences, which are assembled by mapping them to a reference genome sequence.

Commercial services also exist which will genotype approximately 1 million SNPs for a fixed fee. SNP analysis can be carried out by a variety of methods that do not involve massively parallel random sequencing. As described below, a commercially available MassARRAY system can be used. This system uses matrix-assisted laser desorption ionization time-of-flight mass spectrometry (MALDI-TOF MS) coupled with single-base extension PCR for high-throughput multiplex SNP detection. Another commercial SNP system is made by Illumina. The Illumina Golden Gate assay generates SNP specific PCR products that are subsequently hybridized to beads either on a solid matrix or in solution. Three oligonucleotides are synthesized for each SNP: two allele specific oligos (ASOs) that distinguish the SNP, and a locus specific sequence (LSO) just downstream of the SNP. The ASO and LSO sequences also contain target sequences for a set of universal primers (P1 through P3 in the adjacent figure), while each LSO also contains a particular address sequences (the "illumicode") complementary to sequences attached to beads.

As another example, Affymetrix SNP arrays (also used in the present examples) use multiple sets of short oligonucleotide probes for each known SNP. The design of an SNP array such as manufactured by Affymetrix and Illumina is described further in LaFamboise, "Single nucleotide polymorphism arrays: a decade of biological, computational and technological advances," Nuc. Acids Res. 37(13):4181-4193 (2009), which provides additional description of methods for detecting SNPs.

Another technology useful in SNP analysis is PCR-dynamic allele specific hybridization (DASH), which involves dynamic heating and coincident monitoring of DNA denaturation, as disclosed by Howell et al. (Nat. Biotech. 17:87-88, 1999). A target sequence is amplified (e.g., by PCR) using one biotinylated primer. The biotinylated product strand is bound to a streptavidin-coated microtiter plate well (or other suitable surface), and the non-biotinylated strand is rinsed away with alkali wash solution. An oligonucleotide probe, specific for one allele (e.g., the wild-type allele), is hybridized to the target at low temperature. This probe forms a duplex DNA region that interacts with a double strand-specific intercalating dye. When subsequently excited, the dye emits fluorescence proportional to the amount of double-stranded DNA (probetarget duplex) present. The sample is then steadily heated while fluorescence is continually monitored. A rapid fall in fluorescence indicates the denaturing temperature of the probe-target duplex. Using this technique, a single-base mismatch between the probe and target results in a significant lowering of melting temperature (Tm) that can be readily detected.

A variety of other techniques can be used to detect polymorphisms, including but not limited to, the Invader assay with Flap endonuclease (FEN), the Serial Invasive Signal Amplification Reaction (SISAR), the oligonucleotide ligase assay, restriction fragment length polymorphism (RFLP), single-strand conformation polymorphism, temperature gradient gel electrophoresis (TGGE), and denaturing high performance liquid chromatography (DHPLC). See, for example, *Molecular Analysis and Genome Discovery* (R. Rapley and S. Harbron eds., Wiley 1$^{st}$ edition, 2004); Jones et al. (2009) New Phytol. 183(4):935-966; Kwok et al. (2003) Curr Issues Mol. Biol. 5(2):43-60; Muñoz et al. (2009) J. Microbiol. Methods 78(2):245-246; Chiapparino et al. (2004) Genome. 47(2):414-420; Olivier (2005) Mutat Res. 573(1-2):103-110; Hsu et al. (2001) Clin. Chem. 47(8): 1373-1377; Hall et al. (2000) Proc. Natl. Acad. Sci. U.S.A. 97(15):8272-8277; Li et al. (2011) J. Nanosci. Nanotechnol. 11(2):994-1003; Tang et al. (2009) Hum. Mutat. 30(10): 1460-1468; Chuang et al. (2008) Anticancer Res. 28(4A): 2001-2007; Chang et al. (2006) BMC Genomics 7:30; Galeano et al. (2009) BMC Genomics 10:629; Larsen et al. (2001) Pharmacogenomics 2(4):387-399; Yu et al. (2006) Curr. Protoc. Hum. Genet. Chapter 7: Unit 7.10; Lilleberg (2003) Curr. Opin. Drug Discov. Devel. 6(2):237-252; and U.S. Pat. Nos. 4,666,828; 4,801,531; 5,110,920; 5,268,267; 5,387,506; 5,691,153; 5,698,339; 5,736,330; 5,834,200; 5,922,542; and 5,998,137 for a description of such methods; herein incorporated by reference in their entireties.

If the polymorphism is located in the coding region of a gene of interest, the SNP can be identified indirectly by detection of the variant protein produced by the SNP. Variant proteins (i.e., containing an amino acid substitution encoded by the SNP) can be detected using antibodies specific for the variant protein. For example, immunoassays that can be used to detect variant proteins produced by SNPs include, but are not limited to, immunohistochemistry (IHC), western blotting, enzyme-linked immunosorbent assay (ELISA), radioimmunoassays (RIA), "sandwich" immunoassays, fluorescent immunoassays, and immunoprecipitation assays, the procedures of which are well known in the art (see, e.g., Schwarz et al. (2010) Clin. Chem. Lab. Med. 48(12):1745-1749; *The Immunoassay Handbook* (D. G. Wild ed., Elsevier Science; 3$^{rd}$ edition, 2005); Ausubel et al, eds, 1994, *Current Protocols in Molecular Biology*, Vol. 1 (John Wiley & Sons, Inc., New York); Coligan *Current Protocols in Immunology* (1991); Harlow & Lane, *Antibodies: A Laboratory Manual* (1988); *Handbook of Experimental Immunology*, Vols. I-IV (D. M. Weir and C. C. Blackwell eds., Blackwell Scientific Publications); herein incorporated by reference herein in their entireties).

Agents for detecting which allele is present at SNP rs7767652 in a subject can be provided in the form of a kit. The kit may include one or more agents for detection of the SNP, such as allele-specific hybridization probes, PCR primers, or a SNP microarray for determining which allele is present. The kit may further comprise a container for holding a biological sample isolated from a human subject for genetic testing and printed instructions for reacting agents with the biological sample or a portion of the biological sample to detect the presence of at least one SNP in the biological sample. The agents may be packaged in separate containers. The kit may further comprise one or more control reference samples or other reagents for detecting or genotyping SNPs.

In certain embodiments, the kit further comprises reagents for performing dynamic allele-specific hybridization (DASH), Tetra-primer ARMS-PCR, a TaqMan 5'-nuclease assay; an Invader assay with Flap endonuclease (FEN), a Serial Invasive Signal Amplification Reaction (SISAR), an oligonucleotide ligase assay, restriction fragment length polymorphism (RFLP), single-strand conformation polymorphism, temperature gradient gel electrophoresis (TGGE), denaturing high performance liquid chromatography (DHPLC), sequencing, or an immunoassay.

The kit can comprise one or more containers for compositions contained in the kit. Compositions can be in liquid form or can be lyophilized. Suitable containers for the compositions include, for example, bottles, vials, syringes, and test tubes. Containers can be formed from a variety of materials, including glass or plastic. The kit can also comprise a package insert containing written instructions for methods of detecting SNPs and predicting future skin aging.

III. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

The Neuromodulator Hypocretin/Orexin Receptor 2 Regulates Cardiac Function

Heart failure is the most common admitting diagnosis for patients in the US and has a worse prognosis than most cancers (Lloyd-Jones et al. (2010) Circulation 121:e46-e215). Although clearly heritable (Lee et al. (2006) N. Engl. J. Med. 355:138-147), vanishingly few genetic associations have been identified. We studied 866 patients with heart failure and compared the extremes of response to medical therapy using a genome wide approach that informed the systems-based design of a customized single nucleotide variant array. Polymorphism rs7767652, upstream of the hypocretin (orexin) receptor 2 (HCRTR2) gene, is associated with improvement in heart function (odds ratio (OR) 0.40, p=3.29×10$^{-5}$) and replicated in an independent heart failure cohort. Allele-specific luciferase reporter assays demonstrated higher relative enhancer activity with the rs7767652 major allele while expression of HCRTR2 was higher in human diseased tissue compared to normal tissue. In a heart failure model, HCRTR2 deficient mice exhibited poorer cardiac function, treadmill exercise capacity and greater myocardial scarring compared to wild-type mice. Finally, orexin, an HCRTR2 agonist was successful in rescuing heart function in a mouse model of heart failure. Here, a systems approach identifies a novel genetic contribution to human heart failure and a promising therapeutic agent efficacious in a mouse model.

Heart failure, a syndrome characterized by impaired cardiac function, affects over five million people in the US and is expected to affect 3.5% of the population over the next 20 years (Heidenreich et al. (2012) Circulation 123:933-944). Heart failure can result from a wide range of conditions, commonly coronary artery disease and hypertension (Ho et al. (1993) J. Am. Coll. Cardiol. 22:6A-13A). Few studies have explored the genetic basis of heart failure. Candidate gene studies identified associations between common variants in HSPB7 and FRMD4B and dilated cardiomyopathy (Stark et al. (2010) PLoS Genetics 6:e1001167) or advanced heart failure (Cappola et al. (2010) Circ. Cardiovasc. Genet. 3:147-154). Targeted genotyping of common variants in ADRB1 and GRK5, members of the β-adrenergic receptor signaling pathway, demonstrated associations with survival (Cresci et al. (2009) J. Am. Coll. Cardiol. 54:432-444; Liggett et al. (2008) Nature Medicine 14:510-517). In the limited genome-wide studies of heart failure (Larson et al. (2007) BMC Medical Genetics 8 Suppl. 1:S5; Smith et al. (2010) Circ. Cardiovasc. Genet. 3:256-266; Villard et al. (2011) Eur. Heart J. 32:1065-1076; Meder et al. (2014) Eur. Heart J. 35:1069-1077), only one common variant associated with dilated cardiomyopathy at genome-wide significance has replicated (Meder et al., supra).

With optimal medical therapy, some exhibit a dramatic improvement in heart function while others deteriorate. Most heart failure genomic studies to date have been cross-sectional. We explored the genetic basis of extreme response to medical intervention, identifying genetic markers of dramatic improvement versus clinical deterioration towards heart transplant.

We first designed a customized single nucleotide variation (SNV) array, generating posterior probabilities by compiling publicly available myocardial gene expression data and combining this with a genome-wide association (GWA) analysis of extreme response to heart failure therapy and other resources (FIG. 1). We evaluated 866 patients with heart failure at Stanford University. Patients at the extreme of the distribution of dynamic change were genotyped using a 561,464 SNV genotype chip that was used to inform the design of a customized genotyping array.

All publicly available microarray gene expression data from human cardiac tissue (Dewey et al. (2011) Circ. Cardiovasc. Genet. 4:26-35) was collected from the Gene Expression Omnibus (GEO) database (ncbi.nlm.nih.gov/geo/) and normalized using a median-absolute-deviation algorithm (Smyth et al. (2003) Methods 31:265-273). Differences in expression levels between failing and normal human myocardium were measured using significance analysis of microarrays (Storey et al. (2003) Methods Mol. Biol. 224:149-157). The significance value (d-score) was used to weight (Genovese et al. (2006) Biometrika 93:509-524; Roeder et al. (2007) Genetic Epidemiology 31:741-747) p-values from the informative GWA analysis. The top-ranking genic SNPs were included in the customized array (Table 3). The top intergenic SNPs from the informative GWA analysis, ranked by unweighted p-values, were also included in the customized array (Table 4).

Figure 4:
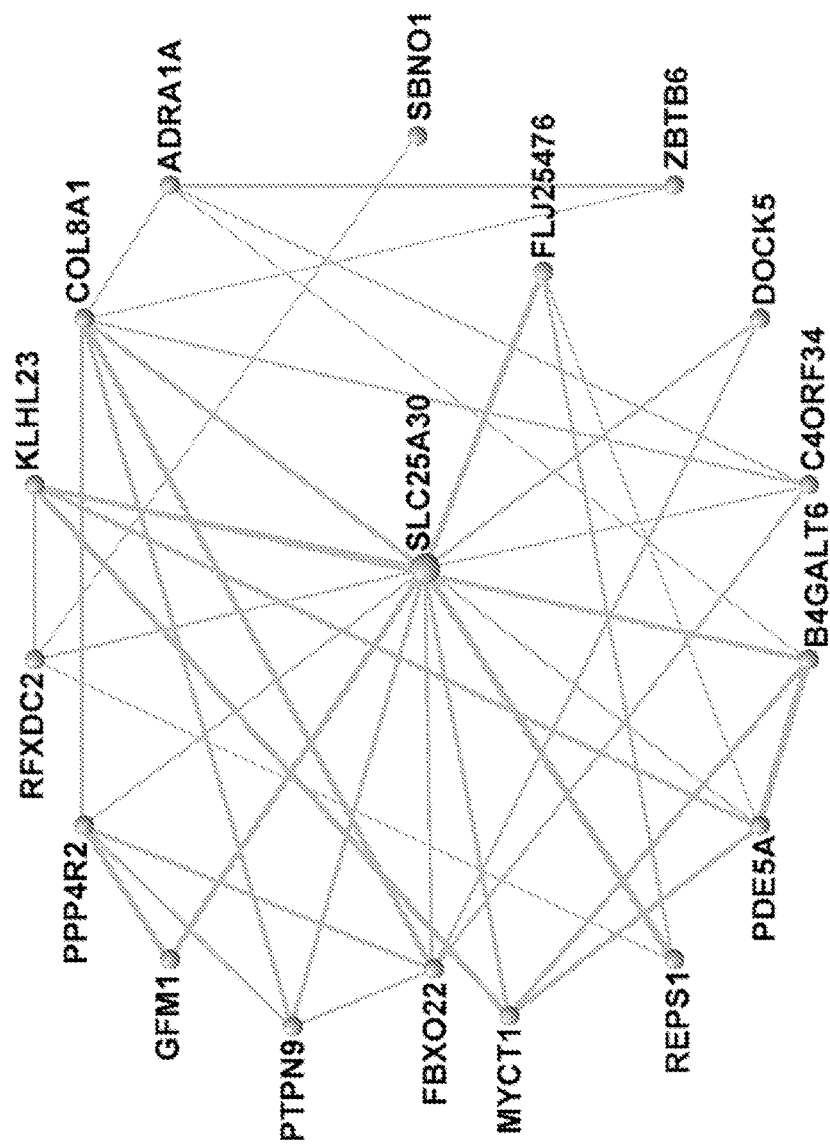
FIG. 4 shows the coexpression module most significantly associated with differential gene expression in heart failure tissue. SLC25A30 is the hub of the 18-member module most significantly associated with differential gene expression in heart failure tissue compared to normal myocardial tissue.

Next, gene coexpression networks with scale-free topology were created from a collated file of all human myocardial gene expression data (n=340 expression arrays) (Dewey et al., supra). Genes were clustered using average linkage hierarchical clustering and adaptively assigned to modules using a dynamic tree cutting algorithm (Langfelder et al. (2008) Bioinformatics 24:719-720). Modules with topology shared between normal and failing myocardium were ranked according to differential gene expression (quantified by average d-score for modular gene expression differences between normal and failing myocardium) to identify sets of genes associated with adaptation to heart failure. Common variants from the hub genes, defined as the genes in each module with maximum intra-modular connectivity, from the highest-ranking modules were included in the customized array (Table 5). The top-ranking module with SLC25A30 as its hub is depicted in FIG. 4. Next, Pubmed abstracts were retrieved and semantic mining was used to create a gene-gene interaction network (Ashley et al. (2006) Circulation 114:2644-2654; King et al. (2005) Physiological Genomics 23:103-118). The top common variants of the hub genes, ranked by average d-scores (Storey et al. (2003) Methods Mol. Biol. 224:149-157), were included in the customized array (Table 6). Finally, a curated set of SNVs derived from multiple sources including significant SNPs from prior cardiovascular GWA studies (Table 7), microRNA gene polymorphisms, and coding SNVs in genes known to be targets of pharmacologic agents used in heart failure were included. The selected SNVs were placed on a customized Illumina Golden Gate platform.

Figure 2A:
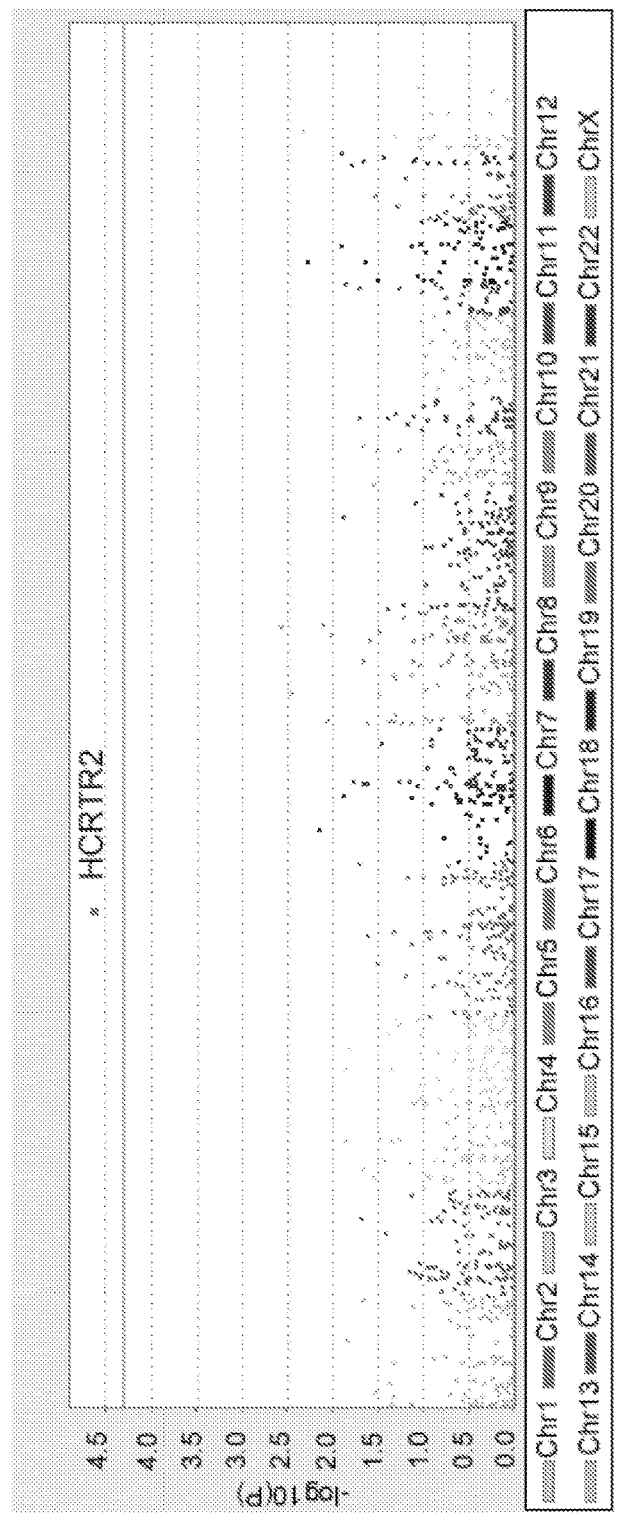
FIGS. 2A and 2B show a Manhattan plot showing the significance of association with a 10% improvement in ejection fraction for SNPs in the customized heart failure array analysis of Phase II individuals and a regional LD plot of the statistically significant locus.
Figure 2B:
Figure 3A:
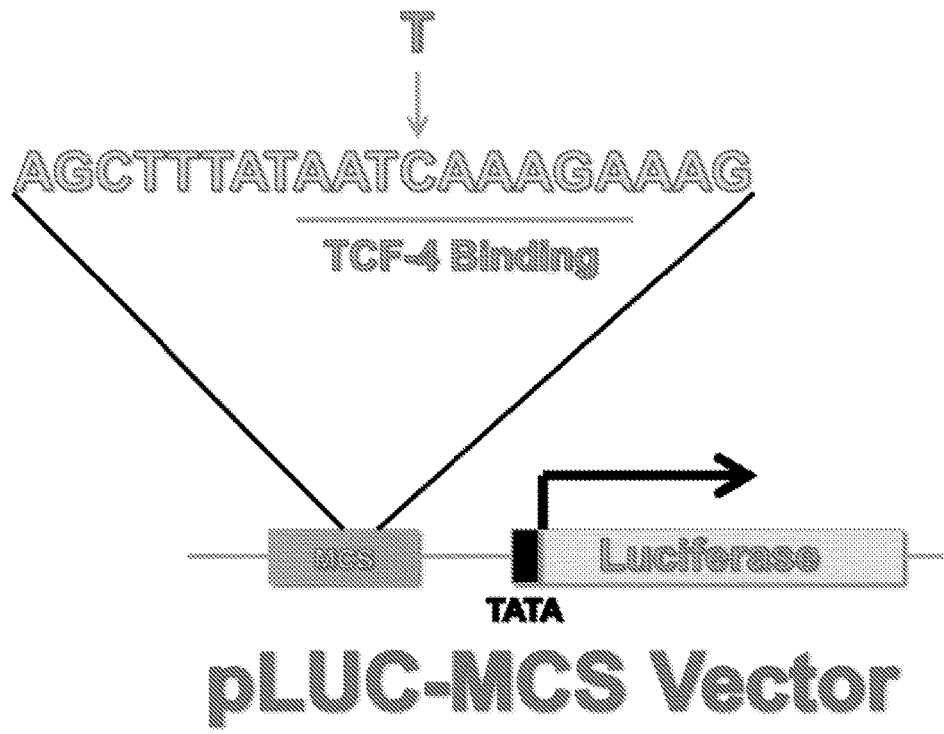
FIGS. 3A-3H show the functional roles of the rs7767652 allele and HCRTR2 assessed with allele-specific gene expression, measurement of human HCRTR2 gene expression in diseased tissue, measurement of ventricular function, exercise capacity and trichrome staining in HCRTR2 deficient mice and infusion of orexin A in chemically stressed mice.
Figure 3B:
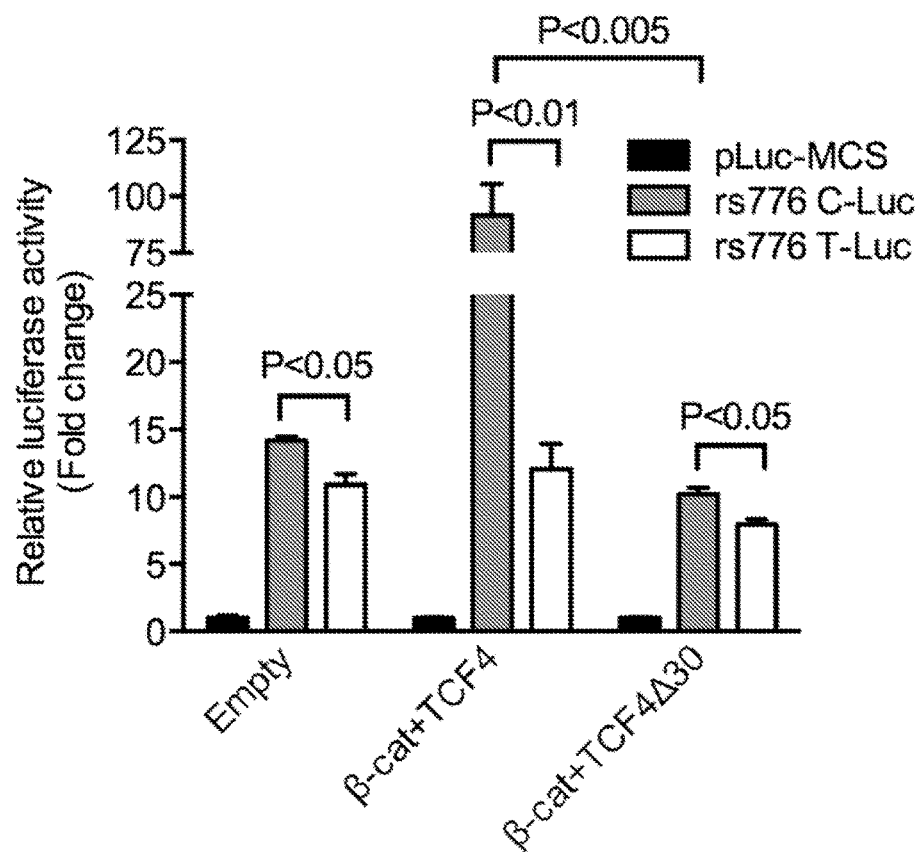

Baseline characteristics of the 591 heart failure patients, 23% of whom had an absolute improvement of 10% in their ejection fraction, genotyped with the custom array are in Table 1. An additive logistic regression model, adjusted for age, sex and race, was used to test the association between each SNV on the customized array and improved ejection fraction (Manhattan plot, FIG. 2A; quantile-quantile plot, FIG. 5). Patients with the minor allele for rs7767652 were less likely to have a response of greater than 10% in ejection fraction (OR 0.394, p=3.29×10$^{-5}$), with statistical significance below the Bonferroni cutoff of 0.05/1402=3.56×10$^{-5}$. This variant was chosen for custom array as one of the intergenic SNVs. In the informative GWA, patients with the minor allele for rs7767652 were less likely to have a response of greater than 20% in ejection fraction compared to transplanted patients (OR 0.279, p=0.0040). The meta-analysis p-value was 9.04×10$^{-6}$. rs7767652 is approximately 2,700 base pairs upstream from HCRTR2, within a haplotype block that encompasses several alternative splice sites (Chen et al. (2010) Biochemical J. 427:377-390) and the 5' untranslated region (UTR) of HCRTR2 (FIG. 2B). Top results from each of the custom array selection categories are presented in Table 2 and Tables 3-8. We sought replication in 798 heart failure patients from the cross-sectional Penn Heart Failure Study (Cappola et al. (2010) Circ. Cardiovasc. Genet. 3:147-154). After multivariate adjustment, heart failure patients with the minor allele for rs7767652 were less likely to have an EF greater than 35% (OR 0.769, p=0.021). To assess the potential regulatory role of the lead variant rs7767652 upstream of HCRTR2, we first mapped putative transcription factor binding sites in silico using various bioinformatics tools, such as TRANSFAC, JASPAR, and MatInspector (Table 8). The minor (T) allele predicted disruption of a TCF4 binding site containing the motif ATCAAAG. We then measured allele-specific gene expression using luciferase reporters containing the predicted binding site in transfected C2C12 myoblast cells (FIG. 3A). At baseline, transfection with the minor allele (T) construct of rs7767652 resulted in lower luciferase activity compared to the major allele (C) construct (p<0.05) (FIG. 3B). We also observed that the minor allele significantly disrupted β-catenin/TCF4-mediated transactivation in cells overexpressing human β-catenin and TCF4 cofactors (p<0.01). These effects were abolished in the presence of a TCF4 transactivation mutant (p<0.005).

Figure 3C:
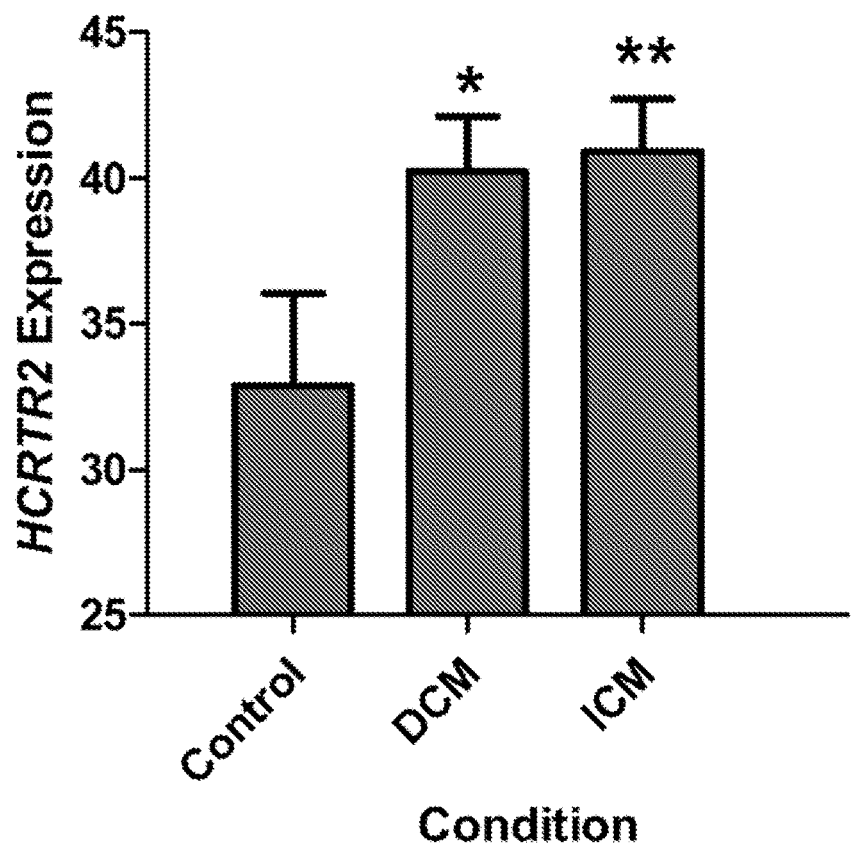

To assess a myocardial role for this neuropeptide receptor, we compared HCRTR2 expression in diseased hearts (dilated n=162, ischemic n=143) with control tissue (n=45). Expression of HCRTR2 was greater in dilated cardiomyopathy (p=0.00017) and ischemic cardiomyopathy samples (p=0.000044) compared to controls (FIG. 3C).

To investigate a causal role for HCRTR2 in heart failure pathogenesis, we performed heart function testing via ultrasound in HCRTR2 transcription-disrupted (Mochizuki et al.

Figure 3D:
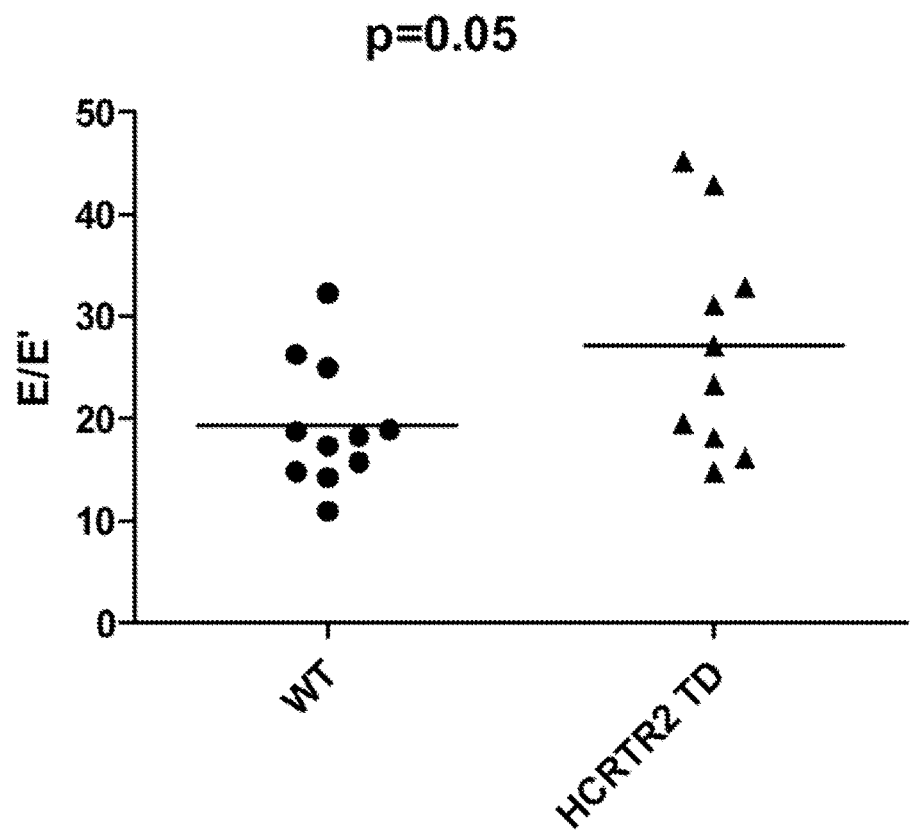
Figure 3E:
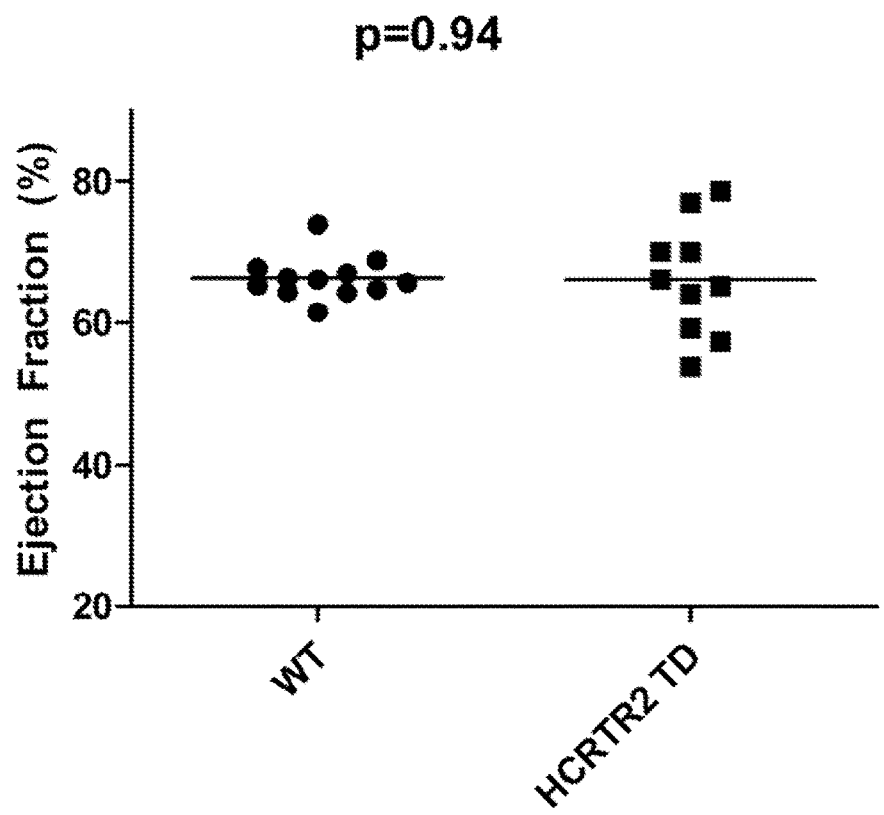
Figure 3F:
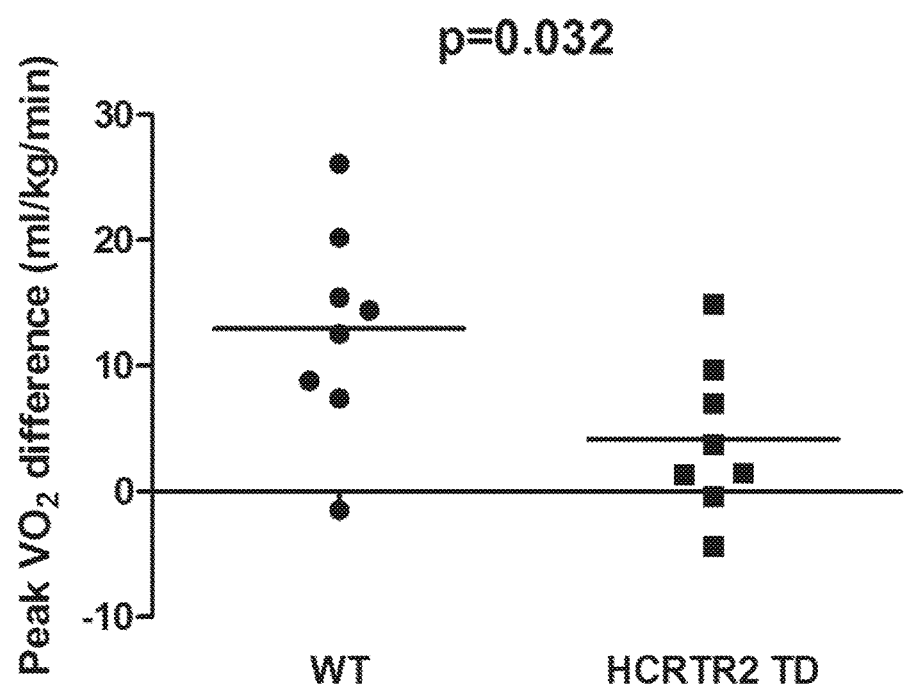
Figure 3G:
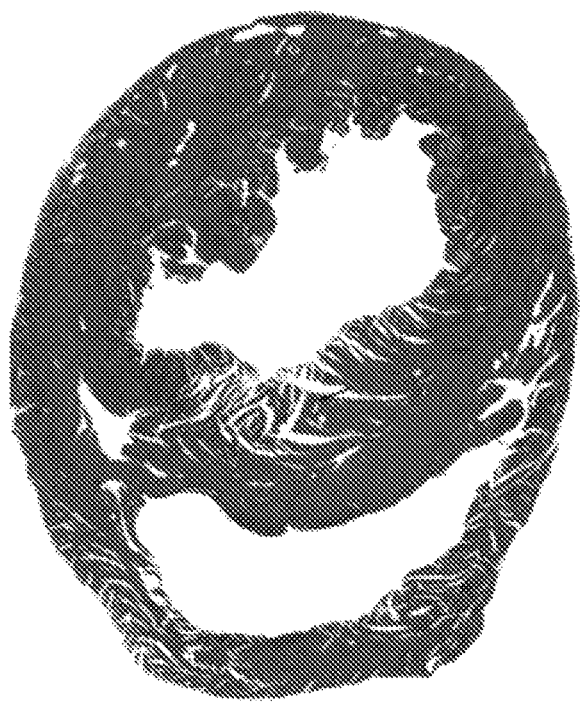
Figure 3G:
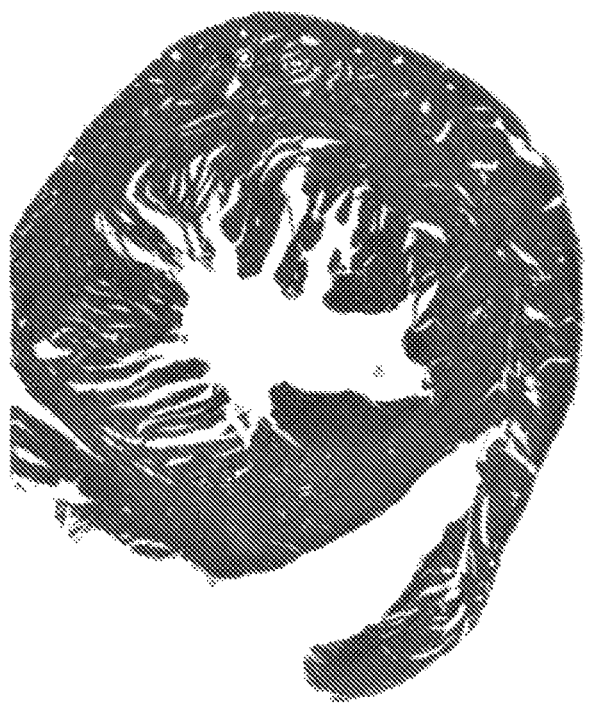

(2011) Proc. Natl. Acad. Sci. U.S.A. 108:4471-4476) (TD) mice (n=10) compared to wild-type (n=11). There was greater diastolic dysfunction in the HCRTR2 TD mice compared to the wild-type mice (p=0.05, FIG. 3D), but no significant difference in systolic function (FIG. 3E). Similar studies in a small number of HCRTR2 knockout mice (Chemelli et al. (1999) Cell 98:437-451) (n=5) compared to controls (n=5) also demonstrated a trend towards greater diastolic dysfunction. HCRTR2 TD mice that underwent chemical stress with two weeks of angiotensin II and isoproterenol infusion had a smaller increase in treadmill exercise capacity (FIG. 3F) and greater evidence of myocardial fibrosis (FIG. 3G) compared to wild type mice.

Figure 3H:
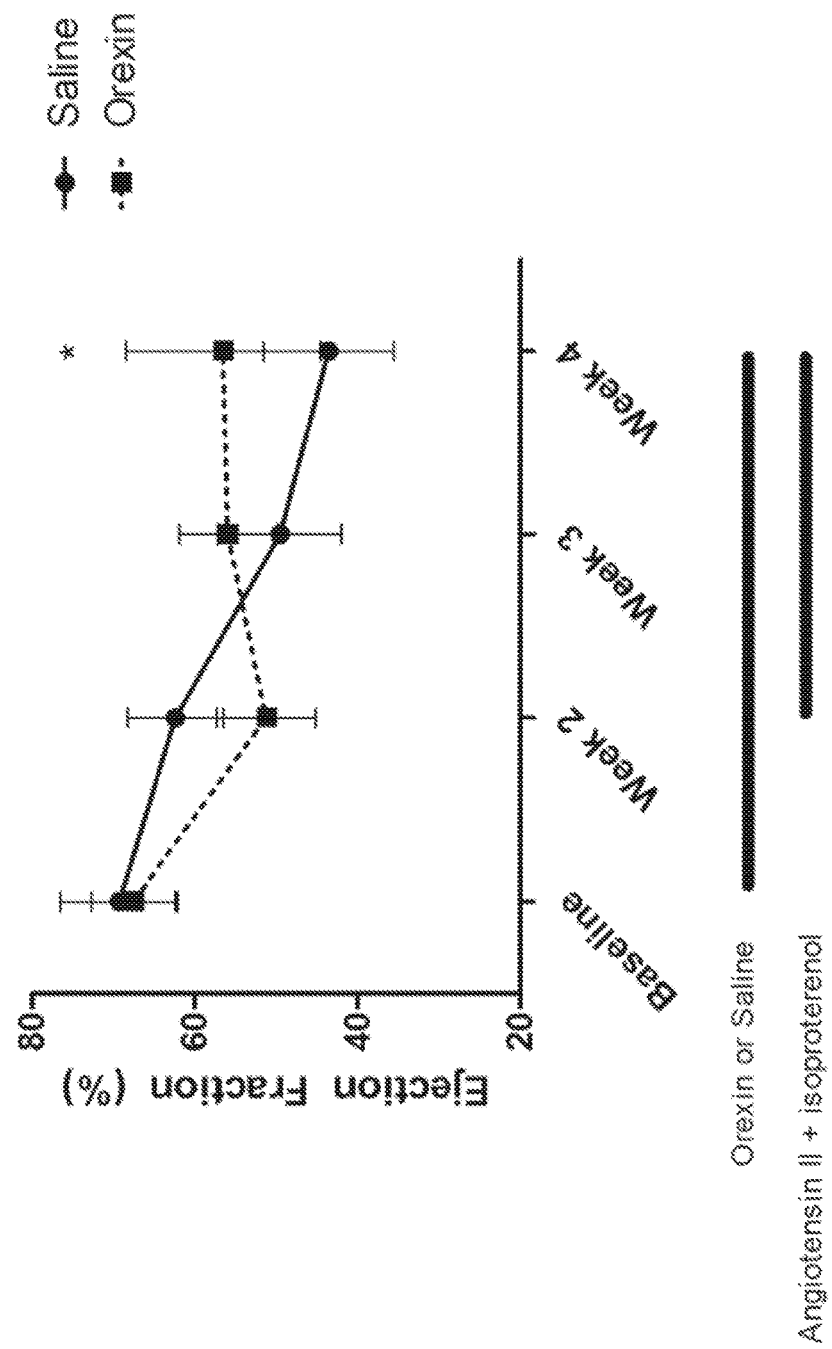

Finally, to assess the potential of HCRTR2 as a novel therapeutic target for heart failure, wild-type mice were infused with saline (n=6) or the HCRTR2 agonist orexin A (n=7) for four weeks. At week two, all mice underwent infusion of angiotensin II and isoproterenol, neurohormones that mimic human heart failure. Echocardiography was performed blinded to drug infusion status at baseline, 2, 3 and 4 weeks (FIG. 3H). Mice with orexin A had better systolic function compared to controls (p=0.045).

The HCRTR2 gene encodes a G-coupled receptor that binds hypocretin (orexin) A and B, neuropeptides involved in appetite (Lubkin et al. (1998) Biochem. Biophys. Res. Commun. 253:241-245; Sakurai et al. (1998) Cell 92:1 page following 696) and sleep (Lin et al. (1999) Cell 98:365-376) regulation. Although highly expressed in the hypothalamus (Sakurai et al., supra), its expression has been documented in several tissues including gut (Kirchgessner et al. (1999) Neuron 24:941-951) and adrenal glands (Lopez et al. (1999) Endocrinology 140:5991-5994). Alternative splice variants of HCRTR2 are expressed in heart tissue (Chen et al. (2010) Biochem. J. 427:377-390). Orexins provoke increases in blood pressure and heart rate via a centrally-mediated response (Shirasaka et al. (1999) Am. J. Physiol. 277: R1780-1785; Samson et al. (1999) Brain Research 831:248-253; Matsumura et al. (2001) Hypertension 37:1382-1387). Their effects on myocardial function have not been studied.

We used a customized gene array to identify a genomic variant in the regulatory region of HCRTR2 associated with improved left ventricular function. Allele-specific reporter assays at this locus suggested a role in regulating nearby gene transcription. Our finding that mice infused with an HCRTR2 agonist were protected from chemical stress-induced ventricular dysfunction suggests a promising role for HCRTR2 in regulation of ventricular function. Unlike the neurohormonal axis of the renin-angiotensin-aldosterone system, the effects of hypocretins on myocardial function have not yet been characterized, but they may play a role in regulating myocardial fibrosis. Additional studies to characterize central versus peripheral roles these neuropeptides play in regulation of myocardial function are beyond the scope of this work but may inform future therapeutic development.

Methods

Study Populations

Stanford Heart Failure Genomic Analyses

Patients were recruited from Stanford University Medical Center (Stanford, Calif.) and the Palo Alto Veterans Hospital (Palo Alto, Calif.). 866 patients with clinically diagnosed heart failure referred for subspecialty care between 2005 and 2009 and who had an echocardiogram performed with an ejection fraction less than 55% were included. Patients who could not be contacted by telephone (n=465), or with insufficient clinical data (n=3) were excluded. Those with congenital heart disease or with cardiomyopathy due to infiltrative disease, a peri-partum state, infection or chemotherapy were excluded. Patients whose ejection fraction improved after surgical or percutaneous revascularization, resynchronization therapy with bi-ventricular pacing, or cardioversion were excluded. Those with a myocardial biopsy suggestive of viral cardiomyopathy who responded to viral medication therapy within 30 days of administration were excluded. Patients who suffered an acute myocardial infarction and showed subsequent improvement in their ejection fraction within 3 months of the infarct, or patients with a history of substance abuse with illicit drugs or alcohol within 6 months prior to the study were also excluded. Ejection fraction was measured using routine transthoracic echocardiography obtained by trained echocardiographers using two-dimensional scanning in the parasternal long axis, parasternal short axis and apical views. Change in ejection fraction was measured as maximal difference between lowest recorded ejection fraction and the highest subsequent recorded ejection fraction. Written informed consent was obtained from study participants in accordance with the Stanford University Internal Review Board policy.

For the informative GWAS, case subjects (n=29) were Caucasian patients whose ejection fraction had improved by 20% or greater while on medical therapy. Control patients (n=37) were selected from those followed in the Stanford University transplant clinic who had demonstrated lack of clinical improvement prior to transplant despite medical therapy. The case and control patients were matched by age, sex, race, medical therapy received, baseline ejection fraction on echocardiography, type of cardiomyopathy and duration of heart failure. The 730 heart failure patients remaining underwent genotyping with the custom genotyping array. After exclusion of patients with insufficient clinical data and failure to pass quality control measures, there were a total of 591 successfully genotyped patients. Patients' charts were retrospectively reviewed and their baseline demographics, clinical characteristics and medication use were recorded. Serial measurements from clinically available echocardiograms were also recorded. Outcome data was obtained through detailed phone interviews.

UPenn Replication

For the independent replication study, patients with heart failure were recruited from the University of Pennsylvania as previously described (Cappola et al. (2010) Circ. Cardiovasc. Genet. 3:147-154). Briefly, Caucasian heart failure patients (n=798) were recruited from the Penn Heart Failure Study from an ongoing, NIH-sponsored (HL077101) prospective observational study of patients with advanced heart failure referred for subspecialty care at the University of Pennsylvania Health System (Philadelphia, Pa.). The primary inclusion criterion was a clinical diagnosis of heart failure with abnormal left ventricular function. Extensive clinical data were collected at enrollment. Written informed consent was obtained from study participants in accordance with the Stanford University Internal Review Board policy.

Genotyping

Informative GWAS

Genomic DNA was isolated from whole blood using a commercial DNA extraction kit (Gentra Purgene Kit). The samples were genotyped using the Illumina 550K SNP platform at the Hudson Alpha Institute for Biotechnology (Huntsville, Ala.). A total of 36,244 SNPs with call rates<90%, that had a minor allele frequency (MAF)<1%, or deviated significantly from Hardy-Weinberg equilibrium (P<0.001) were excluded. 525,220 common SNPs remained for association analysis. At the sample-level, 6 cases with call rates<90% were excluded. There were no cases identified with genetic relatedness using pairwise identity by state-based analysis in PLINK (Purcell et al. (2007) Am. J. Hum. Genet. 81:559-575).

Customized SNV Array

Genomic DNA was isolated from either whole blood or buccal swab samples using a commercial DNA extraction kit (Gentra Purgene Kit). The samples were genotyped using a customized 1536 SNP GoldenGate Assay on an Illumina BeadLab system at the HudsonAlpha Institute for Biotechnology (Huntsville, Ala.). Genotype calls were made using Bead Studio Genotyping Module software package, version 3.1 (Illumina, San Diego, Calif.). A total of 134 SNPs with call rates<50%, that had a MAF<1%, or that deviated significantly from Hardy-Weinberg Equilibrium (p<0.001) were excluded. At the sample-level, 118 cases with call rates<80% were excluded.

UPenn Replication

Genomic DNA was isolated from peripheral blood mononuclear cells and DNA quality was assessed utilizing optical absorbance and minigels. Genotyping analysis of the SNP selected for validation, rs7767652, was performed using the MassArray system from Sequenom. Locus-specific PCR and detection primers were designed using the MassArray Assay Design 3.0 software (Sequenom). The SNP did not deviate from Hardy-Weinberg Equilibrium (p<0.05), the minor allele frequency was 23% (similar to HapMap CEU MAF) and 797 out of 798 samples were successfully called.

Analytical Methods
Informative GWAS

Figure 6:
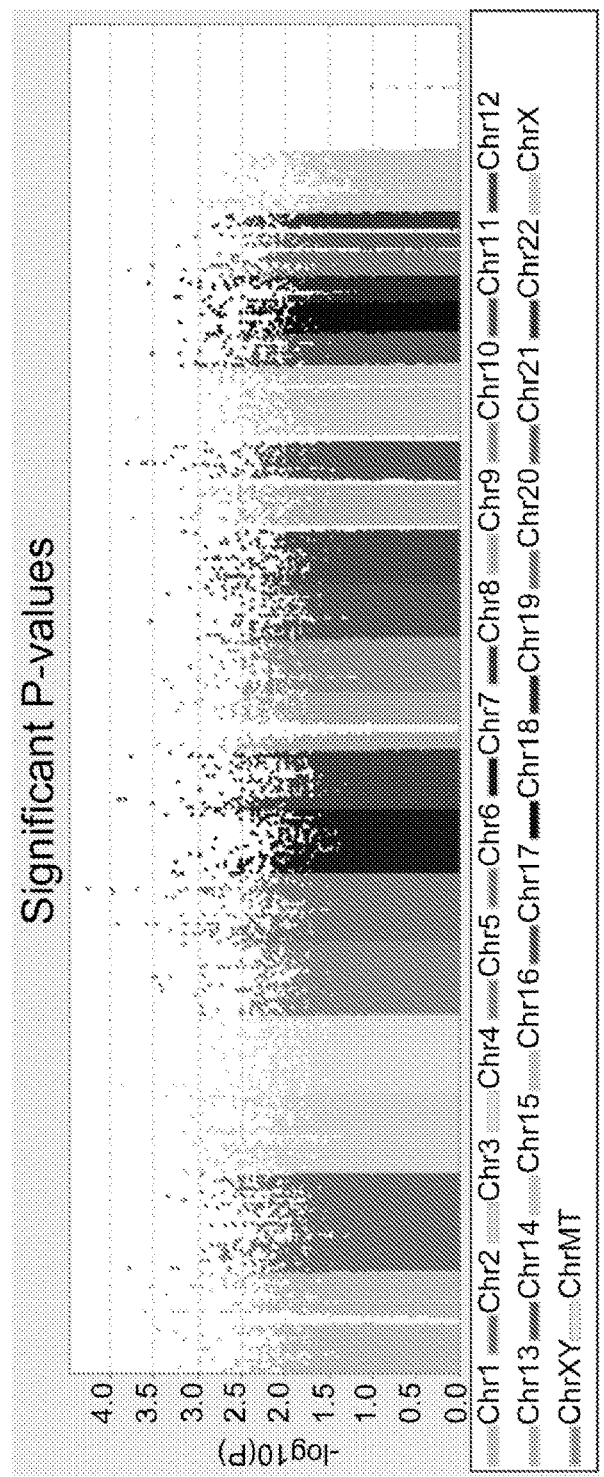
FIG. 6 shows a Manhattan plot showing the significance of association with a 20% improvement in ejection fraction for SNPs in Illumina 550K assay of Phase I individuals. SNPs are plotted on the x axis according to their position on each chromosome against association with greater than 20% improvement in ejection fraction on the y axis (shown as $-\log_{10}P$).
Figure 7:
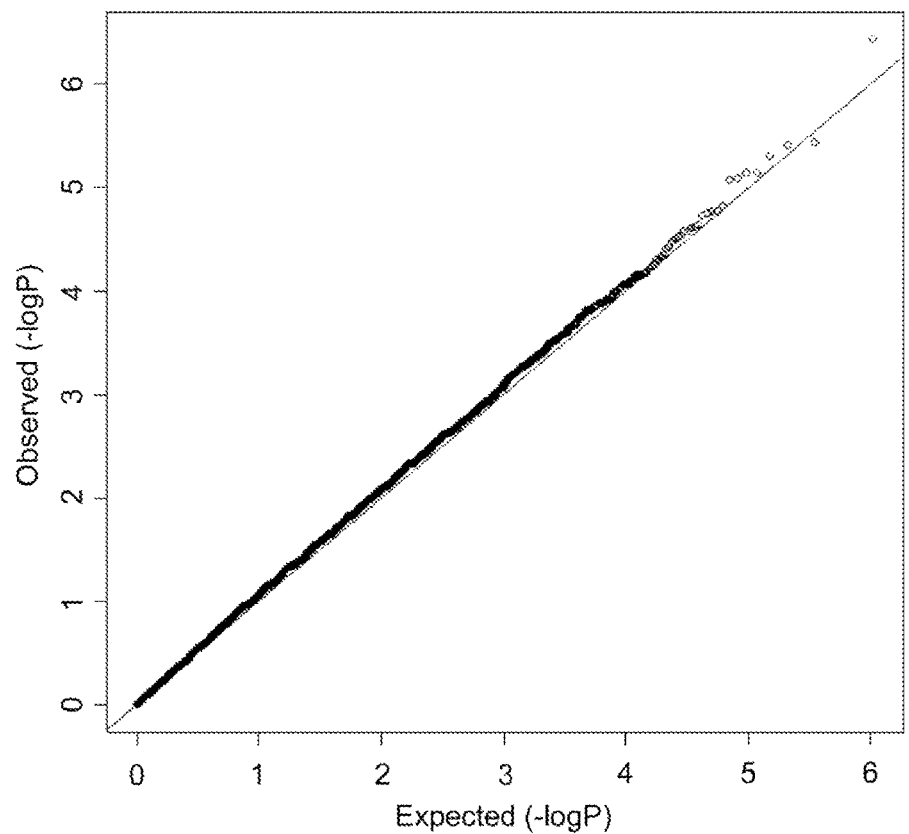
FIG. 7 shows a quantile-quantile plot for Phase I analysis. Observed P-values of SNPs against the theoretical distribution of expected p-values were plotted from the Phase I analysis. A total of 525,220 SNPs from the Phase I Illumina 550K platform were used to generate a plot.

Genome-wide association analysis was performed in PLINK (Purcell et al. (2007) Am. J. Hum. Genet. 81:559-575) using an additive logistic regression model to measure the association between each SNP and an improvement in ejection fraction of greater than 20% compared to control patients who had undergone transplant. Cases and controls were matched by age, sex and race, and no further adjustment was made for these covariates. A Manhattan plot of −log 10P was generated using Haploview (FIG. 6). Values for a quantile-quantile plot were generated using PLINK to evaluate the potential impact of population stratification (FIG. 7). Odds ratio (OR) values were measured as OR per minor allele of each SNP. The threshold for statistical (genome-wide) significance was estimated at $5\times10^{-8}$.

Differential Gene Expression

Microarray gene expression data was collected from every publicly available human myocardial dataset (n=340) in the Gene Expression Omnibus database (ncbi.nlm.nih.gov/geo/). Experimental conditions and identifiable phenotypes from each dataset were also extracted. Data normalization was performed using a median-absolute-deviation algorithm (Smyth et al. (2003) Methods 31:265-273) to allow comparison of gene expression between different platforms and experimental conditions. Gene expression data were combined and normalized using the median-absolute-deviation algorithm as described. To assess for differences in gene expression between myopathic (n=127) tissue and control (n=213) tissue, we ran a significance analysis of microarrays (SAM) analysis (Storey et al. (2003) Methods Mol. Biol. 224:149-157) using the same module in R. The statistical metric (d-score) from this analysis was subsequently used to further inform the analyses below and to rank genes and SNPs of interest for final selection in the custom genotyping array.

Genic SNP Weighting

Genic SNPs from the Illumina 550K platform were defined as SNPs between 2,000 base pairs upstream of the gene start site and 2,000 base pairs downstream from the stop site. The p-values of each genic SNP from the informative Genome-Wide Association Study were then weighted by the d-scores of their corresponding genes from the differential gene expression analysis using the method described by Genovesce et al. (Genovese et al. (2006) Biometrika 93:509-524). The weights are assigned as follows:

$$W_i = \frac{1+(r-1)U_i}{1+(r-1)U_m}$$

where $W_i$ is the weight assigned to the SNPs of to the $i^{th}$ gene, r is the strength of the weighting desired (value of r=2 was selected), with higher values resulting in a more influential effect on the GWAS p-values, $U_i$ is the significance statistic and $U_m$ is the average value of the test statistic. The final weighted p-value was calculated as:

$p$-adjusted=$p$-unadjusted/$W_i$

The "weighted_FDR" (Roeder et al. (2007) Genetic Epidemiology 31:741-747) module in R was used to perform for this analysis.

Coexpression Network

Pair-wise gene-gene adjacencies were calculated by raising the pair-wise pearson correlation to an exponent of nine, where corn is the pearson correlation and $A_{ij}$ is the adjacency between gene$_i$ and gene$_j$:

$$A_{ij}=\text{corr}(\text{gene}_i,\text{gene}_j)^9 \qquad (1)$$

This scaling exponent was empirically found to produce adjacencies that best satisfied approximate scale free topology (Jeong et al. (2000) Nature 407:651-654). Genes were clustered using average linkage hierarchical clustering and adaptively assigned to modules using the dynamic tree cut algorithm developed by Horvath, et al. (Langfelder et al. (2008) Bioinformatics 24:719-720). Mean intra-modular connectivities were calculated for each gene in each module from the intramodular adjacency, where $K_{in(i)}$ is the intra-modular connectivity for gene, and $A_{ij}$ is the adjacency calculated as above, and N is the number of genes in the module:

$$K_{in(i)}=(\Sigma_{j\neq i}A_{ij})/(N-1) \qquad (2)$$

The gene in each module with the maximum intra-modular connectivity was subsequently chosen as the module hub gene. We then identified gene modules that exhibited significant differential expression between normal and failing human myocardium. To this end, gene modules were ranked according to the average significance of differential expression between normal and failing myocardium, or d-score (see above), of the module genes. Hub genes for the top 65 modules ranked in this manner were chosen for single-nucleotide polymorphism selection.

Semantic Network

The building of a gene-gene interaction network was automated using semantic mining of publicly available literature as previously described (Ashley et al. (2006) Circulation 114:2644-2654; King et al. (2005) Physiological Genomics 23:103-118). Publicly available Pubmed abstracts were retrieved and a search was performed for sentences containing 19,000 gene/protein terms from the gene expression microarray platforms. When multiple gene terms appear in the same sentence with an intervening verb suggestive of a relationship, such as "upregulates", "inhibits", or "binds to", an interaction is established. 9,404 genes/proteins were found to have at least one semantic interaction and a total of over 54,000 gene-gene interactions were established. The 3,514 subnetworks with fewer than 6 members were excluded from further analysis. The differential gene expression analysis described above was used to rank the semantic subnetworks by averaging the absolute d-scores of the members in each subnet. Hub genes from the top 200 modules ranked in this manner were considered for customized gene array SNP selection.

Candidate Gene Selection

Candidate genes were selected for consideration for inclusion in the custom array from a number of sources. Genes known to be direct targets of the pharmacologic agents used in heart failure treatment, their downstream targets, and associated downstream pathways were included. Additionally, genes known to be involved in alteration of pharmacodynamics of therapeutics for heart failure were included. Genes involved in the renin-angiotensin-aldosterone and adrenergic stimulation pathways were specifically included. A set of genes representing genes known to be responsible for monogenic, familial forms of dilated cardiomyopathy and associated members of the membrane cytoskeletal linkage and Z-disc complexes were also included. Furthermore, genes known to be involved in alteration of calcium handling and energetics were included.

Selection of SNPs from Candidate and Network Genes

A list of genes for consideration to include on the customized array was generated as described above. In order to select single nucleotide polymorphisms for these genes, we queried the Genome Variation Server (gvs.gs.washington.edu/GVS/) for tagged SNPs. We specified a Minor Allele Frequency cutoff of 0.2 from the CEU HapMap population to improve relevance of selected SNPs to our customized array genotyped population. Each candidate, hub, and nexus gene, including 5000 base pairs up and downstream from the 5' and 3' untranslated regions, was queried for tagged SNPs meeting the MAF cutoff. SNPs were selected with the tagSNP algorithm with an $r^2$ threshold of 0.8, minimum data coverage of 0.85, and minimum data coverage for clustering of 0.70. SNPs selected were then ranked by the weighted p-value from the informative GWA study. SNPs not represented on the Illumina 550K chip were excluded for further evaluation. In case of multiple SNPs within the same bin, the highest p-value followed by the highest MAF was used to rank within-bin SNPs, and only the highest-ranked SNP was selected. After selection within individual bins, tagged SNPs from each gene were ranked first by weighted p-value followed by MAF. For each gene, a maximum of five SNPs were selected, with a maximum informative GWA p-value of 0.5 for hub and nexus gene SNPs and 0.05 for candidate gene SNPs.

Previously Identified SNPs

Literature reviews were performed evaluating evidence for and against associations between beta-blocker, ACE-inhibitor, aldosterone antagonist, anti-arrhythmics, and known candidate gene polymorphisms (Wheeler et al. (2008) J. Cardiovasc. Transl. Res. 1:25-36; Perez et al. (2008) J. Cardiovasc. Transl. Res. 1:155-165). Highly significant polymorphisms identified in previous genome wide association studies of coronary artery disease, diabetes mellitus, nicotine dependence, and atrial fibrillation were similarly catalogued. Additionally, SNPs identified in the Framingham Heart Study GWA associated with echocardiographic findings of LV size and wall thickness were catalogued (Larson et al. (2007) BMC Medical Genetics 8 Suppl. 1:S5). SNPs identified via candidate gene sequencing (Cardiogenomics) and found to be associated with LV size and ejection fraction with p<0.0001 in at least one comparison were further catalogued for consideration (NHLBI Program for Genomic Applications HMS. Genomics of cardiovascular development, adaptation, and remodeling. 2010).

MicroRNA Gene Polymorphisms

MicroRNAs are a unique and recently described class of transcribed RNAs that are involved in post-transcriptional regulation of mRNA via targeted degradation. Fully thirty percent of genes are thought to be targets for microRNA-mediated regulation. Recent studies suggest microRNAs may have a significant role in the stress response to hypertrophy. We included microRNAs in our candidate gene search due to this potentially significant role in altering gene expression. Human microRNAs were catalogued from the most recently available microRNA database, miRbase (microrna.sanger.ac.uk/). Tagged SNPs were identified for genes encoding microRNAs using the chromosome locations as found on miRbase and 1000 base pairs up and downstream.

Final SNP Selection for Custom Array

A target of 1,536 SNPs was chosen for the creation of a customized gene array. The overall strategy was to assign approximately one third of the array to intergenic SNPs, one third to genic SNPs and one third to SNPs ascertained from the network analyses and curated lists (FIG. 1B). Unless otherwise noted above, SNPs from each category were excluded if the SNP quality scores, representing likelihood of successful genotyping on the GoldenGate platform, were <0.6 or if there was a representative SNP in linkage disequilibrium, with $r^2$>0.8, already selected for inclusion. The top 561 SNPs from the weighted informative GWA genic SNP analysis that met these criteria were selected (Group A). The top 540 intergenic SNPs, defined as SNPs lying further than 5000 base pairs up or downstream from the untranslated 3' and 5' regions, were also selected for custom array inclusion (Group D). SNPs from groups A and D that had CEU HapMap minor allele frequencies<20% were excluded. The top 264 SNPs from the coexpression and semantic network analyses were selected (Group B). The final 171 SNPs were selected from the curated candidate genes and candidate SNPs as well as microRNA polymorphisms (Group C). Furthermore, SNPs selected from group C that had an informative GWA p-value of greater than 0.5 were excluded.

Custom SNV Array Analysis

Figure 5:
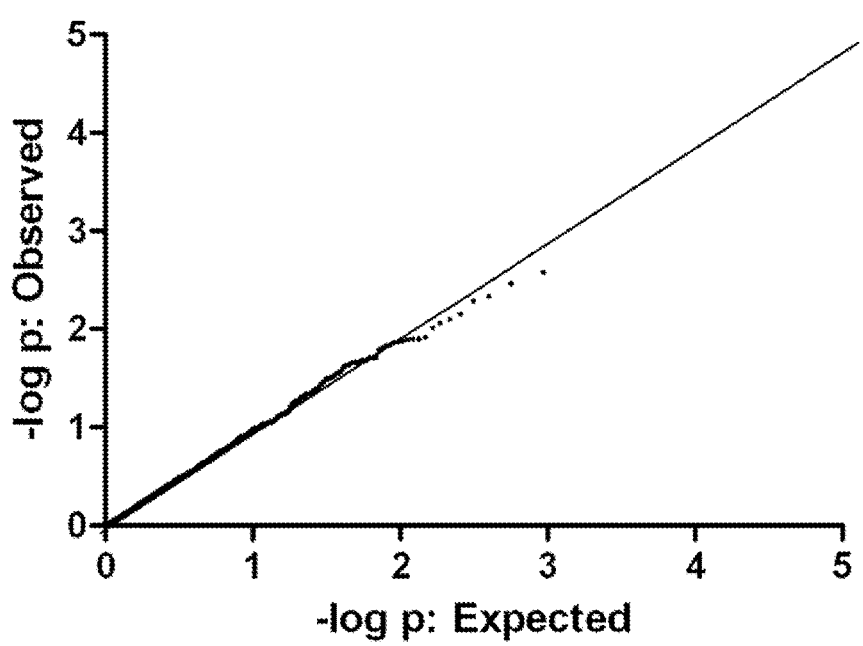
FIG. 5 shows a quantile-quantile plot for Phase II analysis. Observed P-values of SNPs against the theoretical distribution of expected p-values were plotted from the Phase II analysis. A total of 1366 SNPs from the Phase II customized array were used to generate a plot.

Custom array analysis was performed in PLINK using a multivariate additive logistic regression model to measure the association between each SNP and an improvement in ejection fraction of greater than 10% compared to those without documentation of such an improvement. This association was adjusted for age, sex and race. A Manhattan plot of $-\log 10P$ was generated using Haploview (FIG. 2A). Values for a quantile-quantile plot were generated using PLINK to evaluate the potential impact of population stratification (FIG. 5). OR values were measured as OR per minor allele of each SNP. The threshold for statistical significance was estimated at the Bonferroni-corrected value of $0.05/1402=3.56\times10^{-5}$.

P-values from the informative GWA and custom gene array were meta-analyzed with a weighted Z-method (Whitlock (2005) J. Evol. Biol. 18:1368-1373) using Stouffer's Z trend, which considers sample size and effect directions, in MetaP (compute1.lsrc.duke.edu/softwares/MetaP/metap.php).

UPenn Association Analysis

Analysis of the replication genotyping in the UPenn cohort was performed in SAS (v9.1) using a multivariate additive logistic regression model to measure association between the rs7767652 genotype and a baseline EF≥35% compared to a baseline EF<35%. The association was adjusted for age, sex, hypertension, diabetes, renal function (glomerular filtration rate) and body mass index. The odds ratio (OR) was measured as OR per minor allele. The threshold for statistical significance in this single replication association was 0.05.

Functional Assays

Allele-Specific Gene Expression

Oligonucleotides containing the putative regulatory elements for rs7767652-C and rs7767652-T were generated by annealing the following single-stranded sequences (rs7767652-C forward: 5'-AGCT (TTATAAT-CAAAGAAAG)x4-3' (SEQ ID NO:2) and rs7767652-C reverse: 5'-GATC (CTTTCTTTGATTATAA)x4-3' (SEQ ID NO:3); rs7767652-T forward: 5'-AGCT (TTATAAT-TAAAGAAA)x4-3' (SEQ ID NO:4) and rs7767652-T reverse: 5'-GATC TTTCTTTAATTATAA)x4-3' SEQ ID NO:5) at 95 degrees for 10 minutes in annealing buffer and allowed to cool to room temperature. Double-stranded DNA fragments were then directionally subcloned into the multiple cloning site (MCS) of pLuc-MCS vector driven by a minimal promoter (Agilent). Constructs were validated by Sanger sequencing. Empty vector (pLuc-MCS), rs7767652-C or rs7767652-T and Renilla luciferase constructs, as well as empty expression construct (pcDNA3.1-CMV), human TCF4 and human β-catenin, or human TCF4Δ30 and β-catenin expression constructs were transfected into either C2C12, H9c2 or HEK cell lines using Lipofectamine 2000 (Life Technologies). Cells were maintained in complete Dulbecco's Modified Eagle Medium (DMEM) containing low glucose, sodium pyruvate and L-glutamine (Life Technologies) and supplemented with 10% fetal bovine serum. Media was replaced after 6 hours, and dual-luciferase activity was measured after 24 hours using a SpectraMax L luminometer (Molecular Devices). Relative luciferase activity (firefly/Renilla luciferase ratio) is expressed as the fold change of the empty vector control (pLuc-MCS) with the empty expression construct (Empty).

HCRTR2 Gene Expression

The HCRTR2 gene expression values were collected from human left ventricular myocardial gene expression datasets in the Gene Expression Omnibus (GEO) database that were performed on the Affymetrix UA133A or UA133 Plus 2.0 arrays. Samples were identified as being control, non-ischemic (dilated) cardiomyopathy, or ischemic cardiomyopathy. For paired samples from trials with an intervention (such as LVAD placement), only data from the pre-intervention sample was used. Individual datasets were accessed and collated by probe ID, and the combined data set was quantile-normalized using the limma package in R (function normalizeBetweenArrays). Samples without valid calls for HCRTR2 were removed. We then compared the mean gene expression values, reported as ratios of probe fluorescence to background fluorescence, between normal tissue and dilated cardiomyopathic tissue or ischemic cardiomyopathic tissue. The association between expression values and disease status was tested using Student's t-test in R.

Transcription-Disrupted and Knockout Mice

Wild-type C57BL/6 14-week-old mice were obtained from Charles River International (Wilmington, Mass.). HCRTR2 transcription-disrupted (TD) mice were produced by inserting a loxP-flanked gene cassette into intron 1, 137 bp upstream of exon 2 which disrupted production of HCRTR2 in mice with a C57BL/6 background (Mochizuki et al., supra). These mice were provided courtesy of Dr. Thommas Scammell (Harvard Medical School) who previously demonstrated a lack of normal HCRTR2 expression in the TD mice (Mochizuki et al., supra). HCRTR2 knockout mice were created using a targeting vector to replace exon 1 with lac-Z and neo cassettes by homologous recombination in a C57BL/6J background (Chemelli et al., supra). These mice were provided courtesy of Dr. Priyattam Shiromani (Medical University of South Carolina).

Minipump Experiments

Experimental mice were anesthetized with 1.5% isoflurane by a facemask. The Alzet osmotic minipumps (Model 2002 or 2004) from the Alzet Corporation (Cupertino, Calif., USA) were implanted subcutaneously in the back of mice, posterior to the scapulae. 14-week-old C57BL/6 mice were treated with either saline or orexin A (50 μg/kg/day) infusions using an Alzet (Cupertino, Calif.) osmotic minipump model 2004 (200 μl reservoir, 28-day release at 0.25 μl/hr) for a total of 4 weeks. At week 2, all mice were treated with angiotensin II (1.4 mg/kg/day) plus isoproterenol (15 mg/kg/day) infusion using an additional Alzet osmotic minipump, model 2002 (200 μl reservoir, 14-day release at 0.5 μl/hr) for two weeks, starting 2 weeks after initiation of the saline or orexin A infusion. Mice had echocardiography performed at baseline and weeks 2, 3 and 4.

Murine Echocardiography

For noninvasive echocardiography, mice were anesthetized with isoflurane via nose cone (maintenance: 1.5% isoflurane mixed with 1 L/minute 100% medical oxygen to obtain heart rate of 450±50 beats per minute). Mouse body temperature was monitored with a rectal thermometer. The chest was shaved using a Nair lotion hair remover (Church & Dwight Canada, Mississauga, ON, Canada). Electrode gel was put to the four paws and tape them to the ECG electrodes. Two-dimensional, pulse Doppler and tissue Doppler flow echocardiography were performed with Vevo 2100 High-Resolution In Vivo Imaging System (VisualSonics, Toronto, ON, Canada) which has an MS550D microscan transducer with an operating frequency band of 22-55 MHz. To minimize bias, echocardiographs were performed blinded to drug infusion status.

Two-dimensional imaging (B-mode) was used to obtain a view of left and right ventricular movement during diastole and systole along the parasternal short axis. M-mode echocardiography was used to obtain measurements of cardiac dimensions including left ventricular internal diastolic and systolic dimensions, which were used to estimate ejection fraction, as well as septal and left ventricular posterior wall thickness. Pulsed-wave Doppler and tissue Doppler echocardiography analyses were used to evaluate diastolic function. Pulsed-wave Doppler images were used to record the trans-mitral Doppler blood flow velocities. Early (E) wave was measured as the peak velocity during filling of the ventricle, and atrial (A) wave was measured as the peak velocity during atrial contraction, at the end of diastole. Tissue Doppler imaging was used to record the peak mitral annular relaxation velocity (F) during diastole. All data and images were saved and analyzed using a Vevo 2100 advanced cardiovascular package software with a semi-automated quantification of cardiac function (V 1.4.0 VisualSonics, Toronto, ON, Canada).

Murine Exercise Capacity

Maximum exercise capacity was measured by using a 4-channel rodent treadmill equipped with an electrical stimulus and metabolic analyzers to measure $O_2$ and $CO_2$ gas fractions. (Accuscan Instruments, now Omnitech Electronics, Columbus, Ohio, USA). Mice were familiarized with running on the treadmill before exercise testing. The exercise protocol consisted of a progressive increase in treadmill speed from 5-22.5 m/minute and incline from 0-15 degrees at 3 minute intervals until the mice reached exhaustion. The point of exhaustion was determined by the observation that mice could not keep up with the pace of the treadmill and had no response to the electrical stimulus. The reference and cage flow rate was maintained at 0.5 l/m. The flow rate, $O_2\%$ and $CO_2\%$ of the reference and individual cage were monitored for 30 seconds at 2 minute intervals and recorded with Fusion software (version 3.9). Exercise capacity was assessed by measuring peak $VO_2$.

Histologic Analysis

Freshly dissected heart tissues were fixed with 4% paraformaldehyde, dehydrated, embedded in paraffin and sectioned at 4 μm (Stanford Comparative Medicine Histology Lab). After deparaffinization and rehydration, myocardial sections were stained with Masson's trichrome stain. Digital images were acquired at 20× magnification using a Nikon 90i microscope with camera. For degree of fibrosis, blue/red ratios were estimated using RGB histograms from the Masson trichrome-stained sections analyzed in Photoshop CS6 (version 13.0).

TABLE 1

Baseline demographic and clinical characteristics of Phase I and Phase II heart failure cohorts.

| | Phase I | | | | Phase II | | | |
|---|---|---|---|---|---|---|---|---|
| Characteristic | Overall n = 66 | Δ EF ≥20% n = 29 | Transplant n = 37 | p* | Overall n = 591 | Δ EF ≥10% n = 137 | Δ EF <10% n = 454 | p** |
| Age (years) | 60.6 ± 11.0 | 62.1 ± 13.1 | 59.4 ± 9.1 | 0.35 | 59.0 ± 15.5 | 56.9 ± 14.3 | 59.6 ± 15.8 | 0.071 |
| Female | 25 (37.9) | 12 (41.4) | 13 (35.1) | 0.60 | 169 (28.6) | 48 (35.0) | 121 (26.7) | 0.059 |
| African American | — | — | — | — | 43 (7.3) | 10 (7.3) | 33 (7.2) | 0.99 |
| Hispanic | — | — | — | — | 12 (2.0) | 4 (2.9) | 8 (1.8) | 0.40 |
| Asian | — | — | — | — | 26 (4.4) | 5 (3.6) | 21 (4.6) | 0.63 |
| Baseline EF (%) | 27.8 ± 11.3 | 29.2 ± 10.7 | 26.7 ± 11.8 | 0.40 | 34.2 ± 14 | 29.0 ± 11.5 | 36.4 ± 14.6 | <0.0001 |
| NYHA Class III-IV | 29 (43.9) | 16 (55.2) | 13 (35.1) | 0.10 | 199 (42.1) | 53 (42.0) | 146 (42.2) | 0.16 |
| Coronary Disease | 18 (27.2) | 6 (20.7) | 12 (32.4) | 0.29 | 222 (37.6) | 35 (25.5) | 187 (41.2) | 0.0009 |
| CABG | 9 (13.6) | 5 (17.2) | 4 (10.8) | 0.45 | 123 (20.8) | 20 (14.6) | 103 (22.7) | 0.041 |
| Atrial Fibrillation | 18 (27.2) | 8 (27.6) | 10 (27.0) | 0.96 | 173 (29.3) | 40 (29.2) | 133 (29.3) | 0.98 |
| Diabetes | 19 (28.8) | 14 (48.2) | 5 (13.5) | 0.002 | 126 (21.3) | 36 (26.3) | 90 (19.8) | 0.11 |
| Hypertension | 17 (25.8) | 11 (37.9) | 6 (16.2) | 0.045 | 234 (39.6) | 55 (40.1) | 179 (39.4) | 0.88 |
| Device Implant | 25 (37.9) | 9 (31.0) | 16 (43.2) | 0.31 | 305 (51.6) | 80 (58.4) | 225 (49.6) | 0.070 |
| On Beta Blocker | 48 (72.7) | 22 (75.9) | 26 (70.2) | 0.61 | 410 (69.4) | 127 (92.7) | 283 (62.3) | <0.0001 |
| On ACE-I | 38 (57.6) | 17 (58.6) | 21 (56.8) | 0.88 | 274 (46.4) | 70 (51.1) | 204 (45.0) | 0.21 |
| On ARB | 12 (18.2) | 4 (13.8) | 8 (21.6) | 0.41 | 81 (13.7) | 22 (16.1) | 59 (13.0) | 0.36 |
| On Antiarrhythmic | 8 (12.1) | 2 (6.9) | 6 (16.2) | 0.25 | 105 (17.8) | 19 (13.9) | 86 (18.9) | 0.17 |
| On CCB | 0 | 0 | 0 | — | 10 (1.7) | 5 (3.7) | 5 (1.1) | 0.0427 |

Values are presented as total number (percentage of subjects) or mean ± standard deviation.
EF = ejection fraction,
NYHA Class III-IV = New York Heart Association heart failure severity class III or IV at baseline,
CABG = coronary artery bypass grafting,
ACE-I = angiotensin converting enzyme inhibitor,
ARB = angiotensin receptor blocker,
CCB = calcium channel blocker.
Δ EF ≥20% and Δ EF ≥10% represent patients whose EF improved by an absolute value greater than 20 or 10 percentage points, respectively.
Transplant patients are those with decompensation in their clinical status despite medical intervention and required heart transplantation.
*P-values represent significance from the t-test for continuous variables and chi-square test for categorical variables between those with an improvement in EF by 20 percentage points and those who underwent transplant.
**P-value for differences between those whose EF improved by 10 percentage points and those without such an improvement.

TABLE 2

Summary of association results for ejection fraction response in the Phase I and Phase II heart failure cohorts.

| | | | | Phase I | | | | Phase II | | | | |
|---|---|---|---|---|---|---|---|---|---|---|---|---|
| SNP | Minor Allele | Candidate Gene | Source | Δ EF ≥20% (n = 29) MAF | Transplant (n = 37) MAF | OR | p | Δ EF ≥10% (n = 137) MAF | Δ EF <10% (n = 454) MAF | OR | p | Combined p |
| Top Overall SNPs | | | | | | | | | | | | |
| rs7767652 | T | HCRTR2 | D | 0.14 | 0.36 | 0.28 | 0.0040 | 0.11 | 0.24 | 0.394 | $3.29 \times 10^{-5}$ | $9.04 \times 10^{-6}$ |
| rs2527366 | G | GTF2I | A | 0.45 | 0.26 | 2.35 | 0.016 | 0.39 | 0.29 | 1.728 | 0.00065 | 0.0003 |
| rs4901426 | A | DDHD1 | D | 0.31 | 0.63 | 0.27 | 0.0025 | 0.52 | 0.43 | 1.54 | 0.00383 | 0.0085 |
| rs1936602 | A | HTR7 | D | 0.60 | 0.30 | 3.60 | 0.0020 | 0.38 | 0.49 | 0.67 | 0.00650 | 0.0177 |
| rs3813089 | T | MRO | B | 0.22 | 0.18 | 1.36 | 0.465 | 0.31 | 0.23 | 1.60 | 0.00748 | 0.0062 |
| rs1546120 | T | MAD2L1 | A | 0.12 | 0.30 | 0.32 | 0.0130 | 0.19 | 0.27 | 0.61 | 0.00799 | 0.0037 |

TABLE 2-continued

Summary of association results for ejection fraction response in the Phase I and Phase II heart failure cohorts.

Top Curated SNPs

| | | | | | | | | | | | | |
|---|---|---|---|---|---|---|---|---|---|---|---|---|
| rs8096199 | G | DLGAP1 | C-Can | — | — | — | — | 0.220 | 0.161 | 1.616 | 0.00902 | 0.0090 |
| rs1799983 | T | NOS3 | C-Can | — | — | — | — | 0.359 | 0.277 | 1.449 | 0.01504 | 0.01504 |
| rs767757 | G | PRKCH | C-Path | 0.362 | 0.216 | 2.057 | 0.0485 | 0.448 | 0.385 | 1.367 | 0.042 | 0.0254 |
| rs7220007 | A | PRKCA | C-Can | 0.603 | 0.378 | 2.5 | 0.0151 | 0.528 | 0.444 | 1.362 | 0.04335 | 0.0263 |
| rs12623467 | T | N RXN1 | C-GWA | — | — | — | — | 0.171 | 0.128 | 1.612 | 0.0267 | 0.0267 |
| rs7903146 | T | TCF7L2 | C-GWA | 0.362 | 0.284 | 1.432 | 0.364 | 0.354 | 0.292 | 1.377 | 0.04691 | 0.0381 |
| rs10511311 | T | CD200 | C-GWA | — | — | — | — | 0.409 | 0.336 | 1.342 | 0.04834 | 0.04834 |

Replication

Penn Heart Failure Study

| | | | | EF ≥35% (n = 333) MAF | EF <35% (n = 464) MAF | OR | p |
|---|---|---|---|---|---|---|---|
| rs7767652 | T | HCRTR2 | Penn | .209 | 0.247 | 0.769 | 0.021 |

Top Overall SNPs are the common variants from the customized heart failure gene array with the lowest p-values. The Top Curated SNPs are the variants with the lowest p-values from a subset of variants on the customized array that had been manually pre-selected. The Phase I cohort was age, sex and race-matched. Phase II analyses were adjusted for age, sex and race.
Δ EF ≥20% and Δ EF ≥10% represent patients whose EF improved by an absolute value greater than 20 or 10 percentage points, respectively.
Transplant patients are those with decompensation in their clinical status despite medical intervention and required heart transplantation. The Penn Heart Failure replication analysis was adjusted for age, sex, hypertension, diabetes, renal function (glomerular filtration rate) and body mass index.
MAF = minor allele frequency,
OR = odds ratio per minor allele,
EF = ejection fraction,
Source = group from which the variant was selected for placement on the customized array: D = Top Intergenic SNPs from phase I GWAS, A = Top weighted SNPs from phase I GWAS, B-Hub = Coexpression network analysis gene hub.
C-can = candidate SNPs from prior studies,
C-Path: variant in gene responsible for important disease pathway,
C-GWA = SNPs associated with relevant phenotypes in prior studies.

TABLE 3

Weighted (Group) SNPs: Summary of association results for ejection fraction response in the Phase I cohort weighted by gene expression analysis statistical values (d-scores), and unweighted Phase II association results.

| SNP | Candidate Gene | Minor Allele | Phase I OR | Phase I p-value | d-score | Weight | Adjusted Phase I | Phase II pOR | Phase II p-value |
|---|---|---|---|---|---|---|---|---|---|
| Top SNPs Ranked by Phase I Weighted p-values | | | | | | | | | |
| rs11780576 | PSD3 | C | 0.22 | 0.000461 | 5.16 | 3.94 | 0.000117 | 1.08 | 0.6085 |
| rs6444661 | C3orf59 | T | 4.36 | 0.000436 | 3.21 | 3.5 | 0.000125 | 1.28 | 0.1171 |
| rs6061052 | PDRG1 | G | 4.38 | 0.000496 | 4.5 | 3.92 | 0.000126 | 0.86 | 0.3514 |
| rs6917833 | C6orf192 | C | 4.11 | 0.000616 | 2.42 | 2.61 | 0.000236 | 1.23 | 0.178 |
| rs6444668 | C3orf59 | T | 3.82 | 0.000858 | 3.21 | 3.5 | 0.000245 | 0.91 | 0.5232 |
| rs1959152 | BAZ1A | T | 3.67 | 0.001062 | 9.87 | 3.95 | 0.000269 | 1.07 | 0.6641 |
| rs588361 | RPUSD4 | G | 0.26 | 0.001254 | 4.36 | 3.91 | 0.000321 | 1.1 | 0.5994 |
| rs10513287 | ASTN2 | G | 0.25 | 0.001287 | 7.09 | 3.95 | 0.000326 | 1.08 | 0.6182 |
| rs2074267 | ILVBL | C | 0.29 | 0.001284 | 4.21 | 3.89 | 0.00033 | 0.8 | 0.1853 |
| rs11731086 | KIAA0746 | G | 6.37 | 0.000123 | 0.65 | 0.35 | 0.000349 | 1.12 | 0.4816 |
| rs602735 | RPUSD4 | C | 0.25 | 0.001371 | 4.36 | 3.91 | 0.000351 | 0.9 | 0.566 |
| rs2900367 | DERA | C | 0.25 | 0.001396 | 5.81 | 3.95 | 0.000354 | 1.21 | 0.2143 |
| rs1049523 | CYB5D2 | G | 5.04 | 0.001302 | 3.49 | 3.67 | 0.000354 | 1.23 | 0.2094 |
| rs6990300 | TNKS | G | 0.23 | 0.001297 | 3.29 | 3.56 | 0.000365 | 0.94 | 0.6812 |
| rs35000 | RASGRF2 | A | 3.48 | 0.001491 | 3.39 | 3.62 | 0.000412 | 1.06 | 0.6942 |
| rs7142040 | BAZ1A | A | 3.24 | 0.001666 | 9.87 | 3.95 | 0.000422 | 1.04 | 0.8038 |
| rs9876221 | C3orf59 | G | 3.41 | 0.001494 | 3.21 | 3.5 | 0.000427 | 1.08 | 0.6291 |
| rs7773338 | C6orf192 | C | 0.27 | 0.001206 | 2.42 | 2.61 | 0.000462 | 0.83 | 0.2141 |
| rs4838267 | ASTN2 | G | 0.25 | 0.001858 | 7.09 | 3.95 | 0.000471 | 0.99 | 0.9371 |
| Top SNPs Ranked by Phase II unweighted p-values | | | | | | | | | |
| rs2527366 | GTF2I | G | 2.35 | 0.0164 | 3.33 | 3.58 | 0.004576 | 1.73 | 0.000648 |
| rs1546120 | MAD2L1 | T | 0.32 | 0.01299 | 8.65 | 3.95 | 0.003293 | 0.61 | 0.007993 |
| rs7126330 | KCNQ1 | T | 0.36 | 0.006945 | 1.5 | 1.21 | 0.005723 | 1.45 | 0.01217 |
| rs1023181 | PCSK5 | G | 2.56 | 0.02158 | 5.9 | 3.95 | 0.00547 | 1.45 | 0.01393 |
| rs2598414 | SRP68 | T | 2.36 | 0.01924 | 9.45 | 3.95 | 0.004877 | 1.42 | 0.01472 |
| rs1439977 | ZAK | A | 2.9 | 0.003726 | 9.46 | 3.95 | 0.000944 | 1.42 | 0.01775 |
| rs4948383 | ANK3 | G | 3.25 | 0.01075 | 4.33 | 3.91 | 0.002752 | 1.45 | 0.02178 |
| rs1141371 | PTPRS | C | 2.88 | 0.02253 | 6.3 | 3.95 | 0.005711 | 1.42 | 0.02187 |
| rs8021281 | SAMD4A | C | 0.33 | 0.006963 | 2.09 | 2.11 | 0.003302 | 1.46 | 0.03121 |
| rs2272935 | NPAL3 | T | 3.25 | 0.01908 | 9.84 | 3.95 | 0.004836 | 1.4 | 0.03137 |

TABLE 3-continued

Weighted (Group) SNPs: Summary of association results for ejection fraction response in the Phase I cohort weighted by gene expression analysis statistical values (d-scores), and unweighted Phase II association results.

| SNP | Candidate Gene | Minor Allele | Phase I OR | Phase I p-value | d-score | Weight | Adjusted Phase I | Phase II pOR | Phase II p-value |
|---|---|---|---|---|---|---|---|---|---|
| rs709529 | BBX | C | 0.42 | 0.02494 | 3.65 | 3.75 | 0.006649 | 0.71 | 0.03343 |
| rs501014 | AGL | C | 3.25 | 0.01153 | 2.51 | 2.74 | 0.004216 | 0.7 | 0.0369 |
| rs740058 | PTPRS | G | 0.33 | 0.007253 | 6.3 | 3.95 | 0.001838 | 0.68 | 0.03841 |
| rs177421 | PCQAP | A | 3.96 | 0.003005 | 1.78 | 1.62 | 0.001852 | 0.73 | 0.04074 |
| rs511145 | RAB22A | C | 0.39 | 0.01451 | 2.43 | 2.62 | 0.005529 | 1.33 | 0.05265 |
| rs13417370 | KBTBD10 | G | 0.41 | 0.01682 | 2.59 | 2.85 | 0.005893 | 0.74 | 0.05795 |
| rs6560488 | PCSK5 | A | 2.55 | 0.02434 | 5.9 | 3.95 | 0.00617 | 1.31 | 0.06574 |
| rs1858801 | ATBF1 | A | 2.33 | 0.01974 | 3.93 | 3.84 | 0.005142 | 0.77 | 0.07262 |
| rs1564943 | MICAL2 | C | 0.4 | 0.01645 | 4.12 | 3.88 | 0.004241 | 1.3 | 0.0766 |
| rs41121 | FAM81B | C | 0.32 | 0.02558 | 4.4 | 3.91 | 0.006538 | 0.74 | 0.07832 |

The Phase I cohort was age, sex and race-matched. Phase I analyses tested associations for EF improvement by an absolute value greater than 20 percentage points using an additive logistic regression model. Phase II analyses tested associations for EF improvement by an absolute value greater than 10 percentage points using an additive logistic regression model adjusted for age, sex and race. d-score was the statistical value from the analysis comparing gene expression in heart failure tissue versus normal heart tissue. Weight is the weighted value based on the d-score that was used to adjust the Phase I p-value.
OR = odds ratio per minor allele,
EF = ejection fraction.

TABLE 4

Intergenic (Group D) SNPs: Summary of association results for ejection fraction response in the Phase I and Phase II heart failure cohorts.

| SNP | Candidate Gene | Minor Allele | Phase I Δ EF ≥20% (n = 29) MAF | Transplant (n = 37) MAF | OR | p | Phase II Δ EF ≥10% (n = 137) MAF | Δ EF <10% (n = 454) MAF | OR | p |
|---|---|---|---|---|---|---|---|---|---|---|
| *Top SNPs Ranked by Phase I p-values* |
| rs421500 | RPS12 | G | 0.57 | 0.15 | 7.56 | 0.000069 | 0.44 | 0.41 | 1.13 | 0.4396 |
| rs6075459 | SLC24A3 | A | 0.45 | 0.12 | 5.87 | 0.0001811 | 0.26 | 0.25 | 1.08 | 0.6731 |
| rs525153 | RPS12 | T | 0.4 | 0.12 | 4.75 | 0.0001895 | 0.32 | 0.26 | 1.32 | 0.08576 |
| rs7422405 | ATP6V1C2 | A | 0.64 | 0.24 | 5.48 | 0.0002242 | 0.46 | 0.45 | 1.06 | 0.7016 |
| rs989547 | DAPK2 | T | 0.21 | 0.58 | 0.19 | 0.0003092 | 0.41 | 0.46 | 0.84 | 0.2296 |
| rs12337993 | BNC2 | T | 0.07 | 0.35 | 0.14 | 0.0003258 | 0.15 | 0.21 | 0.68 | 0.05336 |
| rs9829987 | EPHA3 | T | 0.57 | 0.24 | 4.12 | 0.0003757 | 0.44 | 0.39 | 1.26 | 0.118 |
| rs6449652 | HTR1A | C | 0.59 | 0.23 | 4.75 | 0.0003876 | 0.38 | 0.35 | 1.15 | 0.3272 |
| rs1319025 | ANXA2P3 | C | 0.66 | 0.34 | 3.72 | 0.0004225 | 0.5 | 0.44 | 1.28 | 0.1085 |
| rs878421 | GPR20 | C | 0.07 | 0.35 | 0.14 | 0.0004342 | 0.21 | 0.23 | 0.96 | 0.8267 |
| rs13228415 | NXPH1 | G | 0.43 | 0.15 | 4.34 | 0.0004359 | 0.18 | 0.21 | 0.79 | 0.2259 |
| rs1209119 | C14orf10 | A | 0.36 | 0.11 | 4.68 | 0.0004431 | 0.23 | 0.24 | 0.96 | 0.7981 |
| rs2243684 | C21orf34 | A | 0.12 | 0.43 | 0.18 | 0.000586 | 0.33 | 0.34 | 0.97 | 0.8221 |
| rs10515283 | RGMB | C | 0.36 | 0.08 | 6.43 | 0.0005937 | 0.18 | 0.16 | 1.08 | 0.6903 |
| rs6948739 | CARD11 | G | 0.22 | 0.57 | 0.22 | 0.000611 | 0.33 | 0.34 | 0.91 | 0.5702 |
| rs2069126 | SLC24A3 | T | 0.19 | 0.46 | 0.28 | 0.0006113 | 0.36 | 0.38 | 0.97 | 0.8279 |
| rs1927745 | FLJ10154 | A | 0.09 | 0.36 | 0.16 | 0.0006245 | 0.3 | 0.26 | 1.25 | 0.1507 |
| rs7041706 | BNC2 | G | 0.09 | 0.36 | 0.16 | 0.0006245 | 0.21 | 0.27 | 0.72 | 0.06813 |
| rs6081741 | SLC24A3 | G | 0.09 | 0.39 | 0.15 | 0.000638 | 0.28 | 0.3 | 0.97 | 0.8727 |
| rs9358552 | HDGFL1 | G | 0.14 | 0.42 | 0.22 | 0.000653 | 0.43 | 0.4 | 1.1 | 0.5138 |
| *Top SNPs Ranked by Phase II p-values* |
| rs7767652 | HCRTR2 | T | 0.14 | 0.36 | 0.28 | 0.004039 | 0.11 | 0.24 | 0.39 | 0.0000329 |
| rs4901426 | DDHD1 | A | 0.31 | 0.63 | 0.27 | 0.002487 | 0.52 | 0.43 | 1.54 | 0.003833 |
| rs1936602 | HTR7 | A | 0.6 | 0.3 | 3.6 | 0.00203 | 0.38 | 0.49 | 0.67 | 0.006501 |
| rs7923056 | ITGA8 | C | 0.43 | 0.2 | 2.98 | 0.005915 | 0.46 | 0.38 | 1.45 | 0.01143 |
| rs637629 | ADRBK2 | A | 0.53 | 0.23 | 3.85 | 0.003312 | 0.48 | 0.4 | 1.49 | 0.01315 |
| rs7861151 | ADAMTSL1 | G | 0.26 | 0.51 | 0.33 | 0.005119 | 0.5 | 0.41 | 1.45 | 0.01375 |
| rs1927496 | ABCC4 | G | 0.57 | 0.3 | 3.12 | 0.001695 | 0.4 | 0.47 | 0.69 | 0.01559 |
| rs4682910 | ABHD5 | T | 0.4 | 0.19 | 2.82 | 0.005401 | 0.22 | 0.29 | 0.65 | 0.01575 |
| rs9836395 | CCDC54 | G | 0.62 | 0.31 | 3.72 | 0.001339 | 0.36 | 0.27 | 1.52 | 0.01739 |
| rs1875645 | FAF1 | A | 0.28 | 0.53 | 0.34 | 0.004857 | 0.37 | 0.44 | 0.7 | 0.01754 |
| rs135893 | LDOC1L | C | 0.5 | 0.24 | 3.11 | 0.002132 | 0.35 | 0.44 | 0.7 | 0.01832 |
| rs2976271 | PPP2R2A | G | 0.52 | 0.2 | 4.21 | 0.0009619 | 0.23 | 0.31 | 0.68 | 0.02532 |
| rs13252558 | DOK2 | T | 0.14 | 0.38 | 0.26 | 0.003558 | 0.35 | 0.27 | 1.44 | 0.02587 |
| rs6696250 | TNRC4 | C | 0.63 | 0.28 | 4.21 | 0.001218 | 0.52 | 0.44 | 1.39 | 0.02721 |
| rs7759442 | C6orf118 | G | 0.14 | 0.38 | 0.26 | 0.001991 | 0.35 | 0.27 | 1.44 | 0.02911 |
| rs1323348 | ZDHHC21 | C | 0.36 | 0.15 | 3.25 | 0.005434 | 0.3 | 0.38 | 0.71 | 0.03222 |
| rs4978396 | PTPN3 | G | 0.38 | 0.15 | 3.5 | 0.003991 | 0.25 | 0.31 | 0.69 | 0.03273 |
| rs11676317 | LRRTM4 | A | 0.33 | 0.61 | 0.31 | 0.005821 | 0.42 | 0.48 | 0.72 | 0.03437 |

TABLE 4-continued

Intergenic (Group D) SNPs: Summary of association results for ejection fraction response in the Phase I and Phase II heart failure cohorts.

| SNP | Candidate Gene | Minor Allele | Phase I Δ EF ≥20% (n = 29) MAF | Transplant (n = 37) MAF | OR | p | Phase II Δ EF ≥10% (n = 137) MAF | Δ EF <10% (n = 454) MAF | OR | p |
|---|---|---|---|---|---|---|---|---|---|---|
| rs1325376 | LIG4 | G | 0.45 | 0.2 | 3.2 | 0.003911 | 0.33 | 0.25 | 1.41 | 0.03462 |
| rs973330 | TYRP1 | T | 0.6 | 0.35 | 2.81 | 0.004988 | 0.5 | 0.44 | 1.36 | 0.0398 |
| rs4262135 | LOC51334 | T | 0.57 | 0.28 | 3.37 | 0.003428 | 0.38 | 0.45 | 0.73 | 0.04131 |
| rs8008076 | FOXG1B | G | 0.45 | 0.19 | 3.48 | 0.003772 | 0.22 | 0.27 | 0.7 | 0.04182 |
| rs946481 | KIAA1026 | G | 0.22 | 0.55 | 0.23 | 0.0007618 | 0.48 | 0.44 | 1.38 | 0.04205 |
| rs2197078 | C2orf3 | C | 0.26 | 0.53 | 0.31 | 0.004852 | 0.53 | 0.47 | 1.36 | 0.0432 |
| rs4682242 | PVRL3 | A | 0.66 | 0.38 | 3.12 | 0.002765 | 0.52 | 0.45 | 1.38 | 0.04392 |
| rs8123223 | RNF24 | T | 0.57 | 0.3 | 3.12 | 0.002376 | 0.4 | 0.45 | 0.73 | 0.0464 |
| rs12589158 | SEL1L | T | 0.34 | 0.11 | 4.21 | 0.002176 | 0.15 | 0.2 | 0.67 | 0.04685 |

The Phase I cohort was age, sex and race-matched. Phase II analyses were adjusted for age, sex and race.
Δ EF ≥20% and Δ EF ≥10% represent patients whose EF improved by an absolute value greater than 20 or 10 percentage points, respectively.
Transplant patients are those with decompensation in their clinical status despite medical intervention and required heart transplantation.
MAF = minor allele frequency,
OR = odds ratio per minor allele,
EF = ejection fraction.

TABLE 5

Hub (Group B-hub) SNPs: Summary of the hubs from the coexpression modules most significantly associated with heart failure and the association results of their corresponding SNPs with ejection fraction response in the Phase I and Phase II heart failure cohorts.

| Hub Gene | Module Size | Average d-Score | SNP | Minor Allele | Phase I OR | Phase I p-value | Phase II OR | Phase II p-value |
|---|---|---|---|---|---|---|---|---|
| Top Hubs Ranked by Average Module d-score | | | | | | | | |
| SLC25A30 | 18 | 8.521 | rs4433707 | T | 1.18 | 0.4177 | 1.15 | 0.3671 |
| SLC25A30 | 18 | 8.521 | rs9526070 | C | 1.55 | 0.1842 | 0.97 | 0.8584 |
| UTP15 | 24 | 8.101 | rs13170849 | A | 1.49 | 0.3559 | 0.98 | 0.8934 |
| UTP15 | 24 | 8.101 | rs343120 | A | 0.65 | 0.3555 | 0.86 | 0.3587 |
| SLC17A1 | 29 | 7.608 | rs1165196 | C | 0.58 | 0.1096 | 0.8 | 0.1588 |
| SLC17A1 | 29 | 7.608 | rs1165210 | A | 2.67 | 0.453 | 0.93 | 0.8006 |
| SLC17A1 | 29 | 7.608 | rs3923 | A | 0.62 | 0.2992 | 1.06 | 0.6799 |
| NUMBL | 11 | 7.394 | rs2250994 | A | 0.78 | 0.4583 | 0.99 | 0.9707 |
| NUMBL | 11 | 7.394 | rs2561537 | C | 1.19 | 0.4598 | 1.1 | 0.5212 |
| LOC12475 | 47 | 7.386 | rs2430949 | A | 0.79 | 0.3497 | 0.8 | 0.2634 |
| DUS4L | 102 | 7.147 | rs6957510 | A | 3.4 | 0.2504 | 1.38 | 0.249 |
| OR8D1 | 15 | 6.88 | rs4935881 | A | 0.65 | 0.1795 | 1.07 | 0.6843 |
| C1D | 150 | 6.588 | rs4671871 | A | 1.59 | 0.4773 | 1.17 | 0.4281 |
| C1D | 150 | 6.588 | rs7582426 | G | 2.09 | 0.07674 | 1.34 | 0.07232 |
| UGT2B7 | 10 | 6.516 | rs7375178 | C | 1.83 | 0.2071 | 0.84 | 0.2596 |
| GNG3 | 17 | 6.443 | rs549312 | A | 0.57 | 0.2816 | 1.24 | 0.2148 |
| SLC2A9 | 83 | 6.439 | rs6820230 | T | 2.07 | 0.09169 | 0.75 | 0.1009 |
| SLC2A9 | 83 | 6.439 | rs6849736 | A | 0.42 | 0.448 | 1.24 | 0.3589 |
| IL1RAP | 12 | 6.267 | rs2173911 | T | 1.8 | 0.1349 | 0.94 | 0.7164 |
| IL1RAP | 12 | 6.267 | rs9682599 | C | 3.23 | 0.02459 | 1.39 | 0.1016 |
| TRIM29 | 27 | 6.196 | rs4936509 | C | 0.49 | 0.03817 | 1 | 0.9965 |
| CMTM2 | 12 | 6.168 | rs2290182 | G | 1.52 | 0.349 | 0.87 | 0.5073 |
| IQCF1 | 122 | 6.161 | rs4234645 | C | 1.85 | 0.1913 | 1.03 | 0.8563 |
| SLC37A3 | 13 | 6.147 | rs12703799 | C | 1.43 | 0.4312 | 0.87 | 0.3291 |
| Top Hubs Ranked by Phase II p-values. | | | | | | | | |
| MRO | 65 | 5.492 | rs3813089 | T | 1.36 | 0.4649 | 1.6 | 0.00748 |
| MGC61571 | 32 | 5.787 | rs7611318 | G | 1.53 | 0.354 | 1.41 | 0.02368 |
| SLC16A9 | 20 | 5.582 | rs7094971 | G | 1.81 | 0.3362 | 1.51 | 0.03891 |
| FLJ32028 | 10 | 5.127 | rs6814401 | A | 2.08 | 0.04475 | 1.37 | 0.0438 |
| DTX1 | 14 | 5.512 | rs2701623 | G | 2.04 | 0.05177 | 0.74 | 0.06716 |
| FLJ32028 | 10 | 5.127 | rs10034000 | T | 3.14 | 0.00502 | 1.33 | 0.06948 |
| C1D | 150 | 6.588 | rs7582426 | G | 2.09 | 0.07674 | 1.34 | 0.07232 |
| FBXL21 | 18 | 6.018 | rs31551 | T | 0.42 | 0.03242 | 1.31 | 0.0794 |
| MRO | 65 | 5.492 | rs2255672 | C | 0.66 | 0.4313 | 1.32 | 0.09185 |
| SLC2A9 | 83 | 6.439 | rs6820230 | T | 2.07 | 0.09169 | 0.75 | 0.1009 |
| IL1RAP | 12 | 6.267 | rs9682599 | C | 3.23 | 0.02459 | 1.39 | 0.1016 |
| MGC61571 | 32 | 5.787 | rs13085075 | T | 0.68 | 0.2824 | 1.28 | 0.1056 |
| HNMT | 11 | 5.478 | rs6430676 | C | 1.76 | 0.3206 | 1.37 | 0.1283 |

TABLE 5-continued

Hub (Group B-hub) SNPs: Summary of the hubs from the coexpression modules most significantly associated with heart failure and the association results of their corresponding SNPs with ejection fraction response in the Phase I and Phase II heart failure cohorts.

| Hub Gene | Module Size | Average d-Score | SNP | Minor Allele | Phase I OR | Phase I p-value | Phase II OR | Phase II p-value |
|---|---|---|---|---|---|---|---|---|
| C14orf29 | 26 | 4.977 | rs1953879 | T | 1.89 | 0.4307 | 1.38 | 0.1353 |
| SLC37A3 | 13 | 6.147 | rs6947516 | A | 0.17 | 0.08895 | 1.38 | 0.1525 |
| DTX1 | 14 | 5.512 | rs1732803 | T | 0.67 | 0.2484 | 1.24 | 0.1544 |
| SLC17A1 | 29 | 7.608 | rs1165196 | C | 0.58 | 0.1096 | 0.8 | 0.1588 |
| EME1 | 32 | 5.351 | rs17714829 | C | 0.39 | 0.2352 | 0.66 | 0.167 |
| ZNF238 | | 5.165 | rs11590416 | G | 0.53 | 0.1082 | 0.76 | 0.1869 |
| SOCS5 | | 5.802 | rs4953410 | G | 1.64 | 0.2349 | 1.25 | 0.1959 |

The d-score represents the statistical value from the analysis comparing gene expression in heart failure tissue versus normal heart tissue. The average d-score is the absolute statistical value averaged across all members of the network module that contains the noted gene as the hub. Phase I analyses tested associations for EF improvement by an absolute value greater than 20 percentage points using an additive logistic regression model. The Phase I cohort was age, sex and race-matched. Phase II analyses tested associations for EF improvement by an absolute value greater than 10 percentage points using an additive logistic regression model adjusted for age, sex and race.
OR = odds ratio per minor allele,
EF = ejection fraction.

TABLE 6

Literature Network (Group B-Lit) SNPs: Summary of the nexi from the literature networks most significantly associated with heart failure and the association results of their corresponding SNPs with ejection fraction response in the Phase I and Phase II heart failure cohorts.

| Hub Gene | Module Size | Average d-Score | SNP | Minor Allele | Phase I OR | Phase I p-value | Phase II OR | Phase II p-value |
|---|---|---|---|---|---|---|---|---|
| Top Hubs Ranked by Average Module d-score ||||||||| 
| A2M | 8 | 11.094 | rs226389 | G | 0.63 | 0.2145 | 0.78 | 0.1041 |
| ITIH5 | 6 | 8.534 | rs10508332 | G | 0.57 | 0.1378 | 0.97 | 0.8269 |
| ITIH5 | 6 | 8.534 | rs1931901 | A | 2.19 | 0.08623 | 0.8 | 0.1551 |
| ITIH5 | 6 | 8.534 | rs1931902 | A | 0.54 | 0.1586 | 0.99 | 0.9338 |
| ITIH5 | 6 | 8.534 | rs7097970 | C | 0.6 | 0.1177 | 1.06 | 0.7448 |
| ITIH1 | 7 | 8.111 | rs2710323 | G | 0.79 | 0.4141 | 1.06 | 0.6725 |
| GSPT1 | 7 | 8.047 | rs33660 | G | 1.46 | 0.3279 | 1.04 | 0.7995 |
| SLC1A7 | 8 | 7.319 | rs11206093 | C | 0.71 | 0.3918 | 0.97 | 0.8894 |
| SLC1A7 | 8 | 7.319 | rs1320594 | A | 0.58 | 0.1362 | 0.89 | 0.4288 |
| SLC1A7 | 8 | 7.319 | rs1679933 | G | 2.53 | 0.01498 | 1.06 | 0.7089 |
| SLC1A7 | 8 | 7.319 | rs1769299 | T | 0.64 | 0.3578 | 1.03 | 0.8684 |
| KCNIP2 | 8 | 7.086 | rs10883689 | A | 1.52 | 0.3043 | 1.13 | 0.4596 |
| NODAL | 10 | 7.085 | rs10762381 | C | 0.57 | 0.2012 | 0.7 | 0.01575 |
| ATP7B | 8 | 6.939 | rs1801249 | T | 1.47 | 0.342 | 1.24 | 0.1611 |
| ATP7B | 8 | 6.939 | rs754610 | A | 0.57 | 0.146 | 0.8 | 0.1206 |
| COMMD6 | 6 | 6.827 | rs12869081 | A | 1.32 | 0.4337 | 0.89 | 0.5771 |
| COMMD6 | 6 | 6.827 | rs9543956 | T | 1.74 | 0.1207 | 1.21 | 0.2243 |
| KCNK9 | 9 | 6.825 | rs11166920 | T | 2.47 | 0.03302 | 1.04 | 0.8211 |
| KCNK9 | 9 | 6.825 | rs759656 | C | 2.14 | 0.1119 | 0.94 | 0.6957 |
| KCNK9 | 9 | 6.825 | rs882555 | C | 1.57 | 0.1725 | 1.09 | 0.6032 |
| KCNK9 | 9 | 6.825 | rs885724 | C | 1.92 | 0.1484 | 0.98 | 0.9219 |
| KCNK9 | 9 | 6.825 | rs888346 | A | 1.89 | 0.1401 | 0.81 | 0.163 |
| PRKAG2 | 7 | 6.545 | rs2727528 | C | 1.71 | 0.03734 | 1.07 | 0.6765 |
| PRKAG2 | 7 | 6.545 | rs2727541 | C | 1.87 | 0.05437 | 0.85 | 0.2853 |
| PRKAG2 | 7 | 6.545 | rs7801616 | T | 2.2 | 0.0572 | 1.03 | 0.8472 |
| Top Hubs Ranked by Phase II p-values. ||||||||| 
| RASSF6 | 7 | 5.712 | rs12507775 | G | 1.4 | 0.3837 | 1.53 | 0.01209 |
| NODAL | 10 | 7.085 | rs10762381 | C | 0.57 | 0.2012 | 0.7 | 0.01575 |
| CHRM3 | 7 | 3.61 | rs665159 | C | 1.81 | 0.1042 | 1.41 | 0.01675 |
| BTAF1 | 9 | 4.106 | rs12763600 | G | 0.72 | 0.2892 | 1.45 | 0.01837 |
| LIN7A | 19 | 5.264 | rs7969498 | T | 0.62 | 0.2028 | 1.42 | 0.02552 |
| RAB22A | 6 | 5.274 | rs471661 | C | 0.53 | 0.1018 | 1.4 | 0.02745 |
| MAK | 8 | 4.585 | rs2009118 | T | 2.15 | 0.1506 | 1.39 | 0.04902 |
| PRPF4B | 8 | 4.649 | rs12198921 | C | 0.62 | 0.1276 | 0.74 | 0.05348 |
| BTC | 11 | 4.873 | rs4352548 | C | 1.77 | 0.18 | 1.36 | 0.06907 |
| ANTXR1 | 6 | 6.262 | rs7584948 | G | 1.36 | 0.4811 | 1.35 | 0.083 |
| A2M | 8 | 11.094 | rs226389 | G | 0.63 | 0.2145 | 0.78 | 0.1041 |
| NOBOX | 8 | 5.939 | rs1208208 | C | 1.83 | 0.06221 | 1.27 | 0.1071 |
| ATP7B | 8 | 6.939 | rs754610 | A | 0.57 | 0.146 | 0.8 | 0.1206 |
| KIR3DL2 | 11 | 6.033 | rs1654644 | G | 1.27 | 0.409 | 1.27 | 0.1233 |
| COG2 | 7 | 5.031 | rs2296799 | C | 0.19 | 0.01348 | 1.32 | 0.1277 |
| RRAGA | 6 | 6.451 | rs10125646 | G | 0.76 | 0.4111 | 0.8 | 0.1368 |

TABLE 6-continued

Literature Network (Group B-Lit) SNPs: Summary of the nexi from the literature networks most significantly associated with heart failure and the association results of their corresponding SNPs with ejection fraction response in the Phase I and Phase II heart failure cohorts.

| Hub Gene | Module Size | Average d-Score | SNP | Minor Allele | Phase I OR | Phase I p-value | Phase II OR | Phase II p-value |
|---|---|---|---|---|---|---|---|---|
| EPB41L1 | 6 | 4.533 | rs2746105 | A | 0.73 | 0.4998 | 0.77 | 0.1387 |
| CYP11B1 | 9 | 6.302 | rs6410 | A | 0.68 | 0.276 | 1.25 | 0.1438 |
| ITIH5 | 6 | 8.534 | rs1931901 | A | 2.19 | 0.08623 | 0.8 | 0.1551 |
| ANTXR 1 | 6 | 6.262 | rs4854550 | T | 0.7 | 0.4568 | 0.81 | 0.1572 |

The d-score represents the statistical value from the analysis comparing gene expression in heart failure tissue versus normal heart tissue. The average d-score is the absolute statistical value averaged across all members of the network module that contains the noted gene as the nexus. Phase I analyses tested associations for EF improvement by an absolute value greater than 20 percentage points using an additive logistic regression model. The Phase I cohort was age, sex and race-matched. Phase II analyses tested associations for EF improvement by an absolute value greater than 10 percentage points using an additive logistic regression model adjusted for age, sex and race.
OR = odds ratio per minor allele,
EF = ejection fraction.

TABLE 7

Replication of SNPs from other GWAS: Summary of association results for ejection fraction response in the Phase I and Phase II heart failure cohorts.

| SNP | Gene Symbol | Phenotype | Minor Allele | Phase I OR | Phase I p-value | Phase II OR | Phase II p-value |
|---|---|---|---|---|---|---|---|
| rs12623467 | NRXN1 | Nicotine Dependence | T | . | | 1.61 | 0.0267 |
| rs7903146 | TCF7L2 | Type II DM | T | 1.43 | 0.3637 | 1.38 | 0.04691 |
| rs10511311 | CD200 | Atrial Fibrillation | T | . | | 1.34 | 0.04834 |
| rs9939609 | FTO | Type II DM, BMI | A | . | | 1.33 | 0.07296 |
| rs13277254 | CHRNB3 | Nicotine Dependence | G | . | | 1.34 | 0.08167 |
| rs2383206 | CDKN2B | CAD | A | . | | 1.24 | 0.1385 |
| rs4506565 | TCF7L2 | Type II DM | T | . | | 1.24 | 0.1606 |
| rs10757278 | CDKN2B | Myocardial Infarction | G | | | 0.82 | 0.185 |
| rs2383207 | CDKN2B | AAA | A | 0.75 | 0.3797 | 1.2 | 0.2178 |
| rs662 | PON1 | CAD | G | 0.7 | 0.4543 | 1.2 | 0.2519 |
| rs1801282 | PPARG | Type II DM | G | . | | 1.26 | 0.2563 |
| rs10504543 | KCNB2 | LV Systolic Dimension | A | 1.91 | 0.1258 | 0.84 | 0.2757 |
| rs9465871 | CDKAL1 | Type II DM | C | . | | 1.18 | 0.3274 |
| rs8055236 | CDH13 | CAD | T | 1.93 | 0.1739 | 1.18 | 0.3462 |
| rs383830 | APC | CAD | T | . | | 1.18 | 0.3771 |
| rs1333049 | CDKN2B | CAD | G | | | 1.12 | 0.4386 |
| rs10490162 | NRXN1 | Nicotine Dependence | G | 1.07 | 0.8893 | 1.15 | 0.487 |
| rs4142041 | CTNNA3 | Nicotine Dependence | G | . | | 1.09 | 0.5405 |
| rs10501920 | CNTN5 | Atrial Fibrillation | G | . | | 0.89 | 0.5669 |
| rs10515869 | MAT2B | Heart Failure | C | 1.68 | 0.2101 | 1.07 | 0.6636 |
| rs2836823 | FLJ45139 | Nicotine Dependence | T | . | | 0.94 | 0.7026 |
| rs1379659 | SLIT2 | LV Diastolic Dimension | G | 1.58 | 0.3641 | 0.95 | 0.8026 |
| rs5215 | KCNJ11 | Type II DM | C | 1.34 | 0.3122 | 1.04 | 0.8212 |
| rs17672135 | FMN2 | CAD | C | . | | 0.96 | 0.8661 |
| rs2221299 | NRXN3 | Nicotine Dependence | A | . | | 1.06 | 0.8737 |
| rs3807375 | KCNH2 | QRS Duration | A | 0.97 | | 1.01 | 0.9458 |

Phase I analyses tested associations for EF improvement by an absolute value greater than 20 percentage points using an additive logistic regression model. The Phase I cohort was age, sex and race-matched. Phase II analyses tested associations for EF improvement by an absolute value greater than 10 percentage points using an additive logistic regression model adjusted for age, sex and race.
OR = odds ratio per minor allele,
EF = ejection fraction,
DM = diabetes mellitus,
BMI = body mass index,
AAA = abdominal aortic aneurysm,
CAD = coronary artery disease,
LV = left ventricular.

TABLE 8

| SNP | Allele | Program | Transcription factor | Sequence | Strand | Score |
|---|---|---|---|---|---|---|
| rs7767652 | C | TRANSFAC | LEF-1 | tCAAAG | + | 100 |
| | | | PMX1 | TAATCa | + | 100 |
| | | | TCF-4 | aaTCAAga | − | 97.6 |
| | | MatInspector | Sex determining | tccacATTAtaatcaaagaaagtac | + | 97.9 |

TABLE 8-continued

| SNP | Allele | Program | Transcription factor | Sequence | Strand | Score |
|---|---|---|---|---|---|---|
| | | | region Y | ttataatCAAAgaaagt | + | 95.9 |
| | | | TCF/LEF-1 | cattaTAATcaaagaaa | + | 95.7 |
| | | | Cone-rod homeobox-containing transcription factor (CRX) | | | |
| | | PROMO | LEF-1 | AATCAAAG | + | 98.6 |
| | | | TCF-4 | TAATCAAAGA | + | 97.2 |
| | | | TCF-4E | ATCAAAG | + | 96.8 |
| | | | GR | CAAAGAA | + | 96.2 |
| | | | SRY | TAATCAAAG | + | 94.9 |
| | | JASPAR | SRY | ATAATCAAA | + | 84.1 |
| | | | Nkx2.5 | ATAATCA | + | 82.7 |
| | | TFSearch | SRY | AATCAAA | + | 90.9 |
| | | | CdxA | TATAATC | + | 90.7 |
| | | | Oct1 | ATTATAATCAAAG | + | 86.2 |
| | T | TRANSFAC | PMX1 | TAATTa | + | 100 |
| | | | PMX1 | tAATTA | - | 100 |
| | | | DLX5 | AATTAa | + | 100 |
| | | | LHX3 | ATTAAa | + | 100 |
| | | | SATB1 | ataatTAAAGaaagta | + | 97.0 |
| | | | HOXA5 | attaTAATTaaagaaa | + | 95.3 |
| | | MatInspector | NK6 homeobox I | ttctTTAAttataat | - | 95.6 |
| | | | DLX 1, 2, and 5 binding sites | tccacattatAATTaaaga | + | 100 |
| | | | | tccacATTAtaattaaagaaagtac | + | 98.1 |
| | | | Sex determining region Y | ttctttaATTAatgtgg | - | 95.5 |
| | | | Homeobox C8/ Hox-3alpha | tccacattatAATTaaagaaagt | + | 90.0 |
| | | | LIM homeobox transcription factor 1. alpha | | | |
| | | PROMO | GR-beta | AATTA | + | 99.2 |
| | | | GR-beta | TAATT | + | 99.2 |
| | | JASPAR | SRY | TTAAAGAAA | + | 80.1 |
| | | | HOXA5 | CTTTAATT | - | 95.2 |
| | | | Pdx I | TTAATT | - | 94.0 |
| | | | Nkx2.5 | TTAATTA | - | 92.0 |
| | | TFSearch | CdxA | AATTAAA | + | 98.6 |
| | | | CdxA | TATAATT | + | 90.7 |

While the preferred embodiments of the invention have been illustrated and described, it will be appreciated that various changes can be made therein without departing from the spirit and scope of the invention.

What is claimed is:

1. A method of treating an individual for heart failure, the method comprising administering a therapeutically effective amount of an agonist of hypocretin receptor 2 (HCRTR2) to the individual, wherein the agonist of HCRTR2 is selected from the group consisting of orexin-A, orexin-B, [Ala1 1,D-Leu15]-orexin B, and SB-668875.

2. The method of claim 1, wherein the agonist of HCRTR2 is administered according to a regimen selected from the group consisting of a daily dosing regimen, a twice-a-week dosing regimen, or a three-times-a-week dosing regimen.

3. The method of claim 1, wherein multiple cycles of the method of treatment are administered to the individual for a time period sufficient to effect at least a partial recovery of heart function.

4. The method of claim 3, wherein the time period is one of either at least 6 months or at least 12 months.

5. The method of claim 4, wherein the individual shows at least a 10% improvement in left ventricular function.

6. The method of claim 4, wherein the individual shows at least a 20% improvement in left ventricular function.

7. The method of claim 1, wherein the agonist is administered orally, intravenously, intra-arterially, subcutaneously, intracerebroventricularly, intrathecally, or intranasally.

8. The method of claim 1, further comprising treatment with one or more other agents for treating heart failure selected from the group consisting of an angiotensin converting enzyme (ACE) inhibitor, an angiotensin II receptor blocker (ARB), a beta-blocker, digoxin, a diuretic, a blood vessel dilator, potassium, magnesium, an aldactone inhibitor, a calcium channel blocker, and an inotrope.

* * * * *

```
                          SEQUENCE LISTING

<160> NUMBER OF SEQ ID NOS: 17

<210> SEQ ID NO 1
<211> LENGTH: 52
<212> TYPE: DNA
<213> ORGANISM: Homo sapiens
<220> FEATURE:
<221> NAME/KEY: allele
<222> LOCATION: (27)..(27)
<223> OTHER INFORMATION: n is C or T
<220> FEATURE:
<221> NAME/KEY: misc_feature
<222> LOCATION: (27)..(27)
<223> OTHER INFORMATION: n is a, c, g, or t

<400> SEQUENCE: 1
gttgataaaa tattccacat tataatnaaa gaaagtacaa aaaagttaaa tg              52

<210> SEQ ID NO 2
<211> LENGTH: 68
<212> TYPE: DNA
<213> ORGANISM: Artificial Sequence
<220> FEATURE:
<223> OTHER INFORMATION: rs7767652-C forward primer
```

```
<400> SEQUENCE: 2
agctttataa tcaaagaaag ttataatcaa agaaagttat aatcaaagaa agttataatc    60
aaagaaag                                                             68

<210> SEQ ID NO 3
<211> LENGTH: 68
<212> TYPE: DNA
<213> ORGANISM: Artificial Sequence
<220> FEATURE:
<223> OTHER INFORMATION: rs7767652-C reverse primer

<400> SEQUENCE: 3
gatcctttct tgattataa ctttctttga ttataacttt ctttgattat aactttcttt    60
gattataa                                                             68

<210> SEQ ID NO 4
<211> LENGTH: 64
<212> TYPE: DNA
<213> ORGANISM: Artificial Sequence
<220> FEATURE:
<223> OTHER INFORMATION: rs7767652-T forward primer

<400> SEQUENCE: 4
agctttataa ttaaagaaat tataattaaa gaattataa ttaaagaaat tataattaaa    60
gaaa                                                                 64

<210> SEQ ID NO 5
<211> LENGTH: 64
<212> TYPE: DNA
<213> ORGANISM: Artificial Sequence
<220> FEATURE:
<223> OTHER INFORMATION: rs7767652-T reverse primer

<400> SEQUENCE: 5
gatctttctt taattataat ttctttaatt ataatttctt taattataat ttctttaatt    60
ataa                                                                 64

<210> SEQ ID NO 6
<211> LENGTH: 25
<212> TYPE: DNA
<213> ORGANISM: Homo sapiens

<400> SEQUENCE: 6
tccacattat aatcaaagaa agtac                                          25

<210> SEQ ID NO 7
<211> LENGTH: 17
<212> TYPE: DNA
<213> ORGANISM: Homo sapiens

<400> SEQUENCE: 7
ttataatcaa agaaagt                                                   17

<210> SEQ ID NO 8
<211> LENGTH: 17
<212> TYPE: DNA
<213> ORGANISM: Homo sapiens

<400> SEQUENCE: 8
cattataatc aaagaaa                                                   17
```

```
<210> SEQ ID NO 9
<211> LENGTH: 10
<212> TYPE: DNA
<213> ORGANISM: Homo sapiens

<400> SEQUENCE: 9
taatcaaaga                                                          10

<210> SEQ ID NO 10
<211> LENGTH: 13
<212> TYPE: DNA
<213> ORGANISM: Homo sapiens

<400> SEQUENCE: 10
attataatca aag                                                      13

<210> SEQ ID NO 11
<211> LENGTH: 16
<212> TYPE: DNA
<213> ORGANISM: Homo sapiens

<400> SEQUENCE: 11
ataattaaag aaagta                                                   16

<210> SEQ ID NO 12
<211> LENGTH: 16
<212> TYPE: DNA
<213> ORGANISM: Homo sapiens

<400> SEQUENCE: 12
attataatta aagaaa                                                   16

<210> SEQ ID NO 13
<211> LENGTH: 15
<212> TYPE: DNA
<213> ORGANISM: Homo sapiens

<400> SEQUENCE: 13
ttctttaatt ataat                                                    15

<210> SEQ ID NO 14
<211> LENGTH: 19
<212> TYPE: DNA
<213> ORGANISM: Homo sapiens

<400> SEQUENCE: 14
tccacattat aattaaaga                                                19

<210> SEQ ID NO 15
<211> LENGTH: 25
<212> TYPE: DNA
<213> ORGANISM: Homo sapiens

<400> SEQUENCE: 15
tccacattat aattaaagaa agtac                                         25

<210> SEQ ID NO 16
<211> LENGTH: 19
<212> TYPE: DNA
<213> ORGANISM: Homo sapiens

<400> SEQUENCE: 16
ttctttaatt ataatgtgg                                                19
```

```
<210> SEQ ID NO 17
<211> LENGTH: 23
<212> TYPE: DNA
<213> ORGANISM: Homo sapiens

<400> SEQUENCE: 17
tccacattat aattaaagaa agt                                               23
```